US011202838B2

(12) United States Patent
Kidambi et al.

(10) Patent No.: US 11,202,838 B2
(45) Date of Patent: Dec. 21, 2021

(54) SUBSTRATE DELIVERY OF EMBEDDED LIPOSOMES

(71) Applicant: NUtech Ventures, Lincoln, NE (US)

(72) Inventors: Srivatsan Kidambi, Lincoln, NE (US); Stephen L. Hayward, Lincoln, NE (US)

(73) Assignee: NUtech Ventures, Lincoln, NE (US)

( * ) Notice: Subject to any disclaimer, the term of this patent is extended or adjusted under 35 U.S.C. 154(b) by 0 days.

(21) Appl. No.: 15/752,668

(22) PCT Filed: Aug. 15, 2016

(86) PCT No.: PCT/US2016/047042
§ 371 (c)(1),
(2) Date: Feb. 14, 2018

(87) PCT Pub. No.: WO2017/031060
PCT Pub. Date: Feb. 23, 2017

(65) Prior Publication Data
US 2019/0030184 A1 Jan. 31, 2019

Related U.S. Application Data

(60) Provisional application No. 62/205,473, filed on Aug. 14, 2015.

(51) Int. Cl.
*A61K 47/34* (2017.01)
*C12N 15/113* (2010.01)
*A61K 47/69* (2017.01)
*A61K 9/127* (2006.01)
*A61K 47/61* (2017.01)
*A61K 31/704* (2006.01)

(52) U.S. Cl.
CPC ........ *A61K 47/6911* (2017.08); *A61K 9/1272* (2013.01); *A61K 31/704* (2013.01); *A61K 47/34* (2013.01); *A61K 47/61* (2017.08); *C12N 15/1135* (2013.01)

(58) Field of Classification Search
None
See application file for complete search history.

(56) References Cited

U.S. PATENT DOCUMENTS

| | | | |
|---|---|---|---|
| 8,062,853 B2 | 11/2011 | Abbott et al. | |
| 8,318,856 B2* | 11/2012 | Oh | A61K 47/61 514/44 R |
| 8,613,847 B2 | 12/2013 | Khaled et al. | |
| 8,685,538 B2* | 4/2014 | Torchilin | A61K 9/5138 428/403 |
| 10,278,927 B2* | 5/2019 | Hammond | A61K 9/0019 |
| 2006/0118754 A1 | 6/2006 | Steinbroner | |
| 2012/0051999 A1 | 3/2012 | Chung et al. | |
| 2012/0082717 A1* | 4/2012 | Char | A61P 31/04 424/450 |

OTHER PUBLICATIONS

Asher and Bignami, "Hyaluronate binding and CD44 expression in human glioblastoma cells and astrocytes," Exp. Cell Res, 1992, 203:80-90.
Balz et al., "The interplay of HER2/HER3/PI3K and EGFR/HER2/PLC-γ1 signalling in breast cancer cell migration and dissemination," The Journal of Pathology, 2012, 227:234.
De Ridder et al., "Invasiveness of human glioma cell lines in vitro: relation to tumorigenicity in athymic mice," Acta Neuropathol, 1987, 72:207-213.
Doyle et al., "Dimensions in cell migration," Current Opinion in Cell Biology, 2013, 25:642.
Emde et al., "Therapeutic strategies and mechanisms of tumorigenesis of HER2-overexpressing breast cancer," Critical Reviews in Oncology/Hematology, 2012, Supplement 1:e49-57.
Grothey et al., "C-erbB-2/ HER-2 upregulates fascin, an actin-bundling protein associated with cell motility, in human breast cancer cell lines," Oncogene, 2000, 19:4864.
Hayward et al., "Targeted Delivery of MicroRNA125a-5p by Engineered Lipid Nanoparticles for the Treatment of HER2 Positive Metastatic Breast Cancer," Journal of Biomedical Nanotechnology, 2016, 12:554-568.
Hayward et al. "Ionic Driven Embedment of Hyaluronic Acid Coated Liposomes in Polyelectrolyte Multilayer Films for Local Therapeutic Deliveiy," Scientific Reports, Oct. 2015, 5: 14683.
Huang and Manning, "A complex interplay between Akt, TSC2 and the two mTOR complexes," Biochemical Society Transactions, 2009: 37-217.
International Preliminary Report on Patentability in International Application No. PCT/US2016/047042, dated Feb. 20, 2018, 7 pages.
International Search Report and Written Opinion in International Application No. PCT/US2016/047042, dated Nov. 4, 2016, 16 pages.
Kleiner et al., "Evolution of implantable and insertable drug delivery systems," Journal of Controlled Release, 2014, 181: 1-10.
Landesman-Milo et al., "Hyaluronan grafted lipid-based nanoparticles as RNAi carriers for cancer cells," Cancer Lett, 2013, 334:221.
Manning and Catley, "AKT/PKB signaling: navigating downstream," Cell, 2007, 129:1261.
McCubrey et al., "Roles of the Raf/MEK/ERK pathway in cell growth, malignant transformation and drug resistance," Biochimica et Biophysica Acta, 2007, 1773:1263-84.
Natarajan et al., "Titanium Dioxide Nanoparticles Trigger Loss of Function and Perturbation of Mitochondrial Dynamics in Primary Hepatocytes," PLOS One, 2015, 10:e0134541.
Nishida et al., "MicroRNA-125a-5p is an independent prognostic factor in gastric cancer and inhibits the proliferation of human gastric cancer cells in combination with trastuzumab," Clin. Cancer Res, 2011, 17:2725.

(Continued)

Primary Examiner — Celeste A Roney
(74) Attorney, Agent, or Firm — Fish & Richardson P.C.

(57) ABSTRACT

This invention relates to compositions useful for localized and sustained release of therapeutic agents, and more particularly to functionalized liposomes embedded in a polyelectrolyte multilayer. Methods of preparing the compositions, methods of treating diseases, devices, and pharmaceutical compositions comprising the compositions are also provided.

14 Claims, 40 Drawing Sheets

Specification includes a Sequence Listing.

(56) References Cited

OTHER PUBLICATIONS

Peer et al., "Systemic leukocyte-directed siRNA delivery revealing cyclin D1 as an anti-inflammatory target," Science, 2008, 319, 627-630.
Platt and Szoka, "Anticancer therapeutics: targeting macromolecules and nanocarriers to hyaluronan or CD44, a hyaluronan receptor," Mol. Pharm. 2008, 5:474-486.
Puranik et al., "Recent Advances in Drug Eluting Stents," International Journal of Pharmaceutics, 2013, 441: 665-679.
Santarpia et al., "Targeting the MAPK-RAS-RAF signaling pathway in cancer therapy," Expert Opinion on Therapeutic Targets, 2012, 16:103-19.
Scott et al., "Coordinate suppression of ERBB2 and ERBB3 by enforced expression of micro-RNA miR-125a or miR-125bJ," Bio. Chem, 2007, 282:1479-86.
Tsigkas et al., "Drug-loaded particles: "Trojan horses" in the therapy of atherosclerosis," Atherosclerosis, 2016, 251: 528-530.
Vachon et al., "CD44-mediated phagocytosis induces inside-out activation of complement receptor-3 in murine macrophages," Blood, 2007, 110:4492-4502.
Vivers et al., "Role of macrophage CD44 in the disposal of inflammatory cell corpses," Clin. Sci. (Lond), 2002, 103:441-449.
Wilson et al., "Mitochondrial dysfunction and loss of glutamate uptake in primary astrocytes exposed to titanium dioxide nanoparticles," Nanoscale, 2015, 7:18477-18488.
Yerushalmi et al., "Ki67 in breast cancer: prognostic and predictive potential," The Lancet Oncology, 2010, 11:174-83.
Yoshida et al., "CD44 in human glioma correlates with histopathological grade and cell migration," Pathol. Int, 2012, 62:463-470.

\* cited by examiner

SUBSTRATE DELIVERY OF EMBEDDED LIPOSOMES

CROSS-REFERENCE TO RELATED APPLICATIONS

This application is a National Stage Application under 35 U.S.C. § 371 and claims the benefit of International Application No. PCT/US2016/047042, filed Aug. 15, 2016, which claims the benefit of U.S. Provisional Application Ser. No. 62/205,473, filed Aug. 14, 2015, the disclosure of which is incorporated herein by reference in its entirety.

TECHNICAL FIELD

This invention relates to compositions useful for localized and sustained release of therapeutic agents, and more particularly to functionalized liposomes embedded in a polyelectrolyte multilayer.

BACKGROUND

The engineering of drug delivery platforms facilitating spatial and temporal release of a therapeutic is one of the key challenges in biomedical research that can ultimately lead to society-wide improvement in disease management. Specifically, the drug delivery kinetics is particularly relevant when it is necessary to achieve effective dose and spatiotemporal release kinetics of the therapeutic agent at the intended site of injury. Delivery via immobilization of the therapeutic cargo to a solid platform demonstrates higher translatable success compared to delivery using the free "bolus" form by overcoming unfavorable burst kinetics, toxic offsite effects, and efficacy reduction due to systemic dilution.

SUMMARY

The present application provides, inter alia, a composition comprising:
i) one or more hyaluronic acid conjugated liposomes; and
ii) a polyelectrolyte multilayer.

In some embodiments, the polyelectrolyte multilayer comprises one or more independently selected polycationic polymers. In some embodiments, the polyelectrolyte multilayer comprises one polycationic polymer. In some embodiments, each of the polycationic polymers is independently selected from the group consisting of poly-D-lysine (PDL), poly-L-lysine (PLL), poly(diallyl dimethylammonium chloride) (PDAC), linear poly(ethylene imine) (LPEI), poly(allyl-amine hydrochloride) (PAH), chitosan (CHI), a poly(β-amino ester), and polyarginine.

In some embodiments, the polyelectrolyte multilayer comprises one or more independently selected polyanionic polymers. In some embodiments, the polyelectrolyte multilayer comprises one polyanionic polymer. In some embodiments, each of the polyanionic polymers is independently selected from the group consisting of poly(sodium styrene sulfonate) (SPS), poly(anetholesulfonic acid) (PAS), poly(acrylic acid) (PAA), poly(sodium vinylsulfonate) (PVS), graphene oxide (GO), dextran sulfate, collagen, and hyaluronic acid (HA).

In some embodiments, at least one of the polycationic polymers is poly-L-lysine (PLL) and at least one of the polyanionic polymers is poly(sodium styrene sulfonate) (SPS). In some embodiments, the ratio of PLL/SPS is from about 1 to about 2. In some embodiments, the ratio of PLL/SPS is from about 1 to about 1.75. In some embodiments, the ratio of PLL/SPS is from about 1 to about 1.5. In some embodiments, the polyelectrolyte multilayer comprises from about 2 to about 10 monolayers of PLL. In some embodiments, the polyelectrolyte multilayer comprises from about 2 to about 8 monolayers of PLL. In some embodiments, the polyelectrolyte multilayer comprises from about 2 to about 6 monolayers of PLL. In some embodiments, the polyelectrolyte multilayer comprises from about 3 to about 5 monolayers of PLL. In some embodiments, the polyelectrolyte multilayer comprises from about 2 to about 10 monolayers of SPS. In some embodiments, the polyelectrolyte multilayer comprises from about 2 to about 8 monolayers of SPS. In some embodiments, the polyelectrolyte multilayer comprises from about 2 to about 6 monolayers of SPS. In some embodiments, the polyelectrolyte multilayer comprises from about 3 to about 5 monolayers of SPS. In some embodiments, the polyelectrolyte multilayer comprises about 5 monolayers of PLL and about 4 monolayers of SPS.

In some embodiments, the hyaluronic acid is covalently bonded to the liposome. In some embodiments, the hyaluronic acid is conjugated on the surface of the liposome In some embodiments, the liposome comprises a hydrophilic core and a hydrophobic lipid bilayer.

In some embodiments, the liposome further comprises one or more therapeutic agents. In some embodiments, each of the therapeutic agents is independently localized in the hydrophilic core or hydrophobic lipid bilayer of the liposome. In some embodiments, each of the therapeutic agents is independently selected from the group consisting of a chemotherapeutic agent, a silencing RNA, a steroid, an immunosuppressant, an anti-microbial agent, an anti-fungal agent, an anti-inflammatory agent, a gene therapy agent, an anti-angiogenic agent, and a CRISPR/Cas9 agent. In some embodiments, at least one of the therapeutic agents is a chemotherapeutic agent or a silencing RNA.

In some embodiments, at least one of the chemotherapeutic agents is selected from the group consisting of an alkylating agent, an anti-metabolite, an anti-tumor antibiotic, a topoisomerase inhibitor, a mitotic inhibitor, a plant alkaloid, a microtubule inhibitor, a DNA linking agent, an immunotherapeutic agent, and a differentiating agent In some embodiments, at least one of the chemotherapeutic agents is an anti-tumor antibiotic. In some embodiments, at least one of the chemotherapeutic agents is doxorubicin.

In some embodiments, the liposome further comprises a fluorescently tagged lipid. In some embodiments, the fluorescently tagged lipid is a fluorescently tagged cholesterol. In some embodiments, the liposome further comprises a targeting moiety. In some embodiments, the targeting moiety is conjugated to the hyaluronic acid. In some embodiments, the targeting moiety is selected from the group consisting of an antibody, a small molecule, a polypeptide, an aptamer, a folate, a transferrin, a glycoprotein, an integrin, and a carbohydrate.

In some embodiments, the composition further comprises an additional polyelectrolyte multilayer.

In some embodiments, the additional polyelectrolyte multilayer comprises one or more independently selected polycationic polymers. In some embodiments, the additional polyelectrolyte multilayer comprises one polycationic polymer. In some embodiments, each of the polycationic polymers is independently selected from the group consisting of poly-D-lysine (PDL), poly-L-lysine (PLL), poly(diallyl dimethylammonium chloride) (PDAC), linear poly(ethylene imine) (LPEI), poly(allyl-amine hydrochloride) (PAH), chitosan (CHI), a poly(β-amino ester), and polyarginine.

In some embodiments, the additional polyelectrolyte multilayer comprises one or more independently selected polyanionic polymers. In some embodiments, the additional polyelectrolyte multilayer comprises one polyanionic polymer. In some embodiments, each of the polyanionic polymers is independently selected from the group consisting of poly(sodium styrene sulfonate) (SPS), poly(anetholesulfonic acid) (PAS), poly(acrylic acid) (PAA), poly(sodium vinylsulfonate) (PVS), graphene oxide (GO), dextran sulfate, collagen, and hyaluronic acid (HA).

In some embodiments, at least one of the polycationic polymers is poly-L-lysine (PLL) and at least one of the polyanionic polymers is poly(sodium styrene sulfonate) (SPS).

In some embodiments, the polyelectrolyte multilayer is prepared using sequential deposition of the polycationic polymer and the polyanionic polymer. In some embodiments, the additional polyelectrolyte multilayer is prepared using sequential deposition of the polycationic polymer and the polyanionic polymer.

In some embodiments, the one or more hyaluronic acid conjugated liposomes is deposited onto the polyelectrolyte multilayer. In some embodiments, the additional polyelectrolyte multilayer is deposited onto the one or more hyaluronic acid conjugated liposomes.

In some embodiments, the composition is further deposited onto a substrate. In some embodiments, the substrate is selected from the group consisting of a medical device, a tablet, a capsule, a bandage, a gel, and a nanoparticle. In some embodiments, the medical device is selected from the group consisting of a stent, a catheter, a syringe, a needle, a microneedle, a medical implant, a metal rod, a cardiac pace maker, a surgical staple, a surgical suture, a needle, and a balloon.

In some embodiments:
the one or more hyaluronic acid conjugated liposomes further comprise one or more therapeutic agents; and
the polyelectrolyte multilayer comprises one or more independently selected polycationic polymers.

In some embodiments:
the one or more hyaluronic acid conjugated liposomes further comprise one or more therapeutic agents;
the polyelectrolyte multilayer comprises one or more independently selected polycationic polymers; and
each of the polycationic polymers is independently selected from the group consisting of poly-D-lysine (PDL), poly-L-lysine (PLL), poly(diallyl dimethylammonium chloride) (PDAC), linear poly(ethylene imine) (LPEI), poly(allyl-amine hydrochloride) (PAH), chitosan (CHI), a poly(β-amino ester), and polyarginine.

In some embodiments:
the one or more hyaluronic acid conjugated liposomes further comprise one or more therapeutic agents;
the polyelectrolyte multilayer comprises a polycationic polymer selected from the group consisting of poly-D-lysine (PDL), poly-L-lysine (PLL), poly(diallyl dimethylammonium chloride) (PDAC), linear poly(ethylene imine) (LPEI), poly(allyl-amine hydrochloride) (PAH), chitosan (CHI), a poly(β-amino ester), and polyarginine.

In some embodiments:
the one or more hyaluronic acid conjugated liposomes further comprise one or more therapeutic agents; and
the polyelectrolyte multilayer comprises one or more independently selected polyanionic polymers.

In some embodiments:
the one or more hyaluronic acid conjugated liposomes further comprise one or more therapeutic agents;
the polyelectrolyte multilayer comprises one or more independently selected polanionic polymers; and
each of the polyanionic polymers is independently selected from the group consisting of poly(sodium styrene sulfonate) (SPS), poly(anetholesulfonic acid) (PAS), poly(acrylic acid) (PAA), poly(sodium vinylsulfonate) (PVS), graphene oxide (GO), dextran sulfate, collagen, and hyaluronic acid (HA).

In some embodiments:
the one or more hyaluronic acid conjugated liposomes further comprise one or more therapeutic agents;
the polyelectrolyte multilayer comprises a polyanionic polymer selected from the group consisting of poly(sodium styrene sulfonate) (SPS), poly(anetholesulfonic acid) (PAS), poly(acrylic acid) (PAA), poly(sodium vinylsulfonate) (PVS), graphene oxide (GO), dextran sulfate, collagen, and hyaluronic acid (HA).

In some embodiments:
the one or more hyaluronic acid conjugated liposomes further comprise one or more therapeutic agents;
the polyelectrolyte multilayer comprises one or more independently selected polycationic polymers and one or more independently selected polyanionic polymers;
wherein each of the polycationic polymers is independently selected from the group consisting of poly-D-lysine (PDL), poly-L-lysine (PLL), poly(diallyl dimethylammonium chloride) (PDAC), linear poly(ethylene imine) (LPEI), poly(allyl-amine hydrochloride) (PAH), chitosan (CHI), a poly(β-amino ester), and polyarginine; and
each of the polyanionic polymers is independently selected from the group consisting of poly(sodium styrene sulfonate) (SPS), poly(anetholesulfonic acid) (PAS), poly(acrylic acid) (PAA), poly(sodium vinylsulfonate) (PVS), graphene oxide (GO), dextran sulfate, collagen, and hyaluronic acid (HA).

In some embodiments:
the one or more hyaluronic acid conjugated liposomes further comprise one or more therapeutic agents;
the polyelectrolyte multilayer comprises one polycationic polymer and one polyanionic polymer;
wherein the polycationic polymer is selected from the group consisting of poly-D-lysine (PDL), poly-L-lysine (PLL), poly(diallyl dimethylammonium chloride) (PDAC), linear poly(ethylene imine) (LPEI), poly(allyl-amine hydrochloride) (PAH), chitosan (CHI), a poly(β-amino ester), and polyarginine; and
the polyanionic polymer is selected from the group consisting of poly(sodium styrene sulfonate) (SPS), poly(anetholsulfonic acid) (PAS), poly(acrylic acid) (PAA), poly(sodium vinylsulfonate) (PVS), graphene oxide (GO), dextran sulfate, collagen, and hyaluronic acid (HA).

In some embodiments, at least one of the polycationic polymers is poly-L-lysine (PLL) and at least one of the polyanionic polymers is poly(sodium styrene sulfonate) (SPS). In some embodiments, the ratio of PLL/SPS is from about 1 to about 2. In some embodiments, the ratio of PLL/SPS is from about 1 to about 1.75. In some embodiments, the ratio of PLL/SPS is from about 1 to about 1.5. In some embodiments, the polyelectrolyte multilayer comprises from about 2 to about 10 monolayers of PLL. In some embodiments, the polyelectrolyte multilayer comprises from about 2 to about 8 monolayers of PLL. In some embodiments, the polyelectrolyte multilayer comprises from about 2 to about 6 monolayers of PLL. In some embodiments, the polyelectrolyte multilayer comprises from about 3 to about 5 monolayers of PLL. In some embodiments, the polyelectrolyte multilayer comprises from about 2 to about 10 monolayers of SPS. In some embodiments, the polyelectrolyte multilayer comprises from about 2 to about 8 monolayers of SPS. In some embodiments, the polyelectrolyte multilayer comprises from about 2 to about 6 monolayers of SPS. In some embodiments, the polyelectrolyte multilayer comprises from about 3 to about 5 monolayers of SPS. In some embodiments, the polyelectrolyte multilayer comprises about 5 monolayers of PLL and about 4 monolayers of SPS.

In some embodiments, the liposome further comprises a targeting moiety. In some embodiments, the targeting moiety is conjugated to the hyaluronic acid. In some embodiments, the targeting moiety is selected from the group consisting of an antibody, a small molecule, a polypeptide, an aptamer, a folate, a transferrin, a glycoprotein, an integrin, and a carbohydrate.

In some embodiments, the composition further comprises an additional polyelectrolyte multilayer. In some embodiments, the additional polyelectrolyte multilayer comprises one or more independently selected polycationic polymers. In some embodiments, the additional polyelectrolyte multilayer comprises one polycationic polymer. In some embodiments, each of the polycationic polymers is independently selected from the group consisting of poly-D-lysine (PDL), poly-L-lysine (PLL), poly(diallyl dimethylammonium chloride) (PDAC), linear poly(ethylene imine) (LPEI), poly(allyl-amine hydrochloride) (PAH), chitosan (CHI), a poly(β-amino ester), and polyarginine. In some embodiments, the additional polyelectrolyte multilayer comprises one or more independently selected polyanionic polymers. In some embodiments, the additional polyelectrolyte multilayer comprises two independently selected polyanionic polymers. In some embodiments, each of the polyanionic polymers is independently selected from the group consisting of poly(sodium styrene sulfonate) (SPS), poly(anetholesulfonic acid) (PAS), poly(acrylic acid) (PAA), poly(sodium vinylsulfonate) (PVS), graphene oxide (GO), dextran sulfate, collagen, and hyaluronic acid (HA). In some embodiments, at least one of the polycationic polymers is poly-L-lysine (PLL) and at least one of the polycationic polymers is poly(sodium styrene sulfonate) (SPS).

In some embodiments, the polyelectrolyte multilayer is prepared using sequential deposition of the polycationic polymer and the polyanionic polymer. In some embodiments, the additional polyelectrolyte multilayer is prepared using sequential deposition of the polycationic polymer and the polyanionic polymer. In some embodiments, the one or more hyaluronic acid conjugated liposomes is deposited onto the polyelectrolyte multilayer. In some embodiments, the additional polyelectrolyte multilayer is deposited onto the one or more hyaluronic acid conjugated liposomes.

In some embodiments, the composition is further deposited onto a substrate. In some embodiments, the substrate is selected from the group consisting of a medical device, a tablet, a capsule, a bandage, a gel, and a nanoparticle. In some embodiments, the medical device is selected from the group consisting of a stent, a catheter, a syringe, a needle, a microneedle, a medical implant, a metal rod, a cardiac pace maker, a surgical staple, a surgical suture, a needle, and a balloon.

The present application further provides a device coated with a composition comprising:
i) one or more hyaluronic acid conjugated liposomes; and
ii) a polyelectrolyte multilayer.

In some embodiments, the device is a medical device selected from the group consisting of a stent, a catheter, a syringe, a needle, a microneedle, a medical implant, a metal rod, a cardiac pace maker, a surgical staple, a surgical suture, a needle, and a balloon. In some embodiments, the device further comprises an additional polyelectrolyte multilayer deposited onto the one or more hyaluronic acid conjugated liposomes.

The present application further provides a tablet coated with a composition comprising:
i) one or more hyaluronic acid conjugated liposomes; and
ii) a polyelectrolyte multilayer.

In some embodiments, the tablet further comprises an additional polyelectrolyte multilayer deposited onto the one or more hyaluronic acid conjugated liposomes.

The present application further provides a method of preparing a composition provided herein, the method comprising:
i) sequentially depositing two or more polyionic polymers to form the polyelectrolyte multilayer; and
ii) depositing the one or more hyaluronic acid conjugated liposomes onto the polyelectrolyte multilayer.

In some embodiments, at least one of the polyionic polymers is a polycationic polymer and at least one of the polyionic polymers is polyanionic polymer. In some embodiments, the sequential depositing comprises sequential depositing of the two or more polyionic polymers onto the surface of a substrate.

In some embodiments, the substrate is selected from the group consisting of a medical device, a tablet, a capsule, a bandage, a gel, and a nanoparticle. In some embodiments, the medical device is selected from the group consisting of a stent, a catheter, a syringe, a needle, a microneedle, a medical implant, a metal rod, a cardiac pace maker, a surgical staple, a surgical suture, a needle, and a balloon.

In some embodiments, step ii) comprises contacting the one or more hyaluronic acid conjugated liposomes with the polyelectrolyte multilayer at about room temperature.

The present application further provides a method of preparing a composition provided herein, the method comprising:
i) sequentially depositing two or more polyionic polymers to form the polyelectrolyte multilayer;
ii) depositing the one or more hyaluronic acid conjugated liposomes onto the polyelectrolyte multilayer; and
iii) depositing the additional polyelectrolyte multilayer onto the one or more hyaluronic acid conjugated liposomes.

In some embodiments, the sequential depositing comprises sequential depositing of the two or more polyionic polymers onto the surface of a substrate.

In some embodiments, step ii) comprises contacting the one or more hyaluronic acid conjugated liposomes with the polyelectrolyte multilayer at about room temperature.

In some embodiments, the contacting is performed from about 1 to about 10 hours. In some embodiments, the contacting is performed from about 2 to about 5 hours.

In some embodiments, at least one of the polyionic polymers is a polycationic polymer and at least one of the polyionic polymers is polyanionic polymer. In some embodiments, each of the polycationic polymers is independently selected from the group consisting of poly-D-lysine (PDL), poly-L-lysine (PLL), poly(diallyl dimethylammonium chloride) (PDAC), linear poly(ethylene imine) (LPEI), poly(allyl-amine hydrochloride) (PAH), chitosan (CHI), a poly(β-amino ester), and polyarginine. In some embodiments, each of the polyanionic polymers is an independently selected from the group consisting of poly(sodium styrene sulfonate) (SPS), poly(anetholesulfonic acid) (PAS), poly (acrylic acid) (PAA), poly(sodium vinylsulfonate) (PVS), graphene oxide (GO), dextran sulfate, collagen, and hyaluronic acid (HA).

The present application further provides a method for controlled release of one or more therapeutic agents, comprising administering to a subject a composition provided herein. The present application further provides a method for delayed release of one or more therapeutic agents, comprising administering to a subject a composition provided herein. In some embodiments, the method is performed ex vivo. In some embodiments, the method is performed in vivo.

The present application further provides a method of treating a disease in a subject in need thereof, comprising administering to the subject a composition provided herein. In some embodiments, the composition releases the one or more therapeutic agents as a controlled release. In some embodiments, the composition releases the one or more therapeutic agents as a delayed release. In some embodiments, the administration comprises contacting a diseased cell with a composition provided herein. In some embodiments, the method is performed ex vivo. In some embodiments, the method is performed in vivo. In some embodiments, the disease is a cancer selected from the group consisting of pancreatic cancer, bladder cancer, brain cancer, breast cancer, colon cancer, endometrial cancer, gastrointestinal cancer, a hematological cancer, liver cancer, lung cancer, prostate cancer, skin cancer, stomach cancer, and renal cancer. In some embodiments, the cancer is breast cancer. In some embodiments, the cancer is brain cancer. In some embodiments, the brain cancer is glioblastoma.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

DESCRIPTION OF DRAWINGS

In FIG. 10A, cholesterol tagged HALNPs were incubated with the 21MT-1 cells for 5 hours and measured for co-localization with lysosomes to determine the fraction of viable therapeutic that escapes the nanoparticle degradation pathway. In FIG. 10B, confocal Microscopy with a Z-axis transformation of 21MT-1 cells at 100× zoom was used to validate cytoplasmic delivery using the nucleus as a reference point inside the cell (XZ plane shows the height and width of the cell).

FIG. 11A shows phase contrast microscopy analysis of cellular proliferation (transfection performed at time=0 hr.). FIG. 11B shows an MTT assay at 72-hours post transfection used to confirm the capacity and specificity of miR125a-5p to significantly reduce proliferation. Scramble miR was used as a negative control (**$P<0.005$, n=4). FIG. 11C shows phase contrast microscopy analysis of migration potential (scratch made in confluent cell monolayer 72 h following transfection): 27 total measurements were taken at each time point for each sample type. FIG. 11D shows a three dimensional graphical depiction of the change in scratch width of each sample type during the 48 h migration assay. FIG. 11E shows one-way Anova graphical representation of the scratch width during the migration assay (at time=0 h, 24 h, and 48 h). Error bars shown are 95% confidence interval.

FIG. 14D shows quantitative confocal microscopy images collected following an analogous 3 h incubation time with HALNPs to validate the flow uptake data. The confocal scale bars are 50 μm.

FIG. 17A shows live cell confocal microscopy images with z-axis stacking to probe the HALNP and lysosome co-localization patterns. FIG. 17B shows Z-axis transformation analysis with optical zoom to validate lysosomal evasion and subsequent achievement of homogenous cytoplasmic distribution in the A172 GBM cell. The cell nucleus was used as an internal reference point (XZ and YZ planes show the cell height and width, and height and length, respectively). For both confocal analyses a 5 h incubation time was used and the scale bars are 10 μm.

DETAILED DESCRIPTION

Figure 1A:
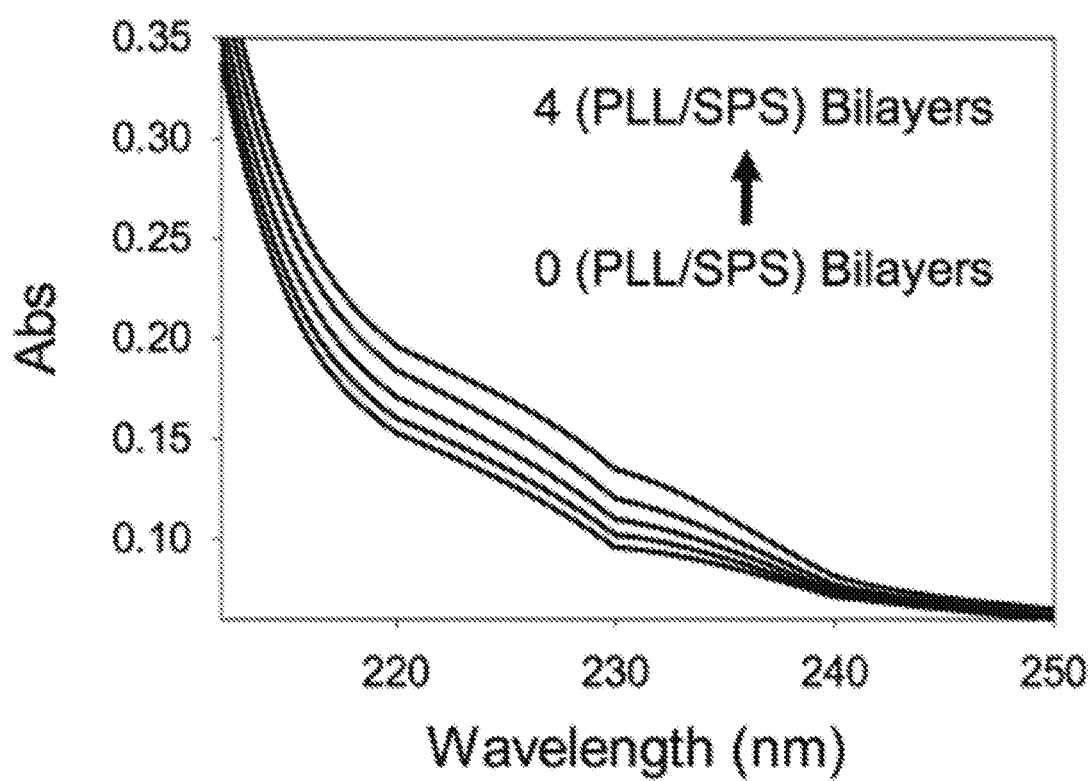
FIG. 1A shows a representative UV spectrum analysis of bilayer deposition.

The ability to control the spatial distribution and temporal release of a therapeutic remains a central challenge for biomedical research. Delivery via immobilization of therapeutic cargo to a solid platform demonstrates higher translatable success compared to delivery using the free "bolus" form by overcoming unfavorable burst kinetics, toxic offsite effects, and/or efficacy reduction due to systemic dilution. Although considerable progress has been made, there is a lack of development of a substrate-mediated delivery system capable of simultaneously controlled and truly localized delivery of therapeutics.

Accordingly, the present application provides the development and optimization of a novel substrate mediated therapeutic delivery system composed of hyaluronic acid covalently functionalized liposomes (HALNPs) embedded into a polyelectrolyte multilayer (PEM) platform via ionic stabilization.

Compositions

The present application provides, inter alia, a composition comprising:
  i) one or more hyaluronic acid conjugated liposomes; and
  ii) a polyelectrolyte multilayer.

As used herein, the term "polyelectrolyte multilayer" (i.e., PEM) refers to a multilayer formed by the deposition of one or more polyionic polymeric thin films. In some embodiments, the polyelectrolyte multilayer comprises two or more independently selected polyionic polymers, for example, three or more, four or more, five or more, six or more, seven or more, eight or more, nine or more, or ten or more independently selected polyionic polymers. In some embodiments, the polyelectrolyte multilayer comprises from about 2 to about 10 polyionic polymers, for example, 2 to 10, 2 to 8, 2 to 6, 2 to 4, 4 to 10, 4 to 8, 4 to 6, 6 to 10, 6 to 8, or 8 to 10 polyionic polymers. In some embodiments, the polyelectrolyte multilayer comprises 2 independently selected polyionic polymers, 3 independently selected polyionic polymers, 4 independently selected polyionic polymers, 5 independently selected polyionic polymers, 6 independently selected polyionic polymers, 7 independently selected polyionic polymers, 8 independently selected polyionic polymers, 9 independently selected polyionic polymers, 10 independently selected polyionic polymers, and the like.

In some embodiments, the polyelectrolyte multilayer comprises one or more independently selected polycationic polymers. As used herein, the term "polycationic polymer" refers to a polymer having one or more positively-charged repeat units. In some embodiments, the polycationic polymer comprises more than one positively-charged repeat unit. In some embodiments, each repeat unit of the polycationic polymer may be positively charged or neutral, wherein at least one repeat unit of the polycationic polymer is positively charged. In some embodiments, each repeat unit of the polycationic polymer is positively charged. In some embodiments, the polycationic polymer comprises at least two positively charged repeat units and at least one neutral repeat unit. In some embodiments, the polycationic polymer is a block copolymer comprising at least two repeat units having a positive charge. In some embodiments, the polycationic polymer is a copolymer comprising at least two repeat units having a positive charge. Example polycationic polymers include, but are not limited to, poly-D-lysine (PDL), poly-L-lysine (PLL), poly(diallyl dimethylammonium chloride) (PDAC), linear poly(ethylene imine) (LPEI), poly(allyl-amine hydrochloride) (PAH), chitosan (CHI), a poly($\beta$-amino ester), polyarginine, polyethyleneimine (PEI), poly (acrylic acid) (PAA), and poly(2-dimethylaminoethyl methacrylate) (PDMAEMA), and mixtures thereof.

In some embodiments, the polyelectrolyte multilayer comprises at least one polycationic layer. In some embodiments, the polyelectrolyte multilayer comprises one polycationic layer. In some embodiments, the polyelectrolyte multilayer comprises at least one polycationic polymer. In some embodiments, the polyelectrolyte multilayer comprises one polycationic polymer. In some embodiments, each of the polycationic polymers are independently selected from the group consisting of poly-D-lysine (PDL), poly-L-lysine (PLL), poly(diallyl dimethylammonium chloride) (PDAC), linear poly(ethylene imine) (LPEI), poly (allyl-amine hydrochloride) (PAH), chitosan (CHI), a poly ($\beta$-amino ester), polyarginine, and mixtures thereof. In some embodiments, the polycationic polymer is a copolymer or block copolymer comprising two or more independently selected repeat units, wherein at least one repeat unit is positively charged (e.g. L-lysine). In some embodiments, at least one of the polycationic polymers is poly-L-lysine (PLL).

In some embodiments, the polyelectrolyte multilayer comprises one or more independently selected polyanionic polymers. As used herein, the term "polyanionic polymer" refers to a polymer one or more negatively-charged repeat units. In some embodiments, the polyanionic polymer has more than one negatively-charged repeat unit. In some embodiments, each repeat unit of the polyanionic polymer may be negatively charged or neutral, wherein at least two of the repeats units are negatively charged. In some embodiments, the polyanionic polymer comprises at least two negatively charged repeat units and at least one neutral repeat unit. In some embodiments, the polyanionic polymer is a block copolymer comprising at least two repeat units having a negative charge. In some embodiments, the polyanionic polymer is a copolymer comprising at least two repeat units having a negative charge. In some embodiments, each repeat unit of the polyanionic polymer is negatively charged. Example polyanionic polymers include, but are not limited to, poly(sodium styrene sulfonate) (SPS), poly(anetholesulfonic acid) (PAS), poly(acrylic acid) (PAA), poly(sodium vinylsulfonate) (PVS), graphene oxide (GO), dextran sulfate, collagen, hyaluronic acid (HA), heparin, and mixtures thereof.

In some embodiments, the polyelectrolyte multilayer comprises at least one polyanionic layer. In some embodiments, the polyelectrolyte multilayer comprises one polyanionic layer. In some embodiments, the polyelectrolyte multilayer comprises at least one polyanionic polymer. In some embodiments, the polyelectrolyte multilayer comprises one polyanionic polymer. In some embodiments, each of the polyanionic polymers is independently selected from the group consisting of poly(sodium styrene sulfonate) (SPS), poly(anetholesulfonic acid) (PAS), poly(acrylic acid) (PAA), poly(sodium vinylsulfonate) (PVS), graphene oxide (GO), dextran sulfate, collagen, and hyaluronic acid (HA), and mixtures thereof. In some embodiments, the polyanionic polymer is a copolymer or block copolymer comprising two or more independently selected repeat units, wherein at least one repeat unit is negatively charged (e.g. sodium styrene sulfonate). In some embodiments, at least one of the polyanionic polymers is poly(sodium styrene sulfonate) (SPS).

In some embodiments, the polyelectrolyte layer comprises at least one polycationic layer and at least one polyanionic layer. In some embodiments, the polyelectrolyte layer comprises at least one polycationic polymer and at least one polyanionic polymer. In some embodiments, the ratio of the polycationic polymer or layer/polyanionic polymer or layer is from about 1 to about 2, for example, from about 1 to about 2, from about 1 to about 1.95, from about 1 to about 1.75, from about 1 to about 1.5, from about 1 to about 1.35, from about 1 to about 1.25, from about 1 to about 1.1, from about 1 to about 1.05, from about 1.05 to about 2, from about 1.05 to about 1.95, from about 1.05 to about 1.75, from about 1.05 to about 1.5, from about 1.05 to about 1.35, from about 1.05 to about 1.25, from about 1.05 to about 1.1, from about 1.1 to about 2, from about 1.1 to about 1.95, from about 1.1 to about 1.75, from about 1.1 to about 1.5, from about 1.1 to about 1.35, from about 1.1 to about 1.25, from about 1.25 to about 2, from about 1.25 to about 1.95, from about 1.25 to about 1.75, from about 1.25 to about 1.5, from about 1.25 to about 1.35, from about 1.35 to about 2, from about 1.35 to about 1.95, from about 1.35 to about 1.75, from about 1.35 to about 1.5, from about 1.5 to about 2, from about 1.5 to about 1.95, from about 1.5 to about 1.75, from about 1.75 to about 2, from about 1.75 to about 1.95, or from about 1.95 to about 2. In some embodiments, the ratio of the polycationic polymer or layer/polyanionic polymer or layer is from about 1 to about 1.75. In some embodiments, the ratio of the polycationic polymer or layer/polyanionic polymer or layer is from about 1 to about 1.5.

In some embodiments, at least one of the polycationic polymers is poly-L-lysine (PLL) and at least one of the polyanionic polymers is poly(sodium styrene sulfonate) (SPS). In some embodiments, the ratio of PLL/SPS is from about 1 to about 2, for example, from about 1 to about 2, from about 1 to about 1.95, from about 1 to about 1.75, from about 1 to about 1.5, from about 1 to about 1.35, from about 1 to about 1.25, from about 1 to about 1.1, from about 1 to about 1.05, from about 1.05 to about 2, from about 1.05 to about 1.95, from about 1.05 to about 1.75, from about 1.05 to about 1.5, from about 1.05 to about 1.35, from about 1.05 to about 1.25, from about 1.05 to about 1.1, from about 1.1 to about 2, from about 1.1 to about 1.95, from about 1.1 to about 1.75, from about 1.1 to about 1.5, from about 1.1 to about 1.35, from about 1.1 to about 1.25, from about 1.25 to about 2, from about 1.25 to about 1.95, from about 1.25 to about 1.75, from about 1.25 to about 1.5, from about 1.25 to about 1.35, from about 1.35 to about 2, from about 1.35 to about 1.95, from about 1.35 to about 1.75, from about 1.35 to about 1.5, from about 1.5 to about 2, from about 1.5 to about 1.95, from about 1.5 to about 1.75, from about 1.75 to about 2, from about 1.75 to about 1.95, or from about 1.95 to about 2. In some embodiments, the ratio of PLL/SPS is from about 1 to about 1.75. In some embodiments, the ratio of PLL/SPS is from about 1 to about 1.5.

In some embodiments, the polyelectrolyte multilayer comprises from about 2 to about 50 monolayers of one or more independently selected polycationic polymers, for example, about 2, about 3, about 4, about 5, about 6, about 7, about 8, about 9, about 10, about 20, about 30, about 40, or about 50 monolayers of the one or more independently selected cationic polymers. In some embodiments, the polyelectrolyte multilayer comprises from about 2 to about 50 monolayers of the one or more independently selected polycationic polymers. In some embodiments, the polyelectrolyte multilayer comprises from about 2 to about 20 monolayers of the one or more independently selected polycationic polymers. In some embodiments, the polyelectrolyte multilayer comprises from about 2 to about 10 monolayers of the one or more independently selected polycationic polymers. In some embodiments, the polyelectrolyte multilayer comprises from about 2 to about 5 monolayers of the one or more independently selected polycationic polymers. In some embodiments, the polyelectrolyte multilayer comprises from about 5 to about 50 monolayers of the one or more independently selected polycationic polymers. In some embodiments, the polyelectrolyte multilayer comprises from about 5 to about 20 monolayers of the one or more independently selected polycationic polymers. In some embodiments, the polyelectrolyte multilayer comprises from about 5 to about 10 monolayers of the one or more independently selected polycationic polymers. In some embodiments, the polyelectrolyte multilayer comprises from about 10 to about 50 monolayers of the one or more independently selected polycationic polymers. In some embodiments, the polyelectrolyte multilayer comprises from about 10 to about 20 monolayers of the one or more independently selected polycationic polymers. In some embodiments, the polyelectrolyte multilayer comprises from about 20 to about 50 monolayers of the one or more independently selected polycationic polymers.

In some embodiments, the polyelectrolyte multilayer comprises from about 2 to about 50 monolayers of a polycationic polymer, for example, about 2, about 3, about 4, about 5, about 6, about 7, about 8, about 9, about 10, about 20, about 30, about 40, or about 50 of the one or more independently selected cationic polymers. In some embodiments, the polyelectrolyte multilayer comprises from about 2 to about 50 monolayers of the polycationic polymer. In some embodiments, the polyelectrolyte multilayer comprises from about 2 to about 20 monolayers of the polycationic polymer. In some embodiments, the polyelectrolyte multilayer comprises from about 2 to about 10 monolayers of the polycationic polymer. In some embodiments, the polyelectrolyte multilayer comprises from about 2 to about 5 monolayers of the polycationic polymer. In some embodiments, the polyelectrolyte multilayer comprises from about 5 to about 50 monolayers of the polycationic polymer. In some embodiments, the polyelectrolyte multilayer comprises from about 5 to about 20 monolayers of the polycationic polymer. In some embodiments, the polyelectrolyte multilayer comprises from about 5 to about 10 monolayers of the polycationic polymer. In some embodiments, the polyelectrolyte multilayer comprises from about 10 to about 50 monolayers of the polycationic polymer. In some embodiments, the polyelectrolyte multilayer comprises from about 10 to about 20 monolayers of the polycationic polymer. In some embodiments, the polyelectrolyte multilayer comprises from about 20 to about 50 monolayers of the polycationic polymer. In some embodiments, the polyelectrolyte multilayer comprises from about 2 to about 50 monolayers of PLL, about 2, about 3, about 4, about 5, about 6, about 7, about 8, about 9, about 10, about 20, about 30, about 40, or about 50 monolayers of PLL. In some embodiments, the polyelectrolyte multilayer comprises from about 2 to about 8 monolayers of PLL. In some embodiments, the polyelectrolyte multilayer comprises from about 2 to about 6 monolayers of PLL. In some embodiments, the polyelectrolyte multilayer comprises from about 3 to about 5 monolayers of PLL.

In some embodiments, the polyelectrolyte multilayer comprises from about 2 to about 50 monolayers of one or more independently selected polyanionic polymers, for example, about 2, about 3, about 4, about 5, about 6, about 7, about 8, about 9, about 10, about 20, about 30, about 40, or about 50 monolayers of the one or more independently selected cationic polymers. In some embodiments, the polyelectrolyte multilayer comprises from about 2 to about 50 monolayers of the one or more independently selected polyanionic polymers. In some embodiments, the polyelectrolyte multilayer comprises from about 2 to about 20 monolayers of the one or more independently selected polyanionic polymers. In some embodiments, the polyelectrolyte multilayer comprises from about 2 to about 10 monolayers of the one or more independently selected polyanionic polymers. In some embodiments, the polyelectrolyte multilayer comprises from about 2 to about 5 monolayers of the one or more independently selected polyanionic polymers. In some embodiments, the polyelectrolyte multilayer comprises from about 5 to about 50 monolayers of the one or more independently selected polyanionic polymers. In some embodiments, the polyelectrolyte multilayer comprises from about 5 to about 20 monolayers of the one or more independently selected polyanionic polymers. In some embodiments, the polyelectrolyte multilayer comprises from about 5 to about 10 monolayers of the one or more independently selected polyanionic polymers. In some embodiments, the polyelectrolyte multilayer comprises from about 10 to about 50 monolayers of the one or more independently selected polyanionic polymers. In some embodiments, the polyelectrolyte multilayer comprises from about 10 to about 20 monolayers of the one or more independently selected polyanionic polymers. In some embodiments, the polyelectrolyte multilayer comprises from about 20 to about 50 monolayers of the one or more independently selected polyanionic polymers.

In some embodiments, the polyelectrolyte multilayer comprises from about 2 to about 50 monolayers of a polyanionic polymer, for example, about 2, about 3, about 4, about 5, about 6, about 7, about 8, about 9, about 10, about 20, about 30, about 40, or about 50 of the one or more independently selected cationic polymers. In some embodiments, the polyelectrolyte multilayer comprises from about 2 to about 50 monolayers of the polyanionic polymer. In some embodiments, the polyelectrolyte multilayer comprises from about 2 to about 20 monolayers of the polyanionic polymer. In some embodiments, the polyelectrolyte multilayer comprises from about 2 to about 10 monolayers of the polyanionic polymer. In some embodiments, the polyelectrolyte multilayer comprises from about 2 to about 5 monolayers of the polyanionic polymer. In some embodiments, the polyelectrolyte multilayer comprises from about 5 to about 50 monolayers of the polyanionic polymer. In some embodiments, the polyelectrolyte multilayer comprises from about 5 to about 20 monolayers of the polyanionic polymer. In some embodiments, the polyelectrolyte multilayer comprises from about 5 to about 10 monolayers of the polyanionic polymer. In some embodiments, the polyelectrolyte multilayer comprises from about 10 to about 50 monolayers of the polyanionic polymer. In some embodiments, the polyelectrolyte multilayer comprises from about 10 to about 20 monolayers of the polyanionic polymer. In some embodiments, the polyelectrolyte multilayer comprises from about 20 to about 50 monolayers of the polyanionic polymer. In some embodiments, the polyelectrolyte multilayer comprises from about 2 to about 50 monolayers of SPS, for example, about 2, about 3, about 4, about 5, about 6, about 7, about 8, about 9, about 10, about 20, about 30, about 40, or about 50 monolayers of SPS. In some embodiments, the polyelectrolyte multilayer comprises from about 2 to about 8 monolayers of SPS. In some embodiments, the polyelectrolyte multilayer comprises from about 2 to about 6 monolayers of SPS. In some embodiments, the polyelectrolyte multilayer comprises from about 3 to about 5 monolayers of SPS.

In some embodiments, the polyelectrolyte multilayer comprises one or more polycationic monolayers and one or more polyanionic monolayers, for example, one or more polycationic monolayers, two or more polycationic monolayers, four or more polycationic monolayers, six or more polycationic monolayers, eight or more polycationic monolayers, or ten or more polycationic monolayers, and one or more polyanionic monolayers, two or more polyanionic monolayers, four or more polyanionic monolayers, six or more polyanionic monolayers, eight or more polyanionic monolayers, or ten or more polyanionic monolayers.

In some embodiments, the polyelectrolyte multilayer comprises from about 1 to about 50 polycationic monolayers and from about 1 to about 50 polyanionic monolayers, for example, about 1 to about 50 polycationic monolayers, about 1 to about 40 polycationic monolayers, about 1 to about 30 polycationic monolayers, about 1 to about 20 polycationic monolayers, about 1 to about 10 polycationic monolayers, about 1 to about 8 polycationic monolayers, about 1 to about 6 polycationic monolayers, about 1 to about 4 polycationic monolayers, about 1 to about 2 polycationic monolayers, about 2 to about 50 polycationic monolayers, about 2 to about 40 polycationic monolayers, about 2 to about 30 polycationic monolayers, about 2 to about 20 polycationic monolayers, about 2 to about 10 polycationic monolayers, about 2 to about 8 polycationic monolayers, about 2 to about 6 polycationic monolayers, about 2 to about 4 polycationic monolayers, about 4 to about 50 polycationic monolayers, about 4 to about 40 polycationic monolayers, about 4 to about 30 polycationic monolayers, about 4 to about 20 polycationic monolayers, about 4 to about 10 polycationic monolayers, about 4 to about 8 polycationic monolayers, about 4 to about 6 polycationic monolayers, about 6 to about 50 polycationic monolayers, about 6 to about 40 polycationic monolayers, about 6 to about 30 polycationic monolayers, about 6 to about 20 polycationic monolayers, about 6 to about 10 polycationic monolayers, about 6 to about 8 polycationic monolayers, about 8 to about 50 polycationic monolayers, about 8 to about 40 polycationic monolayers, about 8 to about 30 polycationic monolayers, about 8 to about 20 polycationic monolayers, about 8 to about 10 polycationic monolayers, about 10 to about 50 polycationic monolayers, about 10 to about 40 polycationic monolayers, about 10 to about 30 polycationic monolayers, about 10 to about 20 polycationic monolayers, 20 to about 50 polycationic monolayers, about 20 to about 40 polycationic monolayers, about 20 to about 30 polycationic monolayers, about 30 to about 50 polycationic monolayers, about 30 to about 40 polycationic monolayers, or about 30 to about 50 polycationic monolayers, and about 1 to about 50 polyanionic monolayers, about 1 to about 40 polyanionic monolayers, about 1 to about 30 polyanionic monolayers, about 1 to about 20 polyanionic monolayers, about 1 to about 10 polyanionic monolayers, about 1 to about 8 polyanionic monolayers, about 1 to about 6 polyanionic monolayers, about 1 to about 4 polyanionic monolayers, about 1 to about 2 polyanionic monolayers, about 2 to about 50 polyanionic monolayers, about 2 to about 40 polyanionic monolayers, about 2 to about 30 polyanionic monolayers, about 2 to about 20 polyanionic monolayers, about 2 to about 10 polyanionic monolayers, about 2 to about 8 polyanionic monolayers, about 2 to about 6 polyanionic monolayers, about 2 to about 4 polyanionic monolayers, about 4 to about 50 polyanionic monolayers, about 4 to about 40 polyanionic monolayers, about 4 to about 30 polyanionic monolayers, about 4 to about 20 polyanionic monolayers, about 4 to about 10 polyanionic monolayers, about 4 to about 8 polyanionic monolayers, about 4 to about 6 polyanionic monolayers, about 6 to about 50 polyanionic monolayers, about 6 to about 40 polyanionic monolayers, about 6 to about 30 polyanionic monolayers, about 6 to about 20 polyanionic monolayers, about 6 to about 10 polyanionic monolayers, about 6 to about 8 polyanionic monolayers, about 8 to about 50 polyanionic monolayers, about 8 to about 40 polyanionic monolayers, about 8 to about 30 polyanionic monolayers, about 8 to about 20 polyanionic monolayers, about 8 to about 10 polyanionic monolayers, about 10 to about 50 polyanionic monolayers, about 10 to about 40 polyanionic monolayers, about 10 to about 30 polyanionic monolayers, about 10 to about 20 polyanionic monolayers, 20 to about 50 polyanionic monolayers, about 20 to about 40 polyanionic monolayers, about 20 to about 30 polyanionic monolayers, about 30 to about 50 polyanionic monolayers, about 30 to about 40 polyanionic monolayers, or about 30 to about 50 polyanionic monolayers, In some embodiments, the polyelectrolyte multilayer comprises about 5 polycationic monolayers and about 4 polyanionic monolayers. In some embodiments, the polyelectrolyte multilayer comprises about 5 monolayers of PLL and about 4 monolayers of SPS.

In some embodiments, the polyelectrolyte multilayer is prepared using sequential deposition of two or more polyionic polymers. In some embodiments, the polyelectrolyte multilayer is prepared using sequential deposition of at least one polycationic polymer and at least one polyanionic polymer. In some embodiments, the polyelectrolyte multilayer is prepared using sequential deposition of one polycationic polymer and one polyanionic polymer.

Another component of the composition includes hyaluronic acid (HA) covalently bonded to the liposome. In some embodiments, the hyaluronic acid is conjugated on the surface of the liposome. In some embodiments, the hyaluronic acid is conjugated on the lipid head group of the liposome. In some embodiments, the liposome comprises a hydrophilic core. In some embodiments, the liposome comprises a lipid component selected from the group consisting of 1,2-dioleoyl-sn-glycero-3-phoshocholine (DOPC), 1,2-dimyristoyl-sn-glycero-3-phosphocholine (DMPC), 1,2-distearoyl-sn-glycero-3-phosphocholine, (DSPC), 1,2-dilauroyl-sn-glycero-3-phosphocholine (DLPC), dipalmitoylphosphatidylcholine (DPPC), and L α-phosphatidylcholine (PC). In some embodiments, the liposome comprises 1,2-dipalmitoyl-sn-glycero-3-phopshoethanolamine (DPPE) and cholesterol (CHOL). In some embodiments, the liposome comprises 1,2-dipalmitoyl-sn-glycero-3-phopshoethanolamine (DPPE) and cholesterol (CHOL), and one or more hyaluronic acids. In some embodiments, the one or more hyaluronic acids are coated on the surface of the DPPE/CHOL liposome. In some embodiments, a hyaluronic acid conjugated liposome provided herein is prepared according to a procedure described herein.

In some embodiments, the liposome further comprises one or more therapeutic agents. In some embodiments, the one or more therapeutic agents are localized in the hydrophilic core or the hydrophobic bilayer of the liposome. In some embodiments, the one or more therapeutic agents are localized in the hydrophilic core of the liposome. In some embodiments, one or more therapeutic agents localized in the hydrophobic core of the liposome. In some embodiments, the one or more therapeutic agents are each independently selected from the group consisting of a chemotherapeutic agent, a silencing RNA, a steroid, an immunosuppressant, an anti-microbial agent, an anti-fungal agent, an anti-inflammatory agent, a gene therapy agent, an anti-angiogenic agent, a stem cell (e.g., for bone marrow transplantation), and a CRISPR/Cas9 component. In some embodiments, at least one of the therapeutic agents is a chemotherapeutic agent or a silencing RNA. In some embodiments, at least one of the therapeutic agents is a chemotherapeutic agent. In some embodiments, at least one of the therapeutic agents is a silencing RNA.

Example anti-angiogenic agents include, but are not limited to a VEGF inhibitor, bevacizumab, thalidomide, itraconazole, carboxyamidotriazole, TNP-470, IFN-α, IL-12, platelet factor-4, suramin, thrombospondin, angiostatin, endostatin, 2-methoxyestradiol, tecogalan, prolactin, linomide, ranibizumab, sorafenib, sunitinib, pazopanib, and everolimus.

Example gene therapy agents include, but are not limited to DNA-based therapy agents, somatic cell gene therapy (SCGT) agents, and germline gene therapy (GTGT) agents.

Example steroids include, but are not limited to, corticosteroids such as cortisone, dexamethasone, hydrocortisone, methylprednisolone, prednisolone, and prednisone.

Example immunosuppressants include, but are not limited to, azathioprine, chlorambucil, cyclophosphamide, cyclosporine, daclizumab, infliximab, methotrexate, and tacrolimus.

Example anti-microbial agents include, but are not limited to, aminoglycosides (e.g., gentamicin, neomycin, and streptomycin), penicillins (e.g., amoxicillin and ampicillin), and macrolides (e.g., erythromycin).

Example anti-fungal agents include, but are not limited to, polyene anti-fungal agents (e.g., amphotericin B and candicidin), imidazole anti-fungal agents (e.g., bifonazole, clotrimazole, and econazole), triazole anti-fungal agents (e.g., albaconazole, efinaconazole, and fluconazole), thiazole anti-fungal agents (e.g., abafungin), allylamine anti-fungal agents (e.g., amorolfin, butenafine, and naftifine), echinocandins (e.g., anidulafungin and caspofungin).

Example anti-inflammatory agents include, but are not limited to, aspirin, choline salicylates, celecoxib, diclofenac potassium, diclofenac sodium, diclofenac sodium with misoprostol, diflunisal, etodolac, fenoprofen, flurbiprofen, ibuprofen, ketoprofen, meclofenamate sodium, mefenamic acid, nabumetone, naproxen, naproxen sodium, oxaprozin, piroxican, rofecoxib, salsalate, sodium salicylate, sulindac, tolmetin sodium, and valdecoxib.

Example chemotherapeutics include, but are not limited to, an alkylating agent (e.g., busulfan, carmustine), an antimetabolite (e.g., 5-fluoro uracil, gemcitabine, methotrexate), an anti-tumor antibiotic (e.g. dactinomycin, doxorubicin, epirubicin), a topoisomerase inhibitor (e.g. topotecan, irinotecan), a mitotic inhibitor (e.g., paclitaxel, ixabepilone, vinblastine, estramustine), a plant alkaloid or a microtubule inhibitor (e.g. docetaxel, irinotecan, etoposide), a DNA linking agent (e.g., carboplatin, cisplatin, oxaliplatin), an immunotherapeutic agent (e.g, rituximab, alemtuzumab, lenalidomide), and a differentiating agent (e.g. tretinoin, bexarotene), cisplatin, doxorubicin, etoposide, irinotecan, topotecan, paclitaxel, docetaxel, tamoxifen, 5-fluorouracil, methotrexate, temozolomide, cyclophosphamide, gefitinib, erlotinib hydrochloride, imatinib mesylate, cytarabine, gemcitabine, uracil mustard, chlormethine, ifosfamide, chlorambucil, pipobroman, triethylenemelamine, busulfan, carmustine, lomustine, streptozocin, dacarbazine, floxuridine, 6-mercaptopurine, 6-thioguanine, fludarabine phosphate, oxaliplatin, pentostatin, vinblastine, vincristine, vindesine, bleomycin, dactinomycin, daunorubicin, epirubicin, idarubicin, deoxycoformycin, mitomycin-C, L-asparaginase, teniposide, testolactone, estramustine, carboplatin, hydroxyurea, amsacrine, procarbazine, mitotane, mitoxantrone, vinorelbine, anastrazole, letrozole, capecitabine, raloxifene, xeloda, vinorelbine, cetuximab, N,N'N'-triethylenethiophosphoramide, altretamine, trastuzumab, fulvestrant, exemestane, and any combination thereof.

Example silencing RNAs include, but are not limited to, small interfering RNA (siRNA) and microRNA (miRNA), and short hairpin RNA (shRNA).

Example CRISPR/Cas9 components include, but are not limited Cre recombinase, TALE, and Cas9 based transcription factors (e.g. to promote genome modification). Additional examples of CRISPR/Cas9 component may be found, e.g., at Zuris et al., Nature Biotechnology, 2015, 33, 73-80.

In some embodiments, the chemotherapeutic agent is selected from the group consisting of an alkylating agent, an anti-metabolite, an anti-tumor antibiotic, a topoisomerase inhibitor, a mitotic inhibitor, a plant alkaloid, a microtubule inhibitor, a DNA linking agent, an immunotherapeutic agent, and a differentiating agent. In some embodiments, the chemotherapeutic agent is an anti-tumor antibiotic. In some embodiments, the chemotherapeutic agent is doxorubicin.

In some embodiments, the liposome further comprises a fluorescently tagged lipid, for example, a fluorescently tagged cholesterol, a fluorescently tagged phosphatidylcholine, a fluorescently tagged sphingolipid, a fluorescently tagged phospholipid, a fluorescently tagged oxidized lipid, and a fluorescently tagged sterol. In some embodiments, the fluorescently tagged lipid is a fluorescently tagged cholesterol.

In some embodiments, the liposome further comprises a targeting moiety. Example targeting moieties include, but are not limited to HER2, ER, and PR, for example, for the treatment of breast cancer; CD44, for example, for the treatment of cancer; and IL-13, for example, for the treatment of glioblastoma. In some embodiments, the targeting moiety is conjugated to the hyaluronic acid. In some embodiments, the targeting moiety is selected from the group consisting of an antibody, a small molecule, a polypeptide, an aptamer, a folate, a transferrin, a glycoprotein, an integrin, and a carbohydrate.

In some embodiments, the one or more hyaluronic acid conjugated liposomes is deposited onto the polyelectrolyte multilayer.

In some embodiments, a composition provided herein further comprises an additional polyelectrolyte multilayer (i.e., a capping layer or a capping multilayer). In some embodiments, the additional polyelectrolyte multilayer forms a capping layer upon the one or more hyaluronic acid conjugated liposome. In some embodiments, the additional polyelectrolyte multilayer is deposited onto the one or more hyaluronic acid conjugated liposomes, wherein the one or more hyaluronic acid conjugated liposomes are located in between the polyelectrolyte multilayer and the additional polyelectrolyte multilayer (i.e., the capping layer).

In some embodiments, the polyelectrolyte multilayer comprises two or more independently selected polyionic polymers, for example, 2 independently selected polyionic polymers, 3 independently selected polyionic polymers, 4 independently selected polyionic polymers, 5 independently selected polyionic polymers, 6 independently selected polyionic polymers, 7 independently selected polyionic polymers, 8 independently selected polyionic polymers, 9 independently selected polyionic polymers, 10 independently selected polyionic polymers, and the like.

In some embodiments, the additional polyelectrolyte multilayer comprises one or more independently selected polycationic polymers. In some embodiments, the additional polyelectrolyte multilayer comprises at least one polycationic polymer. In some embodiments, each of the polycationic polymers is independently selected from the group consisting of poly-D-lysine (PDL), poly-L-lysine (PLL), poly(diallyl dimethylammonium chloride) (PDAC), linear poly(ethylene imine) (LPEI), poly(allyl-amine hydrochloride) (PAH), chitosan (CHI), a poly(β-amino ester), and polyarginine. In some embodiments, the additional polyelectrolyte multilayer comprises one polycationic polymer.

In some embodiments, the additional polyelectrolyte multilayer comprises one or more independently selected polyanionic polymers. In some embodiments, the additional polyelectrolyte multilayer comprises at least one polyanionic polymer. In some embodiments, each of the polyanionic polymers is independently selected from the group consisting of poly(sodium styrene sulfonate) (SPS), poly (anetholesulfonic acid) (PAS), poly(acrylic acid) (PAA), poly(sodium vinylsulfonate) (PVS), graphene oxide (GO), dextran sulfate, collagen, and hyaluronic acid (HA). In some embodiments, each the additional polyelectrolyte multilayer comprises one polyanionic polymer.

In some embodiments, at least one of the polycationic polymers is poly-L-lysine (PLL) and at least one of the polyanionic polymers is poly(sodium styrene sulfonate) (SPS).

In some embodiments, the additional polyelectrolyte multilayer comprises from about 2 to about 10 monolayers of one or more independently selected polycationic polymers, for example, about 2, about 3, about 4, about 5, about 6, about 7, about 8, about 9, or about 10 monolayers one or more independently selected cationic polymers. In some embodiments, the additional polyelectrolyte multilayer comprises from about 2 to about 8 monolayers of one or more independently selected polycationic polymers. In some embodiments, the additional polyelectrolyte multilayer comprises from about 2 to about 6 monolayers of one or more independently selected polycationic polymers. In some embodiments, the additional polyelectrolyte multilayer comprises from about 3 to about 5 monolayers of one or more independently selected polycationic polymers.

In some embodiments, the additional polyelectrolyte multilayer comprises from about 2 to about 10 monolayers of a polycationic polymer, for example, about 2, about 3, about 4, about 5, about 6, about 7, about 8, about 9, or about 10 monolayers one or more independently selected cationic polymers. In some embodiments, the additional polyelectrolyte multilayer comprises from about 2 to about 8 monolayers of a polycationic polymer. In some embodiments, the additional polyelectrolyte multilayer comprises from about 2 to about 6 monolayers of a polycationic polymer. In some embodiments, the additional polyelectrolyte multilayer comprises from about 3 to about 5 monolayers of a polycationic polymer.

In some embodiments, the additional polyelectrolyte multilayer comprises from about 2 to about 10 monolayers of PLL, about 2, about 3, about 4, about 5, about 6, about 7, about 8, about 9, or about 10 monolayers of PLL. In some embodiments, the additional polyelectrolyte multilayer comprises from about 2 to about 8 monolayers of PLL. In some embodiments, the additional polyelectrolyte multilayer comprises from about 2 to about 6 monolayers of PLL. In some embodiments, the additional polyelectrolyte multilayer comprises from about 3 to about 5 monolayers of PLL.

In some embodiments, the additional polyelectrolyte multilayer comprises from about 2 to about 10 monolayers of one or more independently selected polyanionic polymers, for example, about 2, about 3, about 4, about 5, about 6, about 7, about 8, about 9, or about 10 monolayers one or more independently selected cationic polymers. In some embodiments, the additional polyelectrolyte multilayer comprises from about 2 to about 8 monolayers of one or more independently selected polyanionic polymers. In some embodiments, the additional polyelectrolyte multilayer comprises from about 2 to about 6 monolayers of one or more independently selected polyanionic polymers. In some embodiments, the additional polyelectrolyte multilayer comprises from about 3 to about 5 monolayers of one or more independently selected polyanionic polymers.

In some embodiments, the additional polyelectrolyte multilayer comprises from about 2 to about 10 monolayers of a polyanionic polymer, for example, about 2, about 3, about 4, about 5, about 6, about 7, about 8, about 9, or about 10 monolayers one or more independently selected cationic polymers. In some embodiments, the additional polyelectrolyte multilayer comprises from about 2 to about 8 monolayers of a polyanionic polymer. In some embodiments, the additional polyelectrolyte multilayer comprises from about 2 to about 6 monolayers of a polyanionic polymer. In some embodiments, the additional polyelectrolyte multilayer comprises from about 3 to about 5 monolayers of a polyanionic polymer.

In some embodiments, the additional polyelectrolyte multilayer comprises from about 2 to about 10 monolayers of SPS, for example, about 2, about 3, about 4, about 5, about 6, about 7, about 8, about 9, or about 10 monolayers of SPS. In some embodiments, the additional polyelectrolyte multilayer comprises from about 2 to about 8 monolayers of SPS. In some embodiments, the additional polyelectrolyte multilayer comprises from about 2 to about 6 monolayers of SPS. In some embodiments, the additional polyelectrolyte multilayer comprises from about 3 to about 5 monolayers of SPS.

In some embodiments, the additional polyelectrolyte multilayer is prepared using sequential deposition of two or more polyionic polymers. In some embodiments, the additional polyelectrolyte multilayer is prepared using sequential deposition of at least one polycationic polymer and at least one polyanionic polymer. In some embodiments, the additional polyelectrolyte multilayer is prepared using sequential deposition of one polycationic polymer and one polyanionic polymer.

In some embodiments, the additional polyelectrolyte multilayer is deposited onto the one or more hyaluronic acid conjugated liposomes. In some embodiments, the additional polyelectrolyte multilayer forms a capping layer upon the one or more hyaluronic acid conjugated liposome. In some embodiments, the additional polyelectrolyte multilayer is deposited onto the one or more hyaluronic acid conjugated liposomes, wherein the one or more hyaluronic acid conjugated liposomes are located in between the polyelectrolyte multilayer and the additional polyelectrolyte multilayer (i.e., the capping layer).

In some embodiments:
i) one or more hyaluronic acid conjugated liposomes are deposited onto the polyelectrolyte multilayer; and
ii) the additional polyelectrolyte multilayer is subsequently deposited onto the one or more hyaluronic acid conjugated liposomes.

In some embodiments, a composition provided herein is deposited onto a substrate. In some embodiments, the composition is coated onto at least one surface the substrate. In some embodiments, the substrate is selected from the group consisting of a medical device, a tablet, a capsule, a bandage, a gel, a nanoparticle, an oxygen plasma treated surface, a sterile glass slide, a sterile glass plate, a tissue culture plate, and a cell culture plate. In some embodiments, the medical device is selected from the group consisting of a stent, a catheter, a syringe, a needle, a microneedle, a medical implant, a metal rod, a cardiac pace maker, a surgical staple, a surgical suture, a needle, a balloon, a bandage, a wound graft, and a cartilage substitute. In some embodiments, a composition provided herein is coated onto at least one surface of a device. In some embodiments, a composition provided herein is coated onto at least one surface of a medical device.

In some embodiments:
the one or more hyaluronic acid conjugated liposomes further comprise one or more therapeutic agents; and
the polyelectrolyte multilayer comprises two more independently selected polyionic polymers.

In some embodiments:
the one or more hyaluronic acid conjugated liposomes further comprise one or more therapeutic agents; and
the polyelectrolyte multilayer comprises one or more independently selected polycationic polymers.

In some embodiments:
the one or more hyaluronic acid conjugated liposomes further comprise one or more therapeutic agents;
the polyelectrolyte multilayer comprises one or more independently selected polycationic polymers; and
each of the polycationic polymers is independently selected from the group consisting of poly-D-lysine (PDL), poly-L-lysine (PLL), poly(diallyl dimethylammonium chloride) (PDAC), linear poly(ethylene imine) (LPEI), poly (allyl-amine hydrochloride) (PAH), chitosan (CHI), a poly (β-amino ester), and polyarginine.

In some embodiments:
the one or more hyaluronic acid conjugated liposomes further comprise one or more therapeutic agents;
the polyelectrolyte multilayer comprises a polycationic polymer selected from the group consisting of poly-D-lysine (PDL), poly-L-lysine (PLL), poly(diallyl dimethylammonium chloride) (PDAC), linear poly(ethylene imine) (LPEI), poly(allyl-amine hydrochloride) (PAH), chitosan (CHI), a poly(β-amino ester), and polyarginine.

In some embodiments:
the one or more hyaluronic acid conjugated liposomes further comprise one or more therapeutic agents;
the polyelectrolyte multilayer comprises one or more independently selected polycationic polymers; and the composition further comprises a substrate.

In some embodiments:
the one or more hyaluronic acid conjugated liposomes further comprise one or more therapeutic agents;
the polyelectrolyte multilayer comprises one or more independently selected polycationic polymers;
each of the polycationic polymers is independently selected from the group consisting of poly-D-lysine (PDL), poly-L-lysine (PLL), poly(diallyl dimethylammonium chloride) (PDAC), linear poly(ethylene imine) (LPEI), poly (allyl-amine hydrochloride) (PAH), chitosan (CHI), a poly (β-amino ester), and polyarginine; and the composition further comprises a substrate.

In some embodiments:
the one or more hyaluronic acid conjugated liposomes further comprise one or more therapeutic agents;
the polyelectrolyte multilayer comprises a polycationic polymer selected from the group consisting of poly-D-lysine (PDL), poly-L-lysine (PLL), poly(diallyl dimethylammonium chloride) (PDAC), linear poly(ethylene imine) (LPEI), poly(allyl-amine hydrochloride) (PAH), chitosan (CHI), a poly(β-amino ester), and polyarginine; and the composition further comprises a substrate.

In some embodiments:
the one or more hyaluronic acid conjugated liposomes further comprise one or more therapeutic agents; and
the polyelectrolyte multilayer comprises one or more independently selected polyanionic polymers.

In some embodiments:
the one or more hyaluronic acid conjugated liposomes further comprise one or more therapeutic agents;
the polyelectrolyte multilayer comprises one or more independently selected polanionic polymers; and
each of the polyanionic polymers is independently selected from the group consisting of poly(sodium styrene sulfonate) (SPS), poly(anetholesulfonic acid) (PAS), poly(acrylic acid) (PAA), poly(sodium vinylsulfonate) (PVS), graphene oxide (GO), dextran sulfate, collagen, and hyaluronic acid (HA).

In some embodiments:
the one or more hyaluronic acid conjugated liposomes further comprise one or more therapeutic agents;
the polyelectrolyte multilayer comprises a polyanionic polymer selected from the group consisting of poly(sodium styrene sulfonate) (SPS), poly(anetholesulfonic acid) (PAS), poly(acrylic acid) (PAA), poly(sodium vinylsulfonate) (PVS), graphene oxide (GO), dextran sulfate, collagen, and hyaluronic acid (HA).

In some embodiments:
the one or more hyaluronic acid conjugated liposomes further comprise one or more therapeutic agents;
the polyelectrolyte multilayer comprises one or more independently selected polyanionic polymers; and the composition further comprises a substrate.

In some embodiments:
the one or more hyaluronic acid conjugated liposomes further comprise one or more therapeutic agents;
the polyelectrolyte multilayer comprises one or more independently selected polanionic polymers;
each of the polyanionic polymers is independently selected from the group consisting of poly(sodium styrene sulfonate) (SPS), poly(anetholesulfonic acid) (PAS), poly(acrylic acid) (PAA), poly(sodium vinylsulfonate) (PVS), graphene oxide (GO), dextran sulfate, collagen, and hyaluronic acid (HA); and the composition further comprises a substrate.

In some embodiments:
the one or more hyaluronic acid conjugated liposomes further comprise one or more therapeutic agents;
the polyelectrolyte multilayer comprises a polyanionic polymer selected from the group consisting of poly(sodium styrene sulfonate) (SPS), poly(anetholesulfonic acid) (PAS), poly(acrylic acid) (PAA), poly(sodium vinylsulfonate) (PVS), graphene oxide (GO), dextran sulfate, collagen, and hyaluronic acid (HA); and the composition further comprises a substrate.

In some embodiments:
the one or more hyaluronic acid conjugated liposomes further comprise one or more therapeutic agents;
the polyelectrolyte multilayer comprises one or more independently selected polycationic polymers and one or more independently selected polyanionic polymers;
wherein each of the polycationic polymers is independently selected from the group consisting of poly-D-lysine (PDL), poly-L-lysine (PLL), poly(diallyl dimethylammonium chloride) (PDAC), linear poly(ethylene imine) (LPEI), poly(allyl-amine hydrochloride) (PAH), chitosan (CHI), a poly(β-amino ester), and polyarginine; and
each of the polyanionic polymers is independently selected from the group consisting of poly(sodium styrene sulfonate) (SPS), poly(anetholesulfonic acid) (PAS), poly(acrylic acid) (PAA), poly(sodium vinylsulfonate) (PVS), graphene oxide (GO), dextran sulfate, collagen, and hyaluronic acid (HA).

In some embodiments:
the one or more hyaluronic acid conjugated liposomes further comprise one or more therapeutic agents;
the polyelectrolyte multilayer comprises one polycationic polymer and one polyanionic polymer;
wherein the polycationic polymer is selected from the group consisting of poly-D-lysine (PDL), poly-L-lysine (PLL), poly(diallyl dimethylammonium chloride) (PDAC), linear poly(ethylene imine) (LPEI), poly(allyl-amine hydrochloride) (PAH), chitosan (CHI), a poly(β-amino ester), and polyarginine; and
the polyanionic polymer is selected from the group consisting of poly(sodium styrene sulfonate) (SPS), poly(anetholesulfonic acid) (PAS), poly(acrylic acid) (PAA), poly(sodium vinylsulfonate) (PVS), graphene oxide (GO), dextran sulfate, collagen, and hyaluronic acid (HA).

In some embodiments:
the one or more hyaluronic acid conjugated liposomes further comprise one or more therapeutic agents;
the polyelectrolyte multilayer comprises one or more independently selected polycationic polymers and one or more independently selected polyanionic polymers;
wherein each of the polycationic polymers is independently selected from the group consisting of poly-D-lysine (PDL), poly-L-lysine (PLL), poly(diallyl dimethylammonium chloride) (PDAC), linear poly(ethylene imine) (LPEI), poly(allyl-amine hydrochloride) (PAH), chitosan (CHI), a poly(β-amino ester), and polyarginine;
each of the polyanionic polymers is independently selected from the group consisting of poly(sodium styrene sulfonate) (SPS), poly(anetholesulfonic acid) (PAS), poly(acrylic acid) (PAA), poly(sodium vinylsulfonate) (PVS), graphene oxide (GO), dextran sulfate, collagen, and hyaluronic acid (HA); and the composition further comprises a substrate.

In some embodiments:
the one or more hyaluronic acid conjugated liposomes further comprise one or more therapeutic agents;
the polyelectrolyte multilayer comprises one polycationic polymer and one polyanionic polymer;
wherein the polycationic polymer is selected from the group consisting of poly-D-lysine (PDL), poly-L-lysine (PLL), poly(diallyl dimethylammonium chloride) (PDAC), linear poly(ethylene imine) (LPEI), poly(allyl-amine hydrochloride) (PAH), chitosan (CHI), a poly(β-amino ester), and polyarginine;
the polyanionic polymer is selected from the group consisting of poly(sodium styrene sulfonate) (SPS), poly(anetholesulfonic acid) (PAS), poly(acrylic acid) (PAA), poly(sodium vinylsulfonate) (PVS), graphene oxide (GO), dextran sulfate, collagen, and hyaluronic acid (HA); and the composition further comprises a substrate.

In some embodiments:
the one or more hyaluronic acid conjugated liposomes further comprise one or more therapeutic agents;
the polyelectrolyte multilayer comprises one or more independently selected polycationic polymers and one or more independently selected polyanionic polymers;
wherein each of the polycationic polymers is independently selected from the group consisting of poly-D-lysine (PDL), poly-L-lysine (PLL), poly(diallyl dimethylammonium chloride) (PDAC), linear poly(ethylene imine) (LPEI), poly(allyl-amine hydrochloride) (PAH), chitosan (CHI), a poly(β-amino ester), and polyarginine;

each of the polyanionic polymers is independently selected from the group consisting of poly(sodium styrene sulfonate) (SPS), poly(anetholesulfonic acid) (PAS), poly(acrylic acid) (PAA), poly(sodium vinylsulfonate) (PVS), graphene oxide (GO), dextran sulfate, collagen, and hyaluronic acid (HA);

wherein at least one of the polycationic polymers is poly-L-lysine (PLL) and at least one of the polyanionic polymers is poly(sodium styrene sulfonate) (SPS); and the composition further comprises a substrate.

In some embodiments:

the one or more hyaluronic acid conjugated liposomes further comprise one or more therapeutic agents;

the polyelectrolyte multilayer comprises one polycationic polymer and one polyanionic polymer;

wherein the polycationic polymer is selected from the group consisting of poly-D-lysine (PDL), poly-L-lysine (PLL), poly(diallyl dimethylammonium chloride) (PDAC), linear poly(ethylene imine) (LPEI), poly(allyl-amine hydrochloride) (PAH), chitosan (CHI), a poly(β-amino ester), and polyarginine;

the polyanionic polymer is selected from the group consisting of poly(sodium styrene sulfonate) (SPS), poly(anetholesulfonic acid) (PAS), poly(acrylic acid) (PAA), poly(sodium vinylsulfonate) (PVS), graphene oxide (GO), dextran sulfate, collagen, and hyaluronic acid (HA); and the composition further comprises a substrate.

In some embodiments:

the one or more hyaluronic acid conjugated liposomes further comprise one or more therapeutic agents;

the polyelectrolyte multilayer comprises one polycationic polymer and one polyanionic polymer;

wherein the polycationic polymer is selected from the group consisting of poly-D-lysine (PDL), poly-L-lysine (PLL), poly(diallyl dimethylammonium chloride) (PDAC), linear poly(ethylene imine) (LPEI), poly(allyl-amine hydrochloride) (PAH), chitosan (CHI), a poly(β-amino ester), and polyarginine;

the polyanionic polymer is selected from the group consisting of poly(sodium styrene sulfonate) (SPS), poly(anetholesulfonic acid) (PAS), poly(acrylic acid) (PAA), poly(sodium vinylsulfonate) (PVS), graphene oxide (GO), dextran sulfate, collagen, and hyaluronic acid (HA);

the additional polyelectrolyte multilayer comprises one or more independently selected polycationic polymers and one or more independently selected polyanionic polymers;

and the composition further comprises a substrate.

In some embodiments:

the one or more hyaluronic acid conjugated liposomes further comprise one or more therapeutic agents;

the polyelectrolyte multilayer comprises one polycationic polymer and one polyanionic polymer;

wherein the polycationic polymer is selected from the group consisting of poly-D-lysine (PDL), poly-L-lysine (PLL), poly(diallyl dimethylammonium chloride) (PDAC), linear poly(ethylene imine) (LPEI), poly(allyl-amine hydrochloride) (PAH), chitosan (CHI), a poly(β-amino ester), and polyarginine;

the polyanionic polymer is selected from the group consisting of poly(sodium styrene sulfonate) (SPS), poly(anetholesulfonic acid) (PAS), poly(acrylic acid) (PAA), poly(sodium vinylsulfonate) (PVS), graphene oxide (GO), dextran sulfate, collagen, and hyaluronic acid (HA);

the additional polyelectrolyte multilayer comprises one or more independently selected polycationic polymers and one or more independently selected polyanionic polymers wherein at least one of the polycationic polymers is poly-L-lysine (PLL) and at least one of the polyanionic polymers is poly(sodium styrene sulfonate) (SPS);

and the composition further comprises a substrate.

Preparation of Compositions

The present application further provides methods of preparing the compositions provided herein. In some embodiments, the method comprises:

i) sequentially depositing two or more polyionic polymers to form the polyelectrolyte multilayer; and ii) depositing the one or more hyaluronic acid conjugated liposomes onto the polyelectrolyte multilayer. In some embodiments, the sequential deposition of step i) is performed in solution. In some embodiments, the sequential deposition of step i) is performed in an aqueous solution. In some embodiments, the sequential deposition of step i) is performed in deionized water.

In some embodiments, the deposition of step ii) is performed in solution. In some embodiments, the deposition of step ii) is performed in a buffered aqueous solution. In some embodiments, the pH of the buffered aqueous solution is from about 7.5 to about 9. In some embodiments, the buffered aqueous solution further comprises a carboxyl-amine coupling agent. In some embodiments, the carboxyl-amine coupling agent is selected from the group consisting of N,N'-dicyclohexylcarbodiimide (DCC), N,N'-diisopropylcarbodiimide (DIC), and 1-ethyl-3-(3-dimethylaminopropyl)carbodiimide (EDAC). In some embodiments, the carboxyl-amine coupling agent is 1-ethyl-3-(3-dimethylaminopropyl)carbodiimide (EDAC).

In some embodiments, at least one of the polyionic polymers is a polycationic polymer provided herein and at least one of the polyionic polymers is polyanionic polymer provided herein. In some embodiments, at least one of the polycationic polymers is poly-L-lysine (PLL) and at least one of the polyanionic polymers is poly(sodium styrene sulfonate) (SPS).

In some embodiments, step ii) comprises contacting the one or more hyaluronic acid conjugated liposomes with the polyelectrolyte multilayer at about room temperature.

The present application further provides a method of preparing a composition provided herein, the method comprising:

i) sequentially depositing two or more polyionic polymers to form the polyelectrolyte multilayer;

ii) depositing the one or more hyaluronic acid conjugated liposomes onto the polyelectrolyte multilayer; and iii) depositing the additional polyelectrolyte multilayer onto the one or more hyaluronic acid conjugated liposomes.

In some embodiments, the sequential deposition of steps i) is performed in solution. In some embodiments, the sequential deposition of step i) is performed in an aqueous solution. In some embodiments, the sequential deposition of step i) is performed in deionized water.

In some embodiments, the deposition of step ii) is performed in solution. In some embodiments, the deposition of step ii) is performed in a buffered aqueous solution. In some embodiments, the pH of the buffered aqueous solution is from about 7.5 to about 9. In some embodiments, the buffered aqueous solution further comprises a carboxyl-amine coupling agent. In some embodiments, the carboxyl-amine coupling agent is selected from the group consisting of N,N'-dicyclohexylcarbodiimide (DCC), N,N'-diisopropylcarbodiimide (DIC), and 1-ethyl-3-(3-dimethylaminopropyl)carbodiimide (EDAC). In some embodiments, the carboxyl-amine coupling agent is 1-ethyl-3-(3-dimethylaminopropyl)carbodiimide (EDAC).

In some embodiments, step ii) comprises contacting the one or more hyaluronic acid conjugated liposomes with the polyelectrolyte multilayer at about room temperature.

In some embodiments, the contacting is performed from about 1 to about 10 hours, for example, from about 1 to about 10 hours, from about 1 to about 8 hours, from about 1 to about 6 hours, from about 1 to about 4 hours, from about 1 to about 2 hours, from about 1 to about 1.5 hours, from about 1.5 to about 10 hours, from about 1.5 to about 8 hours, from about 1.5 to about 6 hours, from about 1.5 to about 4 hours, from about 1.5 to about 2 hours, from about 2 to about 10 hours, from about 2 to about 8 hours, from about 2 to about 6 hours, from about 2 to about 4 hours, from about 4 to about 10 hours, from about 4 to about 8 hours, from about 4 to about 6 hours, from about 6 to about 10 hours, from about 6 to about 8 hours, or from about 8 to about 10 hours. In some embodiments, the contacting is performed from about 2 to about 5 hours.

In some embodiments, at least one of the polyionic polymers is a polycationic polymer as described herein and at least one of the polyionic polymers is polyanionic polymer as described herein.

Methods of Use & Combination Therapy

The present application further provides methods of treating a disease or disorder in a subject in need thereof. As used herein, the term "subject" refers to any animal, including mammals, for example, mice, rats, other rodents, rabbits, dogs, cats, swine, cattle, sheep, horses, primates, and humans. In some embodiments, the subject is a human. In some embodiments, the method comprises administering to the subject a composition provided herein, wherein the composition comprises one or more therapeutic agents. In some embodiments, the administration comprising administering a therapeutically effective amount of the one or more therapeutic agents.

As used herein, the term "treating" or "treatment" refers to one or more of (1) inhibiting the disease; for example, inhibiting a disease, condition or disorder in an individual who is experiencing or displaying the pathology or symptomatology of the disease, condition or disorder (i.e., arresting further development of the pathology and/or symptomatology); and (2) ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease or reducing or alleviating one or more symptoms of the disease.

In some embodiments, the disease or disorder is a cancer, an autoimmune disease or disorder, or an autoimmune disease or disorder. In some embodiments, the disease is a cancer.

In some embodiments, the cancer is selected from the group consisting of pancreatic cancer, bladder cancer, brain cancer (e.g., glioblastoma), breast cancer, colon cancer, endometrial cancer, gastrointestinal cancer, a hematological cancer, liver cancer, lung cancer, prostate cancer, skin cancer, stomach cancer, and renal cancer. In some embodiments, the cancer is breast cancer. In some embodiments, the cancer is brain cancer. In some embodiments, the cancer is glioblastoma.

In some embodiments, the hematological cancer is selected from the group consisting of leukemia and lymphoma.

In some embodiments, the leukemia is selected from the group consisting of acute myeloid leukemia (AML), chronic lymphocytic leukemia (CLL), chronic myelogenous leukemia (CML), multiple myeloma, hairy cell leukemia, T-cell actute lymphoblasic leukemia (T-ALL), and large granular lymphocytic leukemia.

In some embodiments, the lymphoma is selected from the group consisting of small lymphocytic lymphoma, cutaneous T-cell lymphoma, Burkitt's lymphoma, peripheral T-cell lymphoma, follicular lymphoma, lymphoplasmacytic lymphoma, extranodal marginal zone lymphoma, mucosa-associated lymphatic tissue (MALT) lymphoma, anaplastic large cell lymphoma (ALCL), Mantle cell lymphoma, Hodgkin's lymphoma, non-Hodgkin's lymphoma, and lymphoblastic lymphoma.

Example inflammatory diseases include arthritis, rheumatoid arthritis, vasculitis, inflammatory bowel disease, glomerulonephritis, sarcoidosis, inflammation of the eye, inflammation of the skin, inflammation of an organ (e.g., brain, liver, pancreas, heart, lung, stomach, spleen, and the like), inflammation of the respiratory tract, inflammation of the digestive tract, muscular inflammation, inflammation of the lymphatic system, and the like. In some embodiments, the disease is atherosclerosis. In some embodiments, the disease comprises atherosclerotic plaque.

Example autoimmune diseases include, but are not limited to, autoimmune diseases of the heart (e.g., myocarditis, postmyocardial infarction syndrome, postpericardiotomy syndrome, subacute bacterial endocarditis), autoimmune diseases of the kidney (e.g., anti-glomerular basement membrane nephritis, lupus nephritis), autoimmune diseases of the liver (e.g., autoimmune hepatitis, primary biliary cirrhosis), autoimmune diseases of the lung (e.g., antisynthetase syndrome), autoimmune diseases of the skin (e.g., psoriasis, systemic scleroderma), pancreatitis, diabetes mellitus type 1, Graves' disease, Sjorgren's syndrome, celiac disease, Crohn's disease, ulcerative colitis, Lyme disease, Guillain-Barré syndrome, and multiple sclerosis.

The present application further provides a method for controlled release of one or more therapeutic agents, comprising administering to a subject a composition provided herein, wherein the composition further comprises the one or more therapeutic agents. In some embodiments, the method is performed ex vivo. In some embodiments, the method is performed in vivo.

The present application further provides a method for delayed release of one or more therapeutic agents, comprising administering to a subject a composition provided herein, wherein the composition further comprises the one or more therapeutic agents. In some embodiments, the method is performed ex vivo. In some embodiments, the method is performed in vivo.

The present application further provides a method of treating a disease or disorder in a subject in need thereof, comprising administering to the subject a composition provided herein, wherein the composition releases the one or more therapeutic agents for treatment of the disease. In some embodiments, the release is a controlled release. As used herein, the term "controlled release" refers to the release of a therapeutic agent over time or in response to a stimulus wherein the release maintains drug levels within an appropriate dosage level. In some embodiments, the controlled release is a timed release (i.e., the one or more therapeutic agents are released after a period of time) or a sustained release (i.e., the one or more therapeutic agents are gradually released over a period of time within an appropriate, non-toxic dosage level). In some embodiments, the release is a delayed release. As used herein, the term "delayed release" refers to a release that occurs at a time substantially later than administration of the one or more therapeutic agents (i.e., the release is not immediate).

In some embodiments, the administration comprises contacting a diseased cell with a composition provided herein. In some embodiments, the contacting is performed ex vivo. In some embodiments, the contacting is performed in vivo.

The present application further provides a method of treating cancer, comprising administering to a subject in need thereof a composition provided herein, wherein the composition further comprises a chemotherapeutic agent. Example chemotherapeutic agents include, but are not limited to, cisplatin, doxorubicin, taxol, etoposide, irinotecan, topotecan, paclitaxel, docetaxel, epothilones, tamoxifen, 5-fluorouracil, methotrexate, temozolomide, cyclophosphamide, SCH 66336, R115777, L778,123, BMS 214662, gefitinib, erlotinib hydrochloride, antibodies to EGFR, imatinib mesylate, intron, ara-C, gemcitabine, uracil mustard, chlormethine, ifosfamide, melphalan, chlorambucil, pipobroman, triethylenemelamine, triethylenethiophosphoramine, busulfan, carmustine, lomustine, streptozocin, dacarbazine, floxuridine, cytarabine, 6-mercaptopurine, 6-thioguanine, fludarabine phosphate, oxaliplatin, folinic acid, pentostatin, vinblastine, vincristine, vindesine, bleomycin, dactinomycin, daunorubicin, doxorubicin, epirubicin, idarubicin, mithramycin, deoxycoformycin, mitomycin-C, L-asparaginase, teniposide, 17α-ethinylestradiol, diethylstilbestrol, testosterone, prednisone, fluoxymesterone, dromostanolone propionate, testolactone, megestrol acetate, methylprednisolone, methyltestosterone, prednisolone, triamcinolone, chlorotrianisene, hydroxyprogesterone, aminoglutethimide, estramustine, medroxyprogesteroneacetate, leuprolide, flutamide, toremifene, goserelin, carboplatin, hydroxyurea, amsacrine, procarbazine, mitotane, mitoxantrone, levamisole, vinorelbine, anastrazole, letrozole, capecitabine, reloxafine, hexamethylmelamine, bevacizumab, bexxar, velcade, zevalin, trisenox, xeloda, vinorelbine, porfimer, erbitux, liposomal, thiotepa, altretamine, melphalan, trastuzumab, fulvestrant, exemestane, ifosfamide, rituximab, C225, alemtuzumab, clofarabine, cladribine, aphidicolin, sunitinib, dasatinib, tezacitabine, Sml1, triapine, didox, trimidox, amidox, 3-AP, MDL-101,731, bendamustine, ofatumumab, and GS-1101 (also known as CAL-101). In some embodiments, the chemotherapeutic agent is doxorubicin. In some embodiments, the chemotherapeutic agent comprises one or more oncolytic virus strains or particles.

The present application further provides a method of treating an inflammatory disease or disorder, comprising administering to a subject in need thereof a composition provided herein, wherein the composition further comprises an anti-inflammatory agent. Example anti-inflammatory agents include, but are not limited to, aspirin, choline salicylates, celecoxib, diclofenac potassium, diclofenac sodium, diclofenac sodium with misoprostol, diflunisal, etodolac, fenoprofen, flurbiprofen, ibuprofen, ketoprofen, meclofenamate sodium, mefenamic acid, nabumetone, naproxen, naproxen sodium, oxaprozin, piroxican, rofecoxib, salsalate, sodium salicylate, sulindac, tolmetin sodium, and valdecoxib. In some embodiments, the anti-inflammatory agent comprises one or more virus strains or particles useful as a vaccine for treating the inflammatory disease or disorder. In some embodiments, the anti-inflammatory agent comprises one or more virus strains or particles useful as a vaccine for treating a cardiovascular disease.

The present application further provides a method of treating an autoimmune disease or disorder, comprising administering to a subject in need thereof a composition provided herein, wherein the composition further comprises an immunosuppressant agent. Example immunosuppressant agents include, but are not limited to, azathioprine, chlorambucil, cyclophosphamide, cyclosporine, daclizumab, infliximab, methotrexate, and tacrolimus. In some embodiments, the immunosuppressant agent comprises one or more virus strains or particles useful as a vaccine for treating the autoimmune disease or disorder. In some embodiments, the immunosuppressant agent comprises one or more virus strains or particles useful as a vaccine for treating diabetes (e.g., type 2 diabetes).

In some embodiments, the methods provided herein further comprise administering one or more additional therapeutic agents or a radiation therapy. Example therapeutic agents for use in combination therapy include, for example, therapeutic agents provided herein and anesthetics (e.g. for use in combination with a surgical procedure). Example anesthetics include, but are not limited to local anesthetics such as lidocaine, procain, and ropivacaine.

In some embodiments, the one or more additional therapeutic agents are administered simultaneously with a composition provided herein. In some embodiments, the one or more additional therapeutic agents are administered after administration of a composition provided herein. In some embodiments, the one or more additional therapeutic agents are administered prior to administration of a composition provided herein.

Devices and Pharmaceutical Compositions

The present application further provides a device comprising a composition provided herein. In some embodiments, composition is formulated as a coating. In some embodiments, the device is coated in a composition provided herein. In some embodiments, at least one surface of the device is coated in a composition provided herein. In some embodiments, the present application provides a coated device (e.g., a coated medical device), wherein the coating comprises a composition provided herein. In some embodiments, the composition further comprises one or more therapeutic agents.

In some embodiments, the device is a medical device. In some embodiments, the medical device is selected from the group consisting of a stent, a catheter, a syringe, a needle, a microneedle, a medical implant, a metal rod, a cardiac pace maker, a surgical staple, a surgical suture, a needle, a balloon, a bandage, a wound graft, and a cartilage substitute.

The present application further provides a pharmaceutical composition comprising a composition provided herein and at least one pharmaceutically acceptable carrier. The pharmaceutical composition provided herein can be prepared as described herein or elsewhere, and can be administered by a variety of routes, depending upon whether local or systemic treatment is desired and upon the area to be treated. Administration may be, for example, oral administration. In some embodiments, the pharmaceutical composition is formulated as a tablet, a pill, a powder, a suspension, an emulsion, or a capsule (e.g., a soft or hard gelatin capsule).

The compositions provided herein comprising one or more therapeutic agents can be effective over a wide dosage range and are generally administered in a therapeutically effective amount. It will be understood, however, that the amount of a composition comprising the one or more therapeutic agents actually administered and the schedule of administration will usually be determined by a physician, according to the relevant circumstances, including the condition to be treated, the chosen route of administration, the actual therapeutic agent(s) administered, the age, weight, and response of the individual subject, the severity of the subject's symptoms, and the like.

The present application further provides a tablet coated with a composition provided herein. In some embodiments, the tablet further comprises one or more additional therapeutic agents. In some embodiments, the tablet is coated with a composition provided herein, wherein the composition further comprises one therapeutic agent. In some embodiments, the composition and the tablet each comprise one or more independently selected therapeutic agent. In some embodiments, the composition and tablet each comprise one or more of the same therapeutic agent. In some embodiments, the composition and tablet each comprise one or more different therapeutic agents.

In some embodiments, the tablet is formulated as a pharmaceutical carrier. The tablets provided herein can be coated (e.g., with a composition provided herein) or otherwise compounded to provide a dosage form affording the advantage of prolonged action. For example, the tablet can comprise an inner dosage and an outer dosage component, the latter being in the form of an envelope over the former. The two components can be further separated by an enteric layer which serves to resist disintegration in the stomach and permit the inner component to pass intact into the duodenum or to be delayed in release. Examples of materials that can be used for enteric layers or coatings, include, but are not limited to, polymeric acids and mixtures of polymeric acids with such materials as shellac, cetyl alcohol, and cellulose acetate.

When employed as pharmaceuticals, the compositions provided herein can be administered in the form of pharmaceutical compositions; thus, the methods described herein can include administering pharmaceutical compositions provided herein.

EXAMPLES

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results.
General Materials and Methods For polyelectrolyte multilayer (PEM) fabrication, poly-L-lysine (PLL) hydrochloride with a molecular weight greater than 30,000 Da and poly(sodium styrene sulfonate) (SPS) with a molecular weight of ~70,000 Da were purchased from Sigma Aldrich (St. Louis, Mo., USA). For liposome assembly and nanoparticle surface conjugation, hyaluronic acid (HA) with a molecular weight of 1.65 MDa, 1,2-dipalmitoyl-sn-glycero-3-phopshoethanolamine (DPPE), cholesterol (CHOL), and 1-ethyl-3-(3-dimethylaminopropyl) carbomiide (EDAC) were purchased from Sigma. Additionally, L α-phosphatidylcholine (PC) and Top Fluor fluorescently tagged cholesterol were purchased from Avanti Polar Lipids (Alabaster, Ala., USA). For Capillary Force Lithography (CFL), PDMS elastomer (SYLGARD 184 Silicone Elastomer Base) and PDMS cross linker (SYLGARD 184 Silicone Elastomer Curing Agent) were purchased from Dow Corning Corporation (Midland, Mich., USA). Fluorosilane (Trichloro(3,3,3-trifluoropropyl)silane) was purchased from Sigma.

Mean hydrodynamic diameter and zeta potential were measured using a Brookhaven NanoBrook ZetaPALS zeta potential and dynamic light scattering instrument (Holtsville, N.Y., USA). The particle size was analyzed as an intensity averaged distribution using a scattering angle of 90° at 25° C. The Smoluchowki model was utilized to calculate the zeta potential from mobility measurements. All measurements were performed in 0.05×PBS (pH 7.4) at 25° C.

AFM analysis was performed with a Nanocscope Ma Dimension 3100 SPM system (Digital Instruments, Santa Barbara, Calif.) operating in tapping mode. This instrument is located in the Nebraska Center for Materials and Nanoscience's Scanning Probe Microscopy.

The phosphotungstic negative stain method was utilized for visualization of the LNP system using transmission electron microscopy (TEM). A drop of each sample was applied to separate copper grids coated with a carbon film and left to air dry. A 2% phosphotungstic acid solution was applied for negative staining, and the samples were analyzed using a Hitachi H7500 transmission electron microscope.

The 21MT-1 cell culture line was isolated from the metastatic pleural effusion mammary tumor specimens. The 21MT-1 cells were cultured in α-MEM media supplemented with 1% Penicillin-Streptomycin (PS), 1% L-glutamine, 20 mM HEPES, 5% fetal bovine serum (FBS), non-essential amino acids, sodium pyruvate (all listed reagents from Invitrogen), 12.5 ng/mL epidermal growth factor (EGF) and 1 μg/mL hydrocortisone (both from Sigma). This media is termed "complete 21MT-1 media", (i.e. complete media) and the absence of FBS and PS is regarded as "incomplete 21MT-1 media" (i.e. incomplete media). SKBR3 (ATCC HTB30), a human HER2+ invasive mammary gland adenocarcinoma cell line, were cultured in analogous conditions as the 21MT-1 cells except without the addition of EGF or hydrocortisone. MCF10A (ATCC CRL-10317), human normal breast tissue cell line, were cultured in DMEM/F12 (Mediatech) and supplemented with 1% L-glutamine, 1% Penicillin-Streptomycin, 5% Horse Serum, 0.1 ng/ml cholera toxin (Sigma), 0.5m/ml hydrocortisone, 10m/mL insulin (Sigma), and 0.02 ng/μL rhEGF (Sigma). The cells were kept in aseptic conditions, and grown in an incubator at 37° C. with 5% $CO_2$.

Flow cytometry was performed using a FACSCantoII from Becton Dickenson (Franklin Lakes, N.J., and USA).

The difference between experimental groups was analyzed by a one-way analysis of variance (ANOVA) and by a subsequent Turkey's multiple comparison test in Sigma Plot Software. For statistical analysis of all data, $p<0.05$ was regarded as the lowest acceptable threshold for significance.

Example 1. Polyelectrolyte Multilayer Base Fabrication

A polyelectrolyte multilayer (PEM) base structure of PLL and SPS was constructed by sequential adsorption of the polyelectrolytes on top of an oxygen plasma treated surface (glass slide or tissue culture plate). The negatively charged surface was first incubated with 0.5 mg/mL PLL (20 μM PBS, 0.15M NaCl) for 20 minutes, followed by numerous washing steps with deionized water (DI) to remove excess polymer, and subsequent incubation with 10 mM SPS (0.1M NaCl) for another 20 min to create a single PEM bilayer. This process was performed 4.5 times to create the PLL topped PEM base structure $(PLL/SPS)_{4.5}$. When used for cell culture experiments, the PEM base structure was UV sterilized for 8-12 hours in a biosafety cabinet.

Figure 1B:
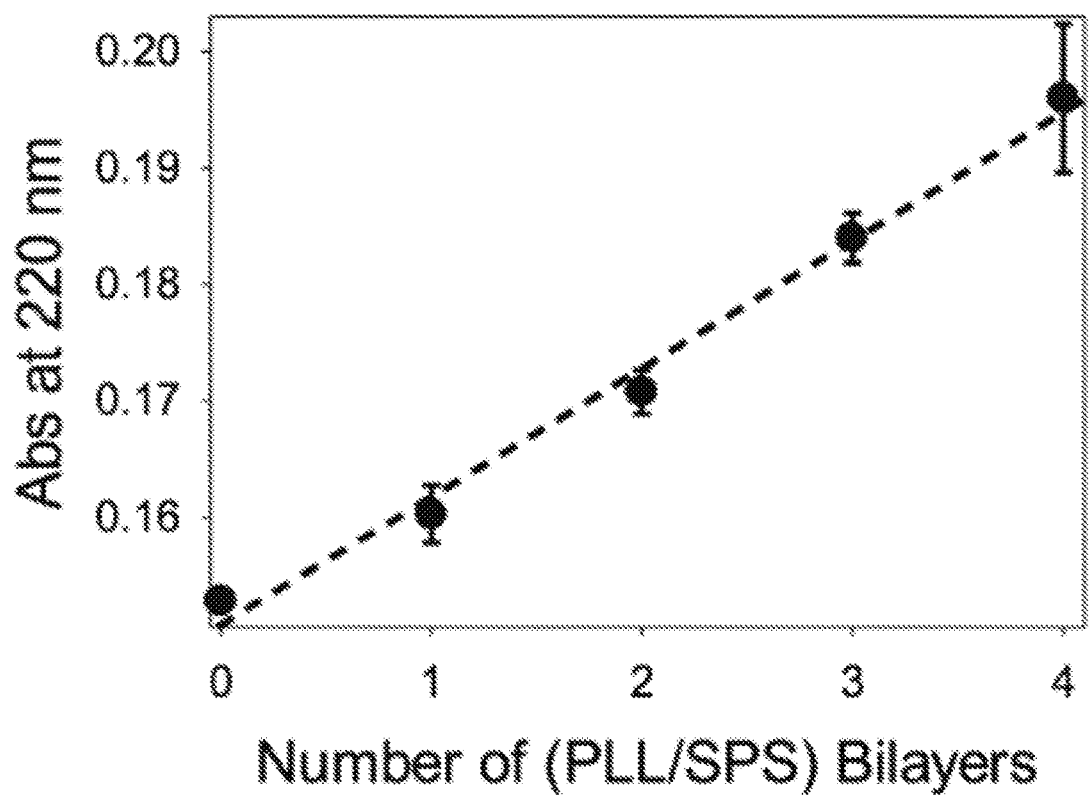
FIG. 1B shows representative UV absorbance readings (220 nm, characteristic for SPS) as a function of bilayer addition to demonstrate base construction.
Figure 1C:
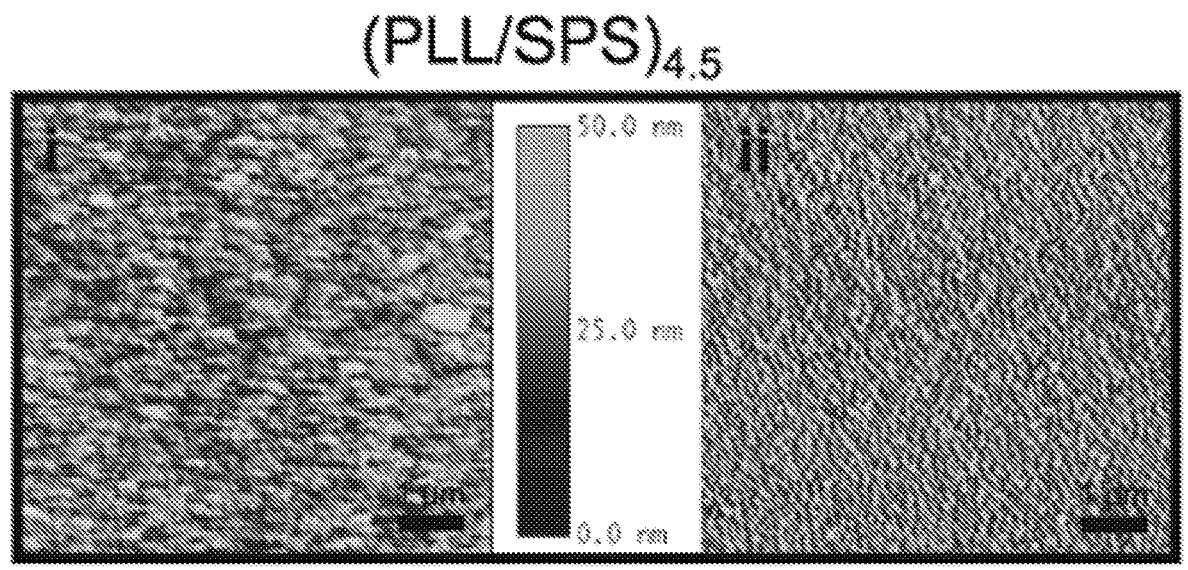
FIG. 1C shows representative atomic force microscopy (AFM) images of the $(PLL/SPS)_{4.5}$ base platform via height (i) and phase contrast (ii) analysis to visually demonstrate a uniform surface ideal for nanoparticle deposition. Scale bar for AFM is 1

The buildup of the PLL/SPS films was confirmed via UV-Vis spectrophotometry, as shown in FIGS. 1A-B using absorbance at 220 nm (finger print spectra of SPS) and fluorescence (Rhodamine tagged SPS). As is shown in FIGS. 1A-B, multilayered PLL/SPS coatings displayed linear increase in UV-absorbance spectrum with each successive double-layer addition, thus validating PEM film construction. Atomic force microscopy experimentally confirmed a high degree of surface uniformity on the (PLL/SPS)$_{4.5}$ base platform signifying an ideal surface for nanoparticle deposition, as is shown in FIG. 1C.

Example 2. Preparation of HA Coated Liposomes (HALNPs)

Multilamellar vesicles (MLVs) composed of PC, DPPE, and CHOL in a (3:1:1) molar ratio were created by the traditional dry film method as previously reported (see e.g., Peer et al., Science, 2008, 319, 627-630; and Hayward et al, Journal of Biomedical Nanotechnology, 2016, 12:554-568). The MLV solution was then extruded through progressively smaller membrane pore sizes with a mini extruder apparatus (Avanti Polar Lipids) kept above the gel transition temperature of the lipids at 65-70° C. to reach a final hydrodynamic diameter of 80-100 nm (LNP). These nanoscale LNPs were purified by ultracentrifugation (1.5 hr., 135,000 g) to remove lipid debris and were re-suspended in borate buffer (pH 8.6). To covalently coat the nanoscale LNPs, HA was dissolved in sodium acetate buffer (pH 5), activated with EDAC at a mass ratio of 1:20 (HA:EDAC) at 37° C. (pH ~4) for 2 hours (see e.g. Kleiner et al., Journal of Controlled Release, 2014, 181, 1-10), and mixed with the purified LNPs overnight to promote amide bond formation (HALNPs). Separation of the resulting HALNPs from excess reagents in solution was achieved by washing three times using ultracentrifugation. Following purification, the particles were aliquoted, snap frozen in ethanol with dry ice, and lyophilized using a Labconco Chamber Freeze Dry System (Kansas City, Mo., USA) (see e.g., Puranik et al., International Journal of Pharmaceutics, 2013, 441, 665-679). The lyophilized particles were stored at −80° C. until use.

Example 3. Directed Deposition of HALNPs onto PEM Films

To determine the extent of the interaction between the HALNPs and PLL for potential ionic driven adsorption, the two components were mixed in PBS and measured the zeta potential and hydrodynamic diameter were measured, and are summarized in Table 1. From this analysis it was found a mass ratio of 1:0.1 (Lipid: PLL) was sufficient to completely mask and reverse the charge of the HALNPs.

TABLE 1

Dynamic Light Scattering and Zeta Potential Analysis of Representative LNP systems

| Sample ID (Lipid:PLL mass ratio) | Hydrodynamic Diameter (nm) | Polydispersity Index | Zeta Potential (mV) |
|---|---|---|---|
| LNP | 95.1 ± 0.6 | 0.087 | −9.46 ± 0.31 |
| HALNP | 164.9 ± 1.5 | 0.198 | −23.29 ± 4.70 |
| HALNPDOX | 175.9 ± 7.5 | 0.233 | −17.05 ± 2.40 |
| HALNP-PLL (1:0.1) | 235.2 ± 8.5 | 0.278 | 20.08 ± 0.42 |
| HALNP-PLL (1:0.5) | 310.6 ± 19.0 | 0.310 | 22.74 ± 0.64 |
| HALNP-PLL (1:1.0) | 363.0 ± 31.0 | 0.360 | 23.45 ± 0.62 |

Example 4. Adsorption Process for HALNPs

Figure 2A:
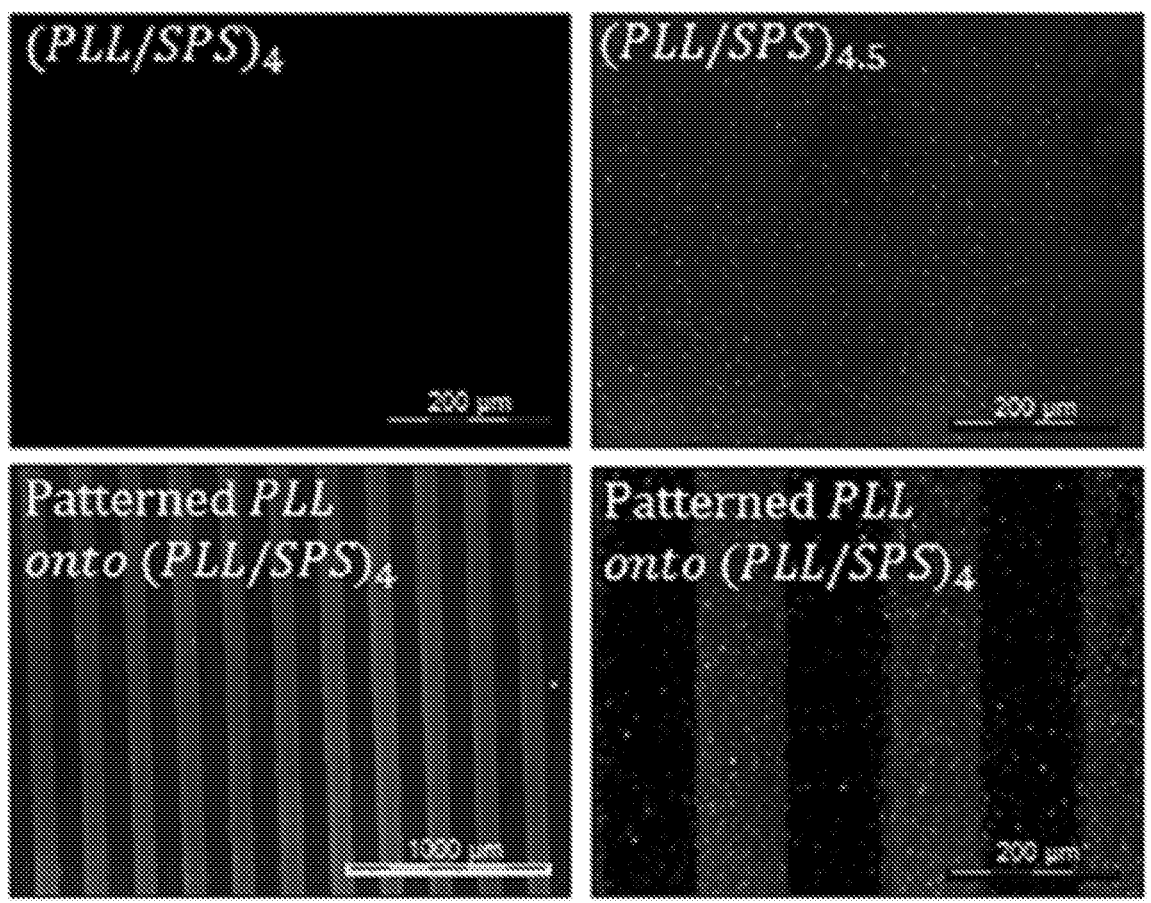
FIG. 2A shows preferential deposition of hyaluronic acid covalently functionalized liposomes (HALNPs) on poly-L-lysine (PLL) over poly(sodium styrene sulfonate) (SPS) topped surfaces. Capillary Force Lithography (CFL) was used to create PLL patterns on $(PLL/SPS)_4$ and to demonstrate the level of spatial control for nanoparticle adsorption.

To monitor the adsorption of HALNPs, 0.15 mass % of Top Fluor fluorescently conjugated cholesterol was added to the initial lipid stock to effectively tag the nanoparticles. Then, to initially determine if the HA-LNPs could successfully adsorb onto a PEM surface, 180 μg lipid/cm$^2$ was incubated with both PLL (PLL/SPS)$_{4.5}$ and SPS (PLL/SPS)$_{4.5}$ topped base layers fabricated in a 12 well plate for three hours at room temperature. Following incubation, the surfaces were washed 3× with 20 mM HEPES and visualized with an Axiovert 40 CFL Zeiss (Jena, Germany) Inverted Microscope with fluorescent filter, and the images were captured with a Progres C3 Jenoptick camera. Following deposition of the HALNPs, a capping layer consisting of an addition 2.5 bilayers of PLL and SPS, (PLL/SPS)$_{2.5}$, was added on top of the anionic nanoparticle monolayer following previously described adsorption protocol with the sole procedure change of using 20 mM HEPES for wash steps in place of DI water. The capping layer was added sequentially by hand in an aseptic environment to ensure sterile conditions. Validation of the selective deposition of negatively charged HALNP on positively charged PLL is shown in FIG. 2A.

Example 4A. Rehydration (Entrapment) Protocol and Cargo Encapsulation Quantification Lyophilized HALNP particles were rehydrated with 1/10th of the original solute volume composed of nuclease free water containing the cargo (e.g., FITC-Dextran, miRNA), followed by quick vortex agitation to ensure the full quantity of lyophilized powder was hydrated. After total rehydration the mixture was left to rest for 30 minutes to allow for lipid membrane re-assembly. Following this rest period, PBS solution was added to the sample to match the initial pre-lyophilization volume and un-encapsulated drug was removed by ultracentrifugation (140,000 g, 4° C., and 1.25 hr.). For encapsulation efficiency determination of the FITC tagged Dextran (FD) (Sigma) cargo, fluorescence at 495 nm em/520 em was measured in the presence of 0.1% Triton X-100 detergent to disrupt the lipid bilayers.

Figure 8A:
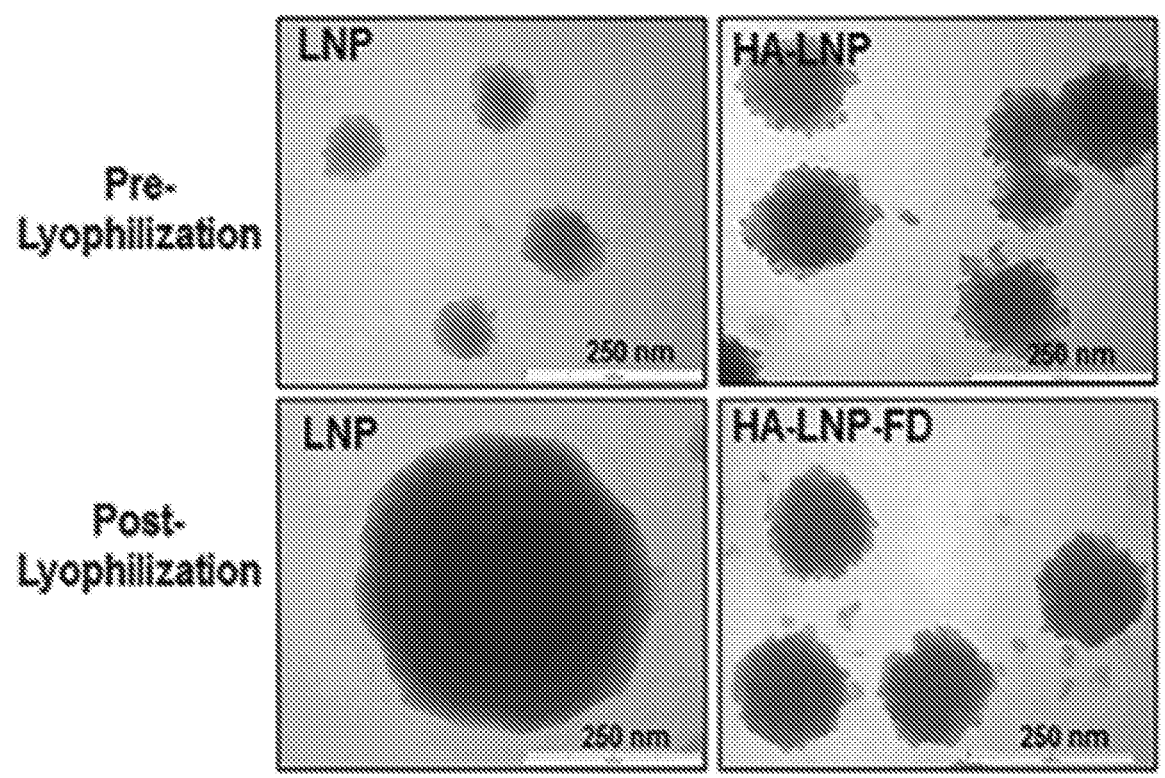
FIG. 8A shows representative Transmission Electron Microscopy (TEM) images using the negative stain method with 2% phosphotungstic acid. Scale bars are 250 nm.

Following the lyophilization process and subsequent rehydration in the presence of physiological buffer, the HALNPs particle size increased minimally and underwent no significant change in net surface charge, indicating that all HA remained on the outside of each particle during the bilayer reformation process. This step was crucial to ensure that the HALNPs would not be structurally altered during the entrapment procedure. TEM characterization of the LNP system exposed that 1) the surface roughness increased post crosslinking to HA, further providing validation of an appreciable coating of the biopolymer on the nanoparticle surface, and 2) that HA is an effective cryoprotectant for LNPs and is required to keep the nano-dimensions of the platform during the drug entrapment process, as shown in FIG. 8A.

Figure 8B:
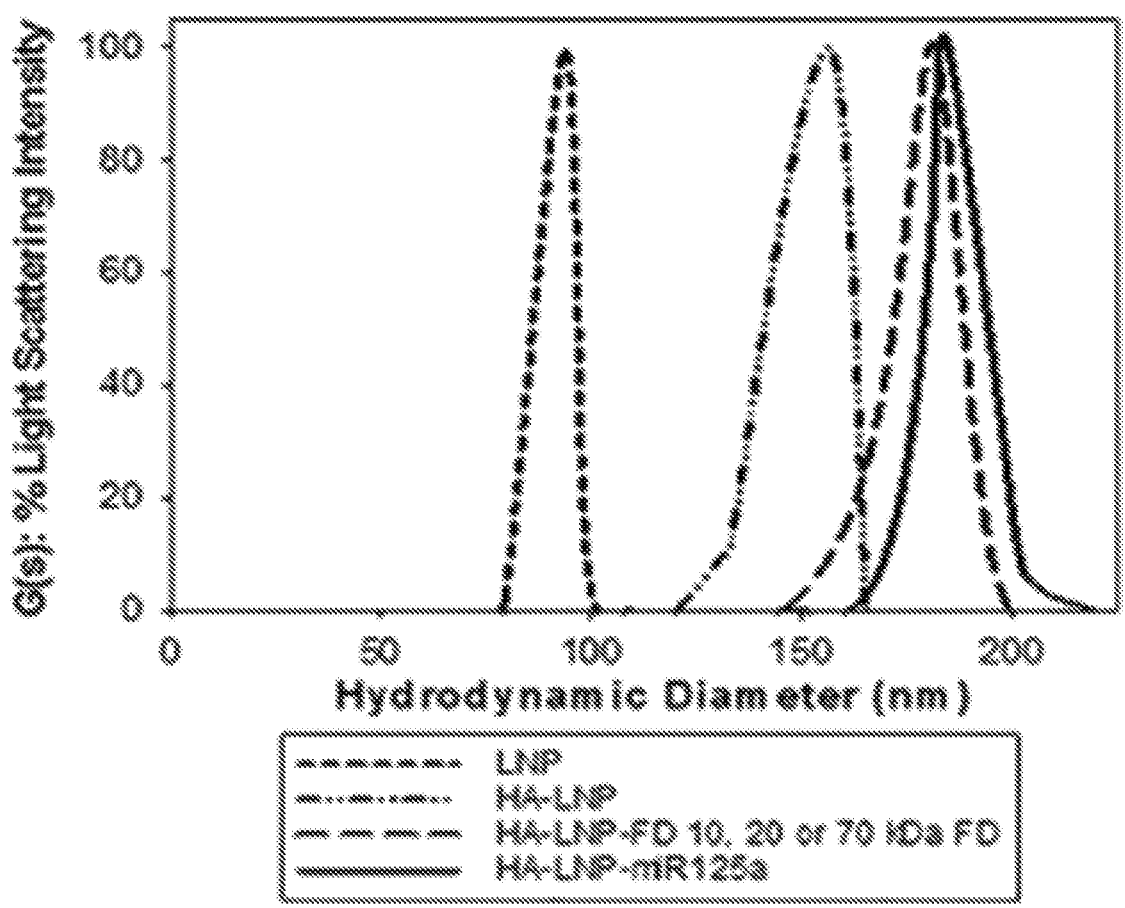
FIG. 8B shows particle size distribution data for representative LNP and HALNP nanoparticle systems.

A range of molecular weight FITC-tagged Dextran (FD; 10, 20, and 70 kDa) were successfully encapsulated and used to demonstrate that the diameter of the HALNP carrier post drug entrapment is not a function of the size of the cargo in the aqueous interior of the nanoparticle, as well as the versatility of the carrier to entrap a broad range of cargo sizes. The tumor suppressor miR125a-5p was also successfully encapsulated in an analogous manner with additional precautions taken to avert RNAse driven degradation. Comprehensive data on particle size, surface charge, and cargo entrapment is shown in Table 2. Particle size distributions of the nanoparticle systems HALNP, HALNP-FD (10, 20, and 70 kDa, respectively), and HA-LNP-miR125a-5p were also probed to confirm that in each case a monodisperse population of particles was obtained, as shown in FIG. 8B.

TABLE 2

| | Quasi Elastic Light Scattering | | Electrokinetic | Drug |
|---|---|---|---|---|
| | Hydrodynamic Diameter (nm) | Polydispersity Index (PI) | Potential Zeta Potential (mV) | Encapsulation Efficiency (%) |
| LNP | 93.6 ± 0.4 | 0.061 | −9.46 ± 0.31 | — |
| HALNP | 157.2 ± 1.4 | 0.105 | −38.07 ± 0.35 | — |
| HALNP Rehydrated | 182.1 ± 1.2 | 0.201 | −41.24 ± 0.57 | — |
| HALNP-10, 20, or 70 kDa FD | 185 → 200 | 0.15 → 0.21 | −41 → −43 | 35 → 55 |
| HALNP-miR125a | 197.5 ± 1.7 | 0.182 | −43.24 ± 0.57 | 24.1 ± 4 |

With a known amount of fluorescent drug present during the entrapment procedure, a standard curve was utilized to determine the amount entrapped. For encapsulation analysis of Human miRIDIAN miR125a-5p Mimic or scramble miR negative control (both from Dharmacon), a specific RNA binding dye, Quant-iT Ribogreen RNA Assay (Invitrogen), was utilized in the presence and absence of 0.1% Triton X100 detergent following a previous protocol (see e.g., Landesman-Milo et al, *Cancer Lett.* 2013, 334:221). The RNA binding dye was unable to penetrate intact lipid membranes, and therefore in the absence of detergent only the fluorescence of the un-entrapped miRNA was measured. In the presence of detergent, the total fluorescence was measured to determine the % encapsulation. Additionally, by comparing the total fluorescence to a RNA standard fluorescence curve, the exact concentration of miRNA entrapped was determined.

Example 5. Atomic Force Microscopy (AFM)

AFM was used to visualize the PEM base platform pre and post deposition with HALNPs. Three samples were prepared: 1) the PEM base platform (PLL/SPS)$_{4.5}$, 2) HALNPs deposited on the base platform without capping layer, and 3) deposited HALNPs on the (PLL/SPS)$_{4.5}$ base with a (PLL/SPS)$_{2.5}$ capping layer. All samples were allowed to air dry in an oven at 25° C. overnight. Both height and phase (deflection) images were obtained.

Example 6. Capillary Force Lithography (CFL) to Pattern HALNPs

To further investigate the differential adhesion of HALNP on PLL surfaces over SPS surfaces, PLL was patterned on (PLL/SPS)$_4$ films using capillary force lithography (CFL) and exposed fluorescently labeled HALNPs onto these films.

The silicone master pattern was secured to the bottom of a large cell culture dish, and was placed in a desiccator with an open vial of fluorosilane. The desiccator was evacuated by vacuum pump, creating a partial pressure of fluorosilane. Meanwhile, PDMS elastomer and cross linker were combined in a (9:1) mass ratio, and stirred vigorously by hand for five minutes. The silicone master pattern was removed from the desiccator, and the PDMS mixture was poured over the master pattern. The PDMS covered master pattern was placed in a new desiccator, which was alternately evacuated by vacuum pump and re-pressurized to remove any bubbles in the liquid PDMS. Once all bubbles were eliminated, the mixture was cured in the oven at 60° C. for 24 hours. After curing, the PDMS was removed from the silicone master pattern with a scalpel, and the stamps were cut to size.

PDMS micro-patterned line stamps were cut into rectangular sections with open channels on two out of four faces. The stamps were cleaned with liquid hand soap and DI water, and then blown dry with air. They were then treated in an oxygen plasma cleaner for one minute in order to induce a negative charge on their surface. The stamps were then placed pattern down on top of polyelectrolyte multilayer (PEM) coated glass slides (PLL/SPS)$_4$, and stabilized with a weight (90 g) placed on top. 10 µL of 0.5 mg/mL PLL solution was evenly applied to the edge of the stamp with a pipette, at the contact point of the open channels and the PEM coated slide. By capillary force and charge/charge interactions, PLL solution was drawn into the channels. The patterns were allowed to dry for twenty-five minutes before the stamps were removed. Following this dry time the patterned PLL was UV sterilized for 8-12 hours, coated with HALNPs, and capped with the capping layer prior to cell culture work.

As observed in FIG. 2A, the HALNPs selectively adhered to the PLL regions compared to SPS films which is indicative of the fluorescent patterns formed on the PEM surfaces.

Example 7. Affinity Assay and Saturation Curve for HALNP Loading

To evaluate the loading of HALNPs into the PEM platform, a dual affinity and saturation curve assay was systematically implemented to determine optimum and saturated deposition conditions. First, a standard curve of known fluorescent HALNPs mass (termed lipid mass) was used to create a fluorescent standard curve. Then, two 48 well plates were coated with a PEM base layer. One plate was coated with a PLL topped layer (PLL/SPS)$_{4.5}$, while the other was coated with an SPS topped layer (PLL/SPS)$_4$. Then, a range HALNP concentration, 1 to 800 µg/ml, was incubated with the 48 well plates for 3 hours at room temperature covered in foil. Following this incubation time, the supernatants from each well were read against the standard curve to determine concentration of un-attached nanoparticles, and the percent difference between the PLL and SPS topped substrate wells (at analogous nanoparticle incubation concentration) was used to determine the affinity of the HALNPs for that particular surface. The concentration of embedded particles deposited on the plate was also measured by reading the 48 well plate in a Biotek Synergy 2 Multi-Mode Plate Reader (Winooski, Vt., USA) to confirm conservation of mass (ex. 495 nm, em. 520 nm). To determine the HALNP saturation conditions of the PLL topped base platform, the 1) supernatant and 2) nanoparticle embedded plate data from the affinity assay was used to determine the exact amount of mass loaded per area as a function of the nanoparticle loading concentration. From this information, the saturation point of HALNPs was determined from a nonlinear regression analysis via Sigma Plot Software (San Jose, Calif., USA).

Figure 3A:
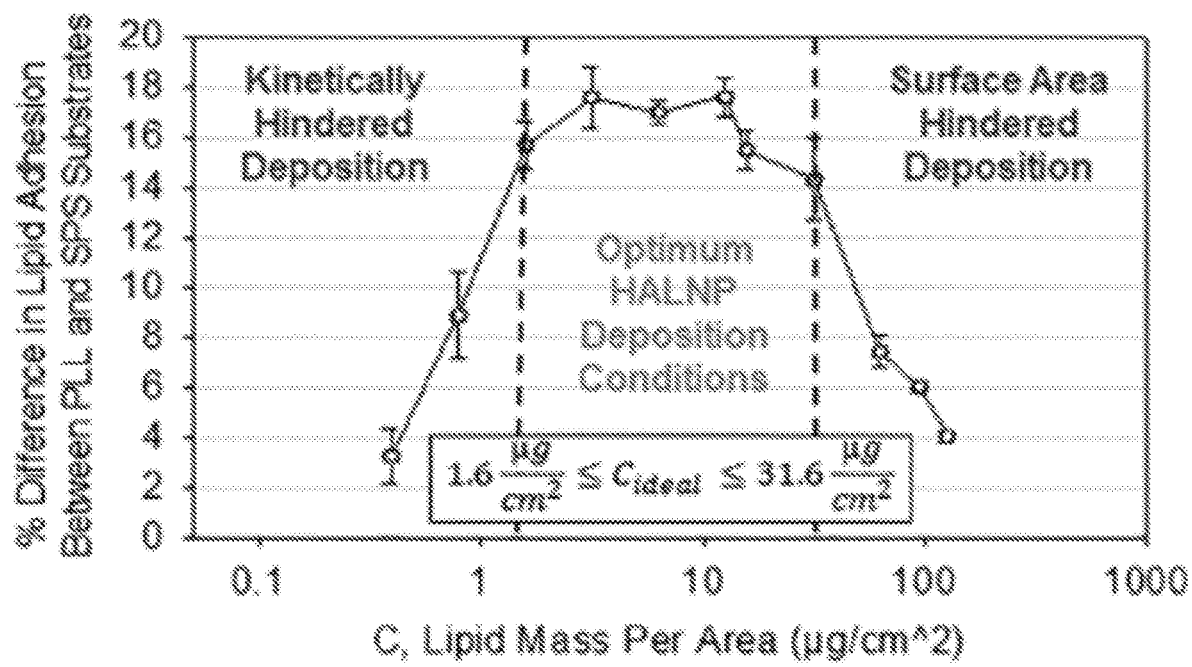
FIG. 3A shows representative data from an affinity assay for HALNP absorption on $(PLL/SPS)_{4.5}$ and $(PLL/SPS)_4$ substrates to determine the optimum conditions for nanoparticle deposition.
Figure 3B:
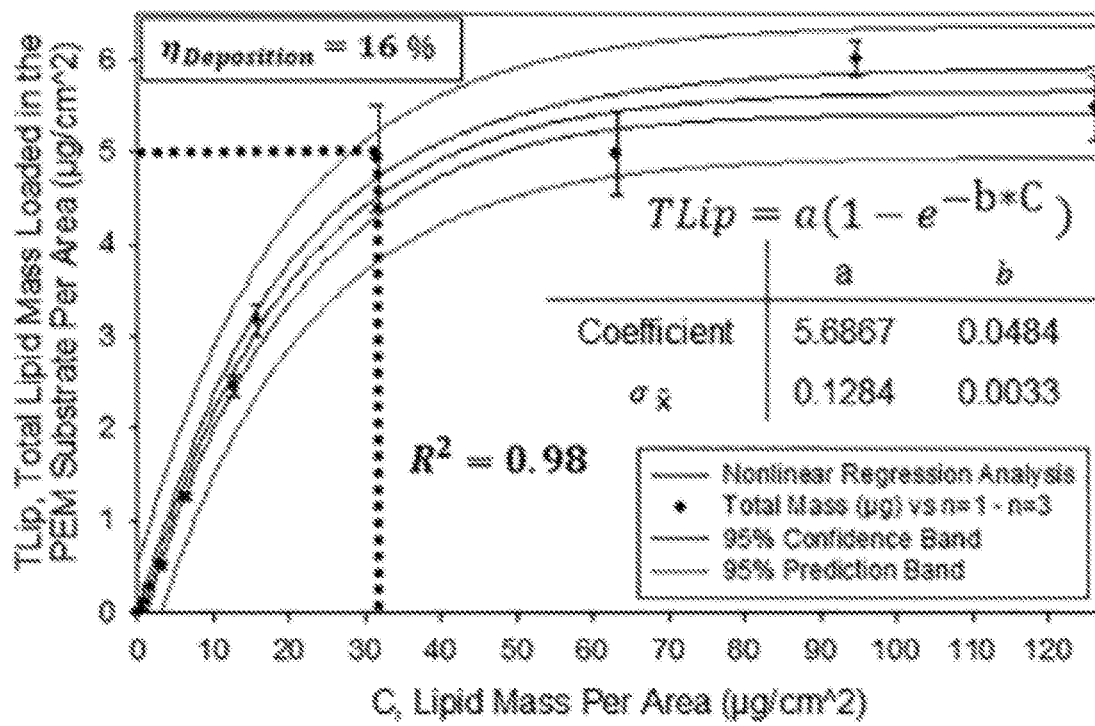
FIG. 3B shows a representative saturation curve analysis of total lipid loaded on $(PLL/SPS)_{4.5}$ per square centimeter as a function of total lipid added during the three hour incubation time.

The affinity assay between HALNP and both (PLL/SPS)$_4$ and (PLL/SPS)$_{4.5}$ was performed over a lipid range of 0.1 to 1000 µg/cm$^2$ utilizing analogous deposition conditions described previously. By analyzing the percent difference in lipid adhesion between the PLL and SPS topped platforms over the range of lipid concentration, it was estimated that a minimum and maximum lipid concentration of 1.6 µg/cm$^2$ and 31.6 µg/cm$^2$ is necessary to overcome kinetically hindered deposition and reduction in embedment efficiency due to limited surface area, respectively, as is shown in FIG. 3A. A saturation experiment analogous to a Michealis-Menton Kinetics curve was then performed to determine the maximum HALNP possible to load per unit surface area, as is shown in FIG. 3B. An exponential increase followed by saturation conditions was observed for the HALNP loading with a maximum loading of 5 µg/cm$^2$HALNPs achieved. At a loading concentration of 31.6 µg/cm$^2$, the HALNP deposition efficiency was calculated to be 16%. This information provides the ability to load a precise amount of HALNP within the PEM platform, and the capability to control the concentration of any encapsulated hydrophilic or hydrophobic cargo within the lipid bilayer of the nanocarrier.

Figure 3C:
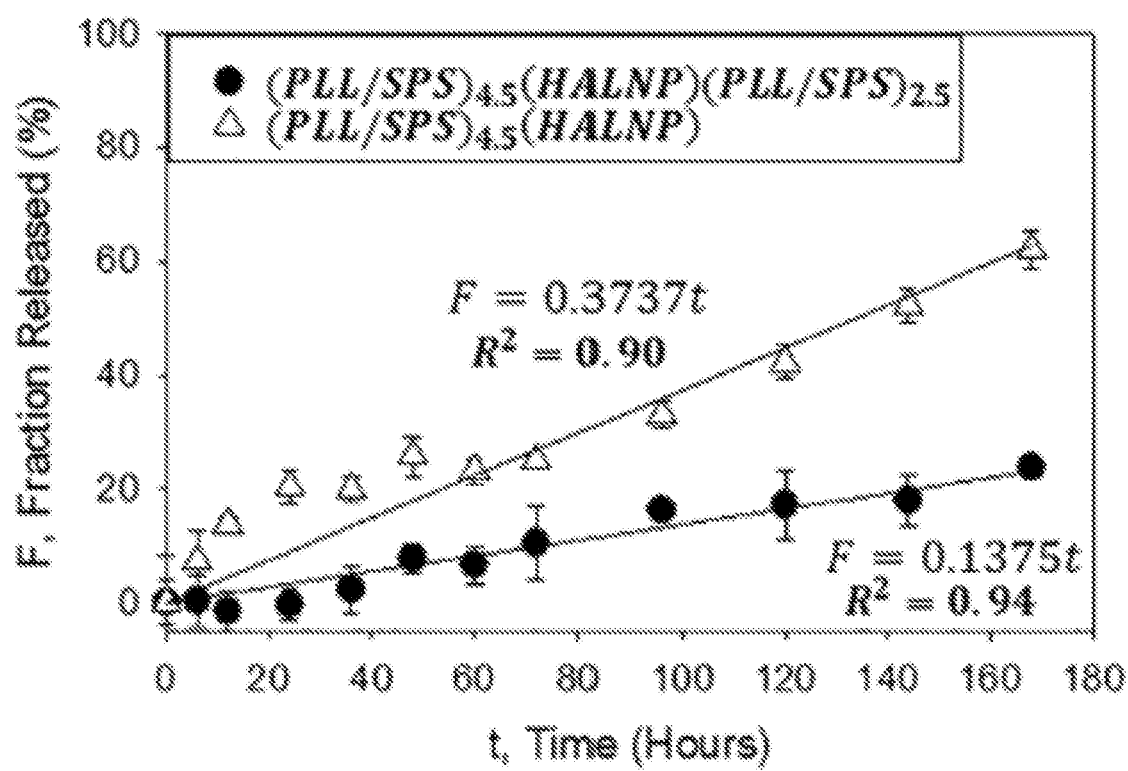
FIG. 3C shows a representative HALNP nanocarrier release profile from the non-capped $[(PLL/SPS)_{4.5}(HALNP)]$ and capped $[(PLL/SPS)_{4.5}(HALNP)(PLL/SPS)_{2.5}]$ HALNP-PEM platforms.

Next the release kinetics of the HALNPs from the PEM system was determined, both with and without the capping layer, as is shown in FIG. 3C. It was demonstrated that approximately 60% and 20% of the adsorbed HALNPs were released in the uncapped and capped PEM systems, respectively, over the course of seven days. In addition, the capped HALNP-PEM system demonstrated a linear release profile without an initial burst release that was observed in the early stages of the uncapped system. This indicated that the capping system atop the immobilized HALNP on PEM films provides the ability to achieve a highly controlled and sustained nanocarrier release profile.

Example 8. Fluorescent Recovery after Photobleaching (FRAP)

A HALNP loading of 5 µg lipid/cm$^2$ was deposited onto a (PLL/SPS)$_{4.5}$ base layer utilizing the previously mentioned saturation protocol. Then, a portion of the deposited HALNP layer was photo bleached with an Axiovert 40 CFL Zeiss (Jena, Germany) Inverted Microscope with a FITC filter for 5 minutes (see e.g., International Patent Application No. WO 2007/146001). The fluorescent microscope was then shut off for a designated amount of time (10 or 30 minutes) to allow for the assessment of nanoparticle mobility. After this wait time, the microscope was turned back on and a fluorescent image was immediately captured. This procedure was performed both with and without a (PLL/SPS)$_{2.5}$ capping layer over the HALNP deposited monolayer to compare the effect of nanoparticle confinement on mobility. All analyses were performed in wet conditions, in 20 mM HEPES buffer at pH 7.4 at room temperature. A control film without labeled nanoparticles has also been included to discern any background fluorescence.

Figure 2B:
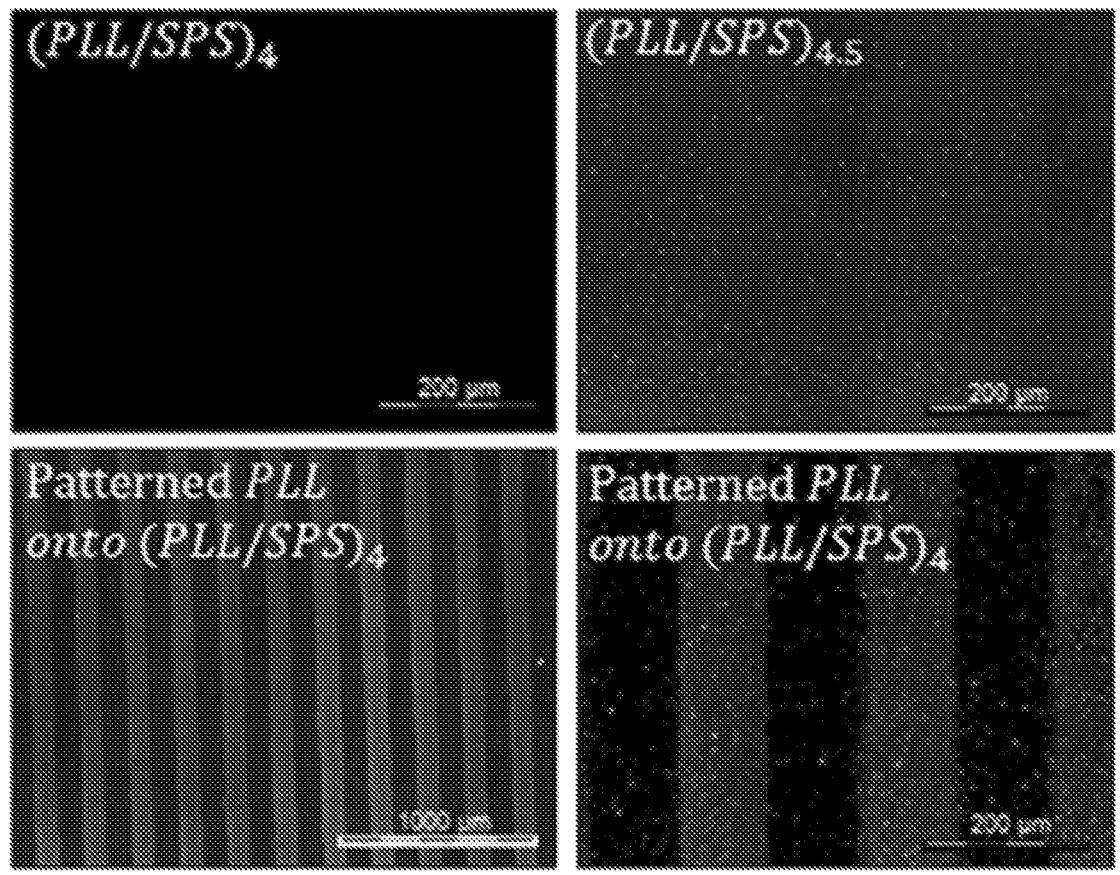
FIG. 2B shows a representative fluorescent recovery after photo bleaching (FRAP) analysis pre- and post- the addition of the capping layer at 0 and 10 min. The arrows point to particles that have moved during the experimental time lapse.
Figure 2C:
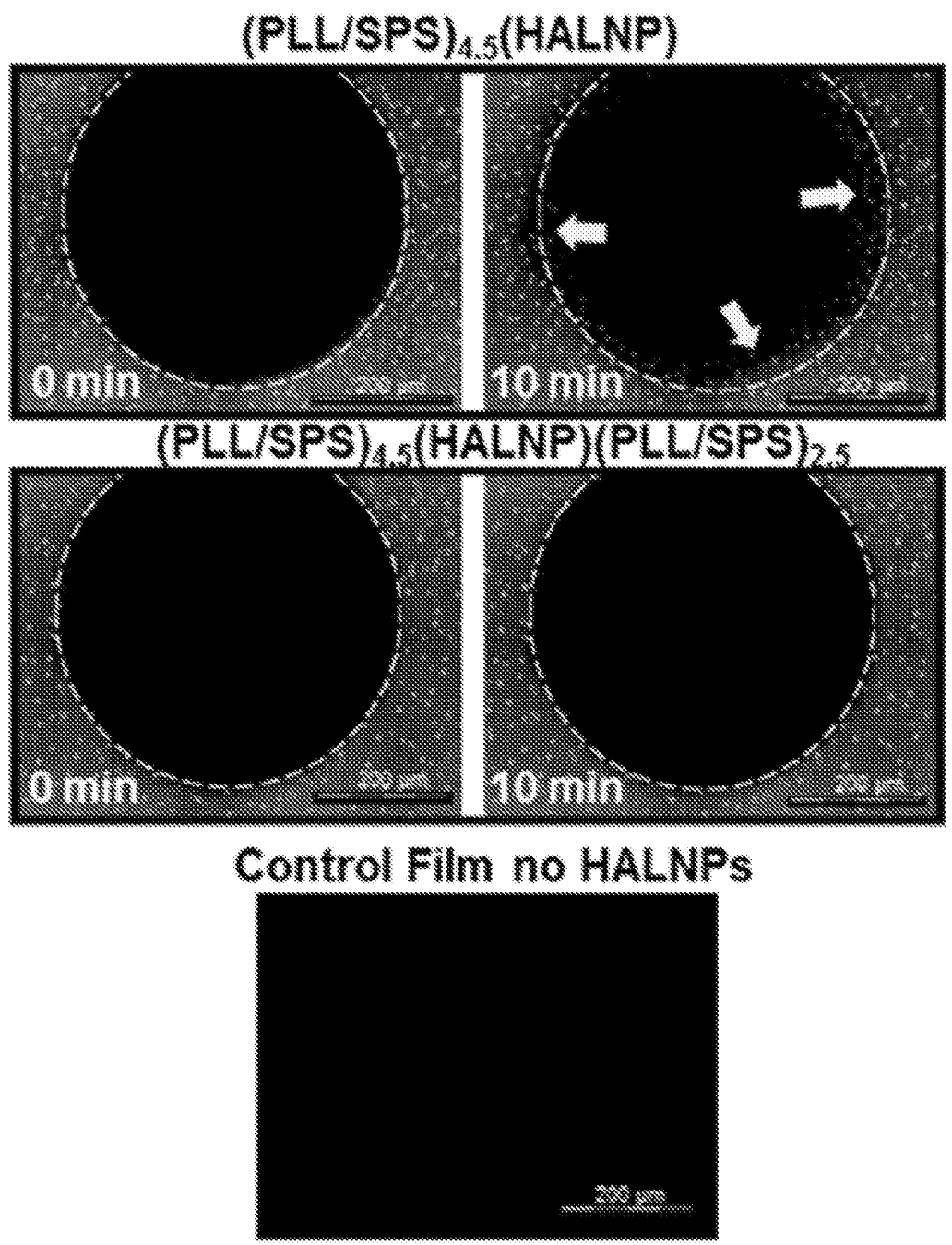
FIG. 2C shows a representative fluorescent recovery after photo bleaching (FRAP) analysis pre- and post- the addition of the capping layer at 10 min
Figure 2D:
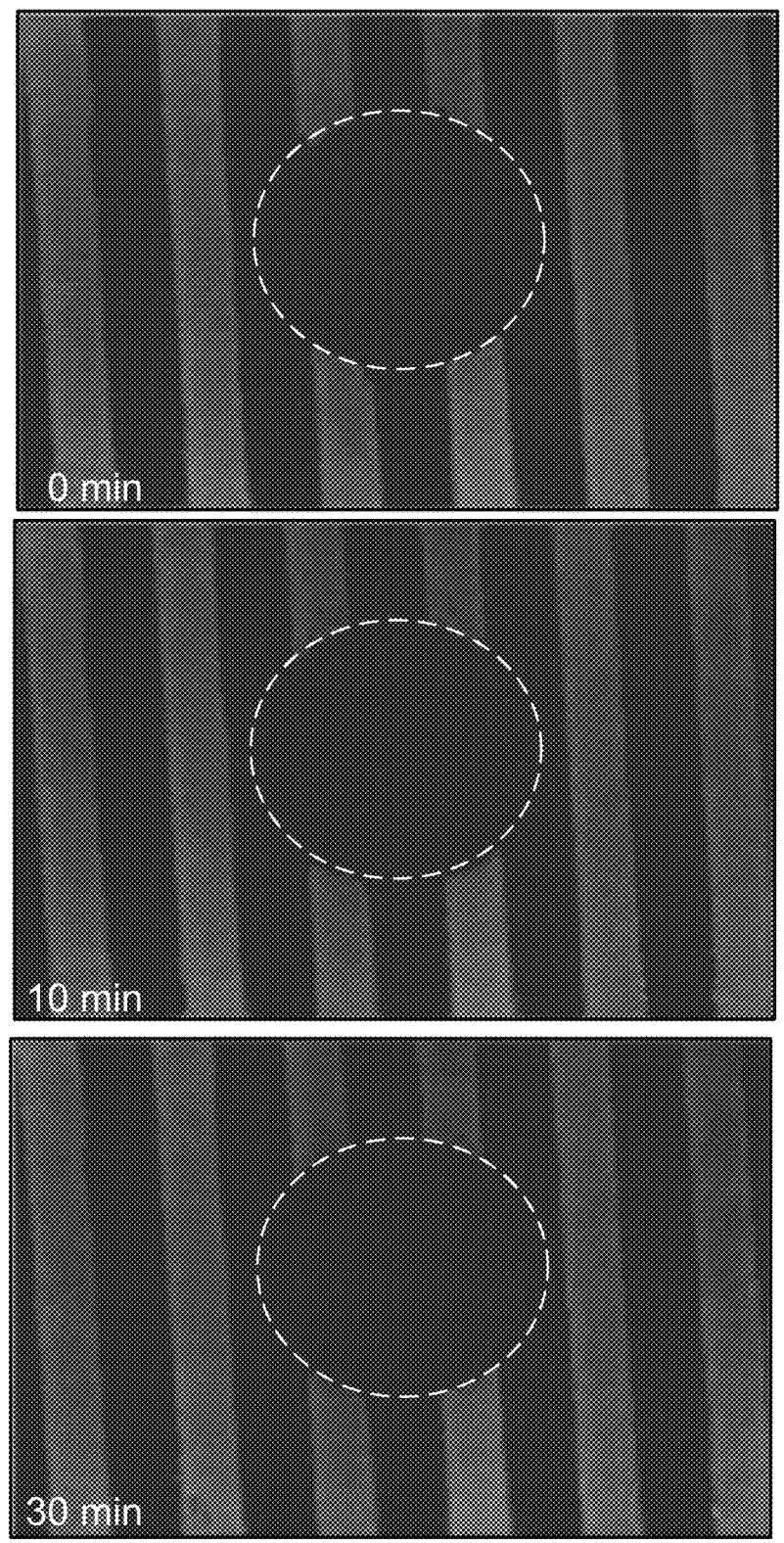
FIG. 2D shows a representative fluorescent recovery after photo bleaching (FRAP) analysis pre- and post- the addition of the capping layer at 0 min, 10 min, and 30 min.

FRAP experiments on fluorescently tagged HALNPs deposited atop (PLL/SPS)$_{4.5}$ films demonstrated that the HALNPs were not completely immobilized and were partially mobile on the PEM surface after 10 minutes, as is shown in FIG. 2B. As a result, the net immobilization of the particles was increased via an additional ionic interaction and physical barrier in the form of a (PLL/SPS)$_{2.5}$ "capping layer" above the adsorbed HALNPs (i.e., an additional polyelectrolyte multilayer). The FRAP experiment was repeated on the HALNP-PEM surface with the capping layer and found that that this additional barrier completely impeded the migration of the HALNPs within a PEM sandwich for both 10 min and 30 min, as shown in FIGS. 2B-2C. Atomic force microscopy of the HALNP embedded PEM was also performed pre- and post- addition of the capping layer. This demonstrated that the adsorbed nanoparticles remained spherical pre- and post- addition of the capping layer, and also validated the deposition of the capping layer on top of the HALNPs.

Example 9. Flow Cytometry

Figure 4A:
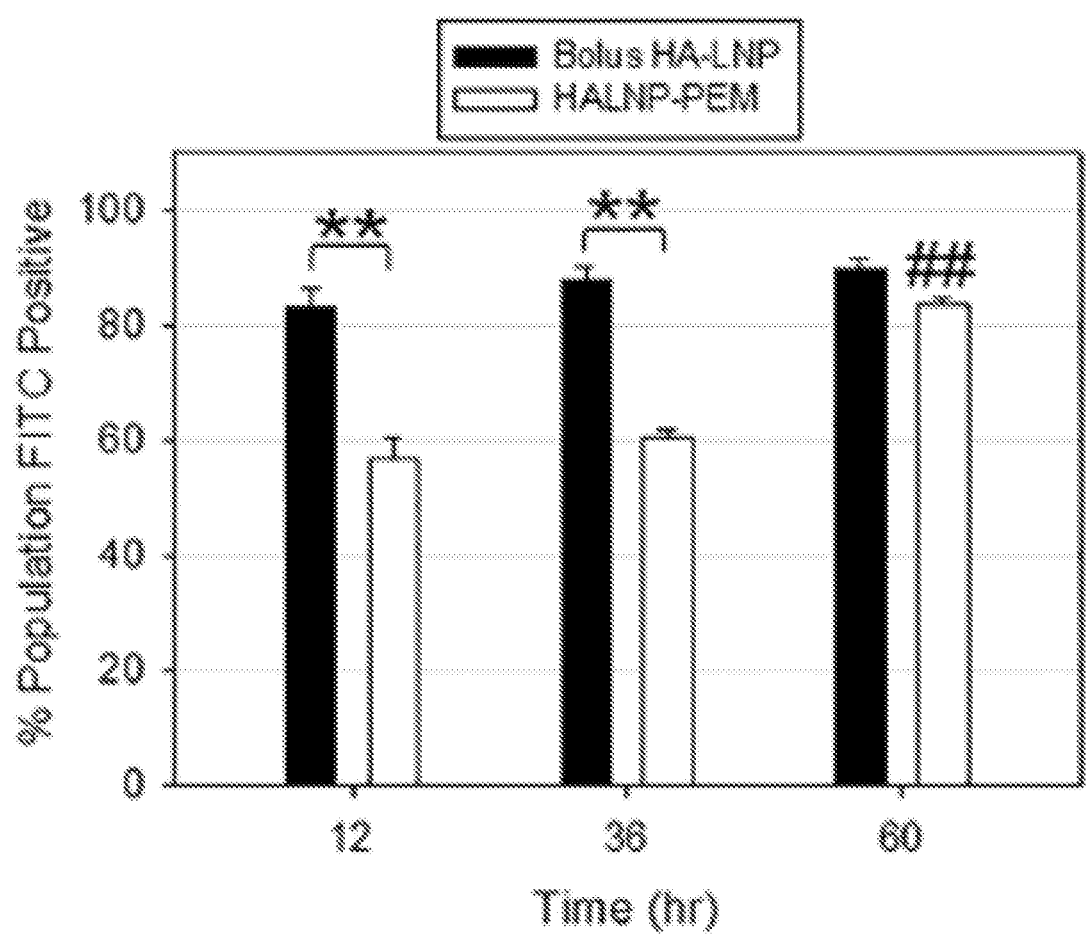
FIG. 4A shows 21MT-1 metastatic breast cancer cell uptake of fluorescently conjugated HALNPs from the embedded PEM system with capping layer and HA-LNP bolus system as a function of time $[(PLL/SPS)_{4.5}(HALNP)(PLL/SPS)_{2.5}]$ using flow cytometry analysis (percent cell population FITC positive uptake between the HALNP-PEM and HA-LNP bolus system). # denotes significance between a specific sample type and the preceding time point following the same significance scale as the stars).
Figure 4B:
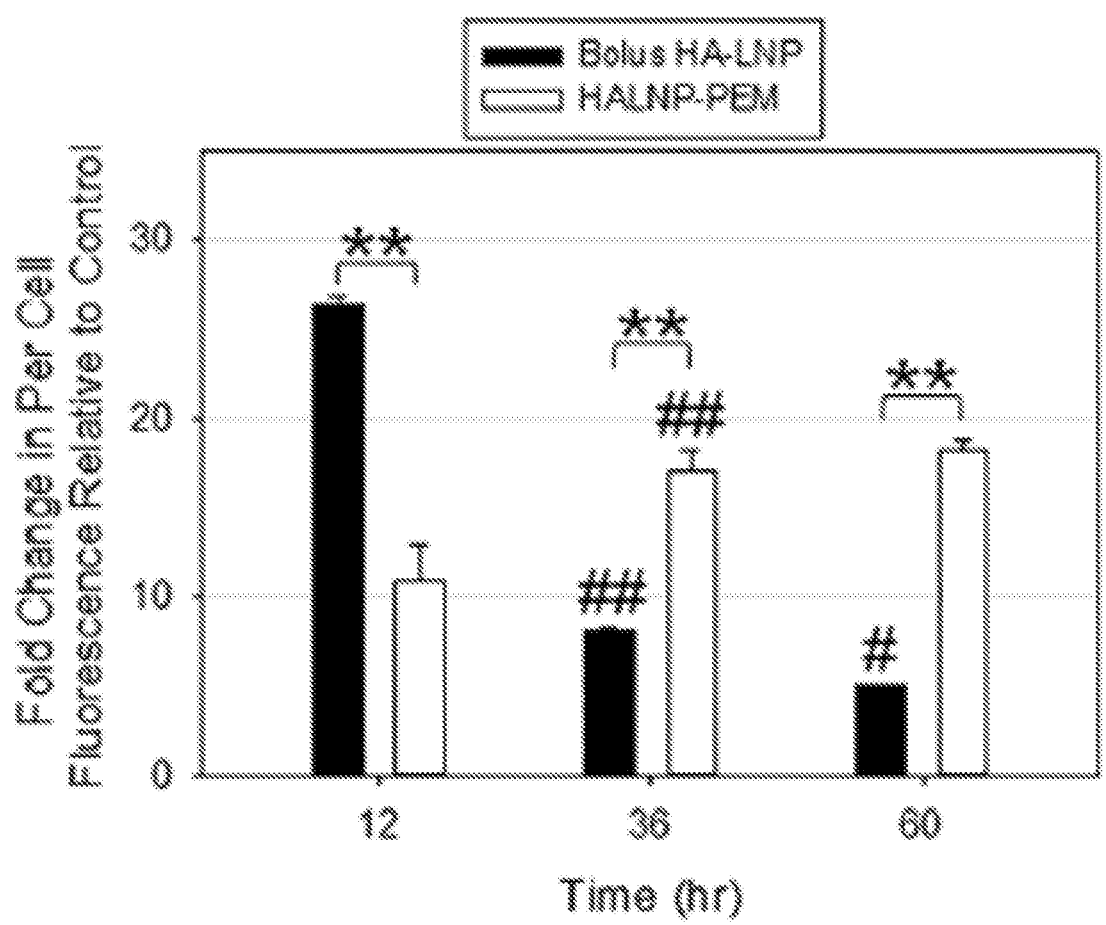
FIG. 4B shows 21MT-1 metastatic breast cancer cell uptake of fluorescently conjugated HALNPs from the embedded PEM system with capping layer as a function of time $[(PLL/SPS)_{4.5}(HALNP)(PLL/SPS)_{2.5}]$ using flow cytometry analysis (per cell fluorescence directly comparing nanoparticle uptake between the HALNP-PEM and HA-LNP bolus systems ($*P<0.05$, $**P<0.005$; n=3)). # denotes significance between a specific sample type and the preceding time point following the same significance scale as the stars).

To study the effect of nanocarrier immobilization in PEM films on cellular uptake, the bolus delivery of fluorescently tagged HALNPs was compared to the HALNPs immobilized in the PEM films with the (PLL/SPS)$_{2.5}$ capping layer (HALNP-PEM). For this experiment, patient derived 21MT-1 metastatic breast cancer cells isolated from the metastatic pleural effusion were used as a model system. A time course study was performed via flow cytometry to determine the kinetics of cell uptake of the fluorescently tagged HALNPs when delivered in the bolus form compared to using the HALNP-PEM platform, as shown in FIGS. 4A-4B.

A 12 well culture plate was first plasma treated and deposited with a PEM base of (PLL/SPS)$_{4.5}$. This base platform was then UV sterilized overnight. Filter sterilized HALNPs with 0.15% Top Fluor fluorescent cholesterol were then deposited on the PLL surface applying saturation conditions, followed by the addition of the capping layer (5 µg/cm$^2$; total HALNP loading in a 12 well=20.05 µg HALNP per well). Each well was then seeded with 170,000 21MT-1 cells and placed in the incubator overnight to promote cell attachment. At 12, 24, and 36 hours, the cells were washed 3× with sterile 1×PBS, trypsinized, and transferred to flow cytometry tubes. Theses samples were then analyzed for fluorescence in the green channel (ex. 495 nm, em. 520 nm; 10,000 total events/read) against control cells. Both per cell fluorescence and total % population FITC positive information was measured. Additionally, bolus form HALNPs, free nanoparticles not bound to a substrate, were also incubated with 21MT-1 cells in an analogous manner (same seeding density of cells and concentration of 20.05 µg HALNPs per well) to compare the substrate mediated and bolus form intracellular delivery of HALNPs as a function of time.

At 12 hours, it was found that 55% of the cells were positive for HALNP uptake from the HALNP-PEM platform compared to 81% positive cells from the bolus delivery. Also at 12 hours, the per-cell fluorescence intensity of the cells on the HALNP-PEM was 11 fold higher than control cells as compared to 26 fold higher than control for the bolus delivery. At 36 hours, the percent cell population for the HALNP-PEM system increased to 60% while the bolus delivery remained unchanged. However, the per-cell fluorescent intensity in the HALNP-PEM increased to 17 fold higher than control cells (60% increase) compared to bolus delivery that decreased to 8 fold higher than control (68% decrease). These results demonstrate that the HALNP-PEM system has a sustained release of the HALNPs while the bolus delivery system has burst release kinetics with subsequent rapid intracellular degradation. At 60 hours, 80% of the cell population was positive for HALNP uptake in the HALNP-PEM platform which is comparable to the bolus delivery at 12 hours. This confirms that the HALNP-PEM platform performs on par with the bolus delivery method in regards to the efficiency of cell uptake. Also at 60 hours the per-cell fluorescence in the HALNP-PEM system increased by 6% compared to a 40% decrease for the bolus delivery, further confirming sustained delivery with the HALNP-PEM.

Figure 4C:
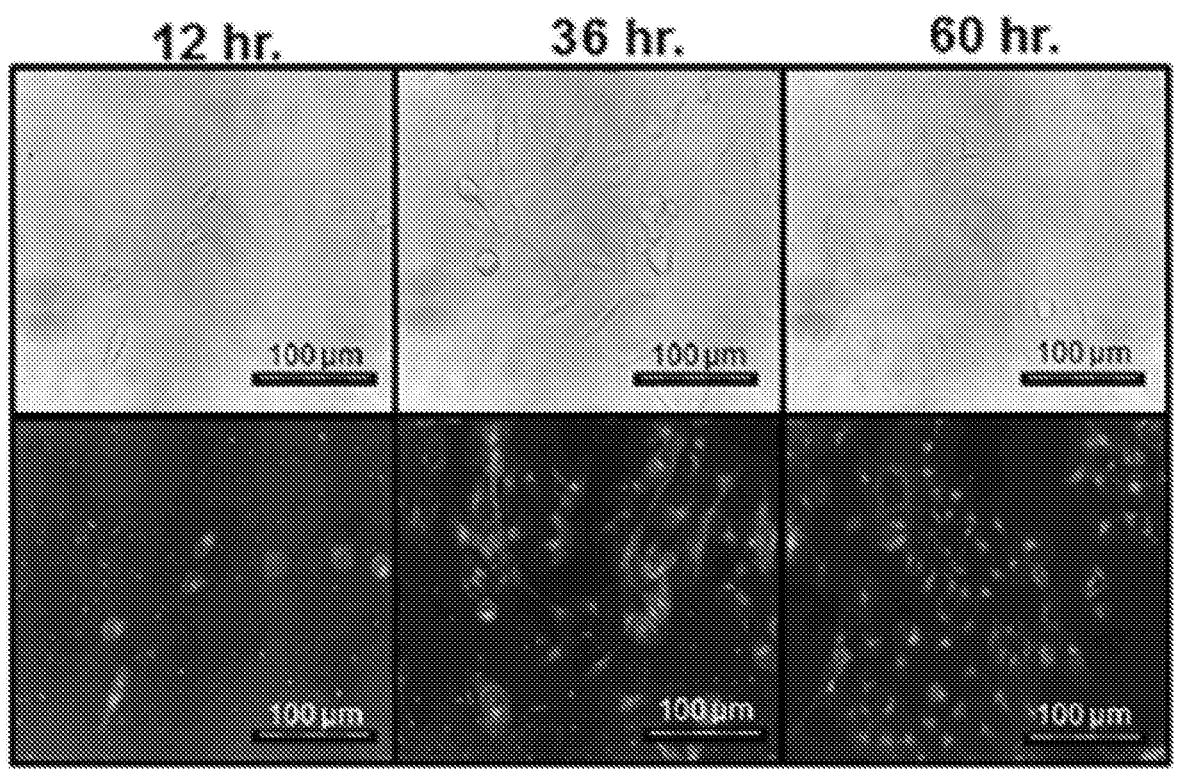
FIG. 4C shows representative imagines of a visual investigation of nanoparticle intracellular delivery on the HALNP-PEM platform using Phase Contrast and Fluorescent Microscopy.

To investigate the release mechanism of the HALNPs from the PEM platform, fluorescent microscopy was employed at different time intervals, as shown in FIG. 4C.

It was observed that the fluorescent cells increased gradually with each time interval, which is similar to the HALNP release profile demonstrated with the flow cytometry data. This experiment provided information regarding 1) validation of the intracellular delivery of the HALNPs and 2) evidence regarding the release of the HALNPs from the HALNP-PEM platform. The outcome of this experiment in combination with flow cytometry indicated that HALNP release from the HALNP-PEM platform may be a cell-enhanced process.

Example 10. Encapsulation of Doxorubicin (DOX) in HALNPs (HALNPDOX)

To determine the efficacy of delivering packaged drugs within the HALNP embedded nanocarrier, HALNPs were immobilized with encapsulated doxorubicin (DOX) within the HALNP-PEM platform.

Vials of lyophilized HALNPs were brought to room temperature and rehydrated with $\frac{1}{10}$ of the original pre-lyophilized volume with DOX dissolved in 0.05×PBS. These vials were then quickly vortexed to hydrate the entire dry lipid film, and left to rest for 30 minutes on a shaker table to mediate lipid membrane re-assembly and optimum DOX entrapment (HALNPDOX). Following the entrapment procedure, additional 1×PBS was added to bring the vials to the pre-lyophilized volume. Un-encapsulated DOX was removed by ultracentrifugation (140,000 g, 4° C., and 1.25 hr.) and subsequent wash steps with 1×PBS. To determine the amount of encapsulated chemotherapeutic in the aqueous core of the HALNPs, the natural fluorescence of DOX (ex. 470 nm, em. 585 nm) was measured in the presence of 0.1% Triton X-100 detergent to disrupt the lipid bilayers and compared to a standard curve of known DOX concentration. Following excess DOX removal, and quantification of total internal DOX payload, the final mass ratio between Lipid (HALNP) and DOX was 3.125:1. Therefore, the maximum loading of DOX encapsulated into the aqueous core of the HALNPs and then subsequently loaded onto the (PLL/SPS)$_{4.5}$ based on lipid saturation of the PEM was 1.6 μg DOX/cm$^2$.

Example 11. Cargo (DOX) and Carrier (HALNP) Release Kinetics from the PEM Platform The kinetics of release for the HALNP nanocarrier from the PEM platform with and without a (PLL/SPS)$_{2.5}$ capping layer was assessed by employment of a fluorescent plate reader. The PEM system embedded with HALNPs was incubated in 1×PBS at room temperature. At specific time points, the nanoparticle release medium was replaced to acquire samples and to ensure infinite sink conditions were maintained. Both supernatant and the HALNP embedded plate data (utilizing the established saturation conditions) were analyzed to confirm conservation of mass (ex. 495 nm, em. 520 nm). Release kinetics of HALNP encapsulated DOX from the capped and non-capped PEM platform was performed in the analogous manner utilizing the natural fluorescence of the chemotherapeutic (ex. 470 nm, em. 585 nm) in comparison to a standard curve.

Example 12. Potency Assay

The DOX concentration lethal to 50% of the 21MT-1 cells (LC$_{50}$) was determined utilizing the MTT (3-(4,5-dimethyldiazol-2-yl)2,5-diphenyl tetrazolium bromide) assay kit from Life Technologies (Carlsbad, Calif., USA). This colorimetric assay assesses cell health as a function of the mitochondrial conversion of MTT salt to Formazan. A two-step procedure was implemented for precise loading of DOX into the HALNPs and then into the HALNP-PEM platform.

First a solution of 500m of DOX in 0.05×PBS was used to rehydrate a lyophilized vial of HALNPs and excess (un-encapsulated) DOX was removed using ultracentrifugation (140,000 g, 1.25 hrs, 4° C.). A standard curve of known DOX concentrations was employed to determine the total amount of DOX encapsulated in the HALNP sample ("HALNPDOX"). The initial vial of HALNPs (1 mg Total Lipid) concentration was known, thus both the total amount of encapsulated DOX and lipid were fully determined. Secondly, the HALNPDOX particles were adsorbed onto the (PLL/SPS)$_{4.5}$ base platform ensuring the amount of lipid required to achieve a specified dosage of DOX was below the saturation conditions of the lipid as shown in FIG. 3B. The potency assay was run between 2.5 μg/mL DOX and 0 μg/ml DOX.

Following purification, the final mass ratio between Lipid and DOX was 3.125:1. Therefore, for the 2.5 μg/ml DOX concentration samples (highest concentration tested in potency assay), 3.9 μg HALNPDOX was adsorbed per well to achieve the desired DOX concentration (well volume=0.5 mL). This similar reasoning was used for all lower concentrations of HALNPDOX loading as well. The only difference in this loading procedure compared to empty HALNPs was the increase in the deposition incubation time from three hours at room temperature to overnight at 4° C. to ensure complete embedment of the HALNPDOXs as well as protect the activity of the DOX. Supernatant samples were removed following the adsorption protocol to ensure all particles deposited onto the (PLL/SPS)$_{4.5}$ base platform. In addition, DLS and Zeta potential analysis of the HALNP-DOX particles was analyzed to ensure the encapsulation of the DOX did not significantly alter with the size or charge of the HALNPs (and therefore the adsorption process). The (PLL/SPS)$_{2.5}$ capping layer was added immediately after the HALNPDOX adsorption.

21MT-1 cells were seeded at a density of 32,000 cells/well in three 48 well plates with different DOX configurations: 1) PEM platform with embedded HALNPDOX [(PLL/SPS)$_{4.5}$ (HALNPDOX)(PLL/SPS)$_{2.5}$], 2) Bolus form HALNPDOX, and 3) free non-encapsulated DOX. After a 24 hours incubation time between the three systems and the 21MT-1 cells, the media was aspirated and 5 mg/mL MTT working solution was added and incubated for 2 hours at 37° C. Cells were then lysed with lysis buffer (acidified IPA) and the absorbance was measured at 570 and 620 nm using a Beckman Coulter AD340 plate reader (Indianapolis, Ind., USA). Percent viability was determined by normalization of the 570/620 absorbance ratio to the control untreated cells and positive control dead cells.

Figure 5:
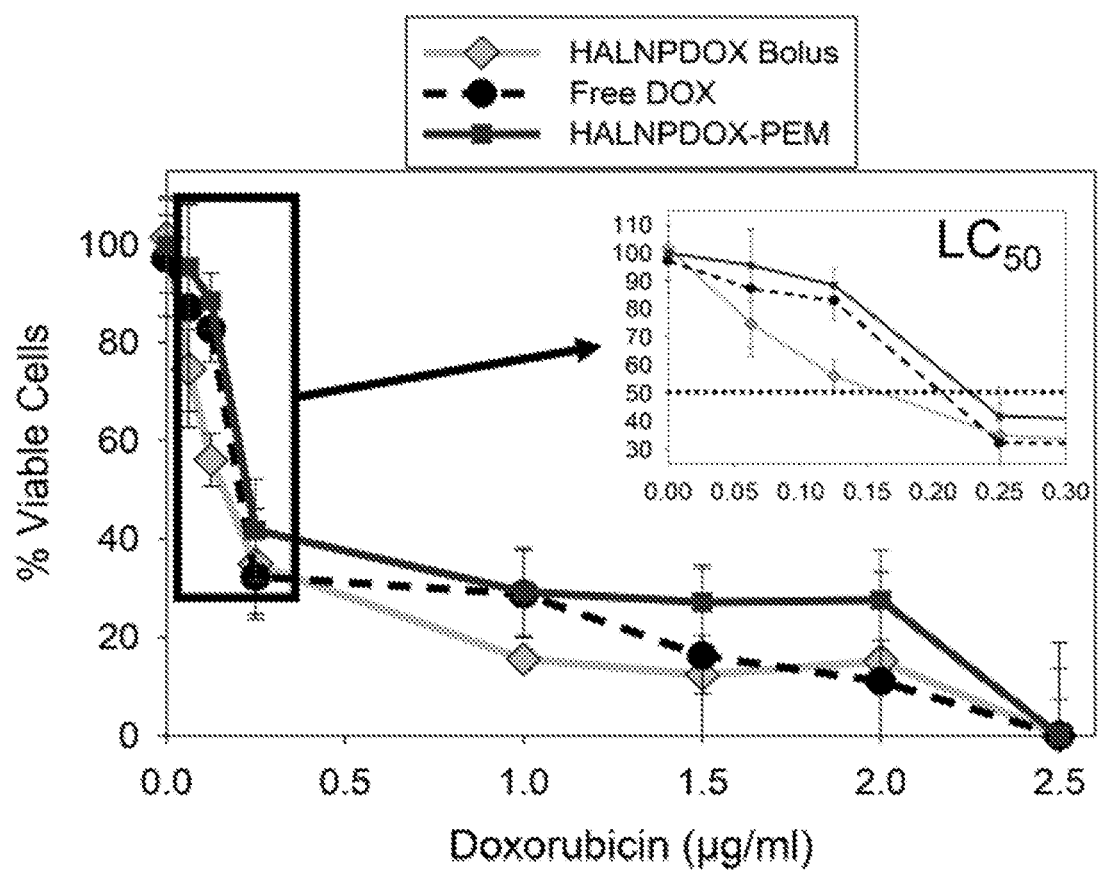
FIG. 5 shows results of a doxorubicin potency assay comparison between Free Dox, DOX encapsulated in HALNPs (HALNPDOX) in the bolus form, and HALNPDOX nanoparticles embedded into the PEM platform (HALNP-DOX-PEM). Standard MTT protocol was used to determine the % viable cells at 24 hours.

FIG. 5 and Table 3 each summarize the results determined from the potency assay (MTT assay) using 21MT-1 metastatic breast cancer cells (at 24 hours) comparing three distinct delivery methods: 1) free DOX, 2) bolus delivery of DOX encapsulated in the aqueous core of HALNP nanoparticles (HALNPDOX Bolus), and 3) HALNPDOX embedded into the (PLL/SPS)$_{4.5}$ base with capping layer (HALNP-DOX-PEM).

TABLE 3

Potency Assay Data

| Delivery Method | LC$_{50}$ (µg/mL) |
| --- | --- |
| Free DOX | 0.191 ± 0.0301 |
| HALNPDOX Bolus | 0.136 ± 0.0248 |
| HALNPDOX-PEM | 0.197 ± 0.0237 |

The HALNPDOX achieved higher potency due to the potentially faster uptake by the cancer cells compared to free DOX and HALNPDOX-PEM. It is hypothesized that the HALNPDOX-PEM platform has a higher LC$_{50}$ value compared to HALNPDOX bolus because at 24 hours not all HALNPs immobilized within the PEM films are released. As a control, a potency assay on empty HALNPs (no DOX) was performed to demonstrate that the lipid nanocarrier is a non-toxic delivery system. The DOX potency assay validated that the HALNP-PEM system is a useful platform for a controlled release of drugs encapsulated within the HALNPs without negatively affecting the potency of the drug.

Figure 6:
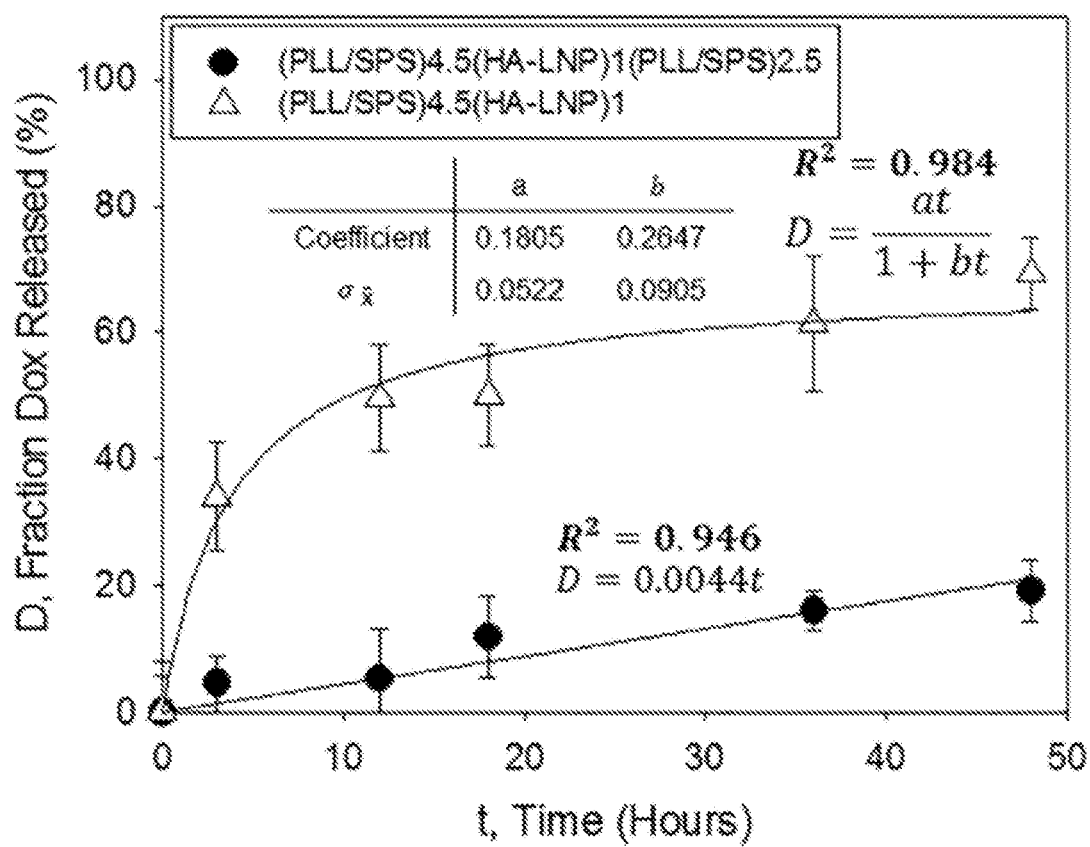
FIG. 6 shows DOX release profile from the non-capped $[(PLL/SPS)_{4.5}(HALNP)]$ and capped $[(PLL/SPS)_{4.5}(HALNP)(PLL/SPS)_{2.5}]$ HALNP-PEM platforms as a function of time utilizing the natural fluorescence of the chemotherapeutic agent for quantification.

Next the release profile of DOX from the HALNPDOX-PEM was investigated with and without the capping layer. The release of DOX in both the supernatant and the PEM platform was monitored via fluorescence as a function of time, as shown in FIG. 6. It was observed that without the capping layer, DOX was released from the PEM surface in a burst release fashion leading to over 60% release by 36 hours. The addition of the capping layer to the HALNP-PEM platform altered the DOX release kinetics and led to a linear release profile almost identical to the empty fluorescent HALNP release, signifying that the majority of DOX released was associated with a HALNP nanocarrier. This data further demonstrates that the capped PEM platform is an improved system for the controlled and linear release of therapeutic cargo.

In an additional example, 21MT-1 cells were transfected following the previously stated protocol with either HALNP mediated delivery of miR125a-5p (50 pmol) or HALNP mediated delivery of scramble miR (50 pmol). 72 hrs post transfection, the cell media was removed and 5 mg/mL MTT salt was added and incubated for two hours at 37° C. The cells were then lysed with lysis buffer (acidified IPA) and the absorbance was measured at 570 and 620 nm using a Beckman Coulter AD340 plate reader (Indianapolis, Ind., USA). The change in proliferation was determined by normalization of the 570/620 ratio to the control untreated cells.

Figure 7A:
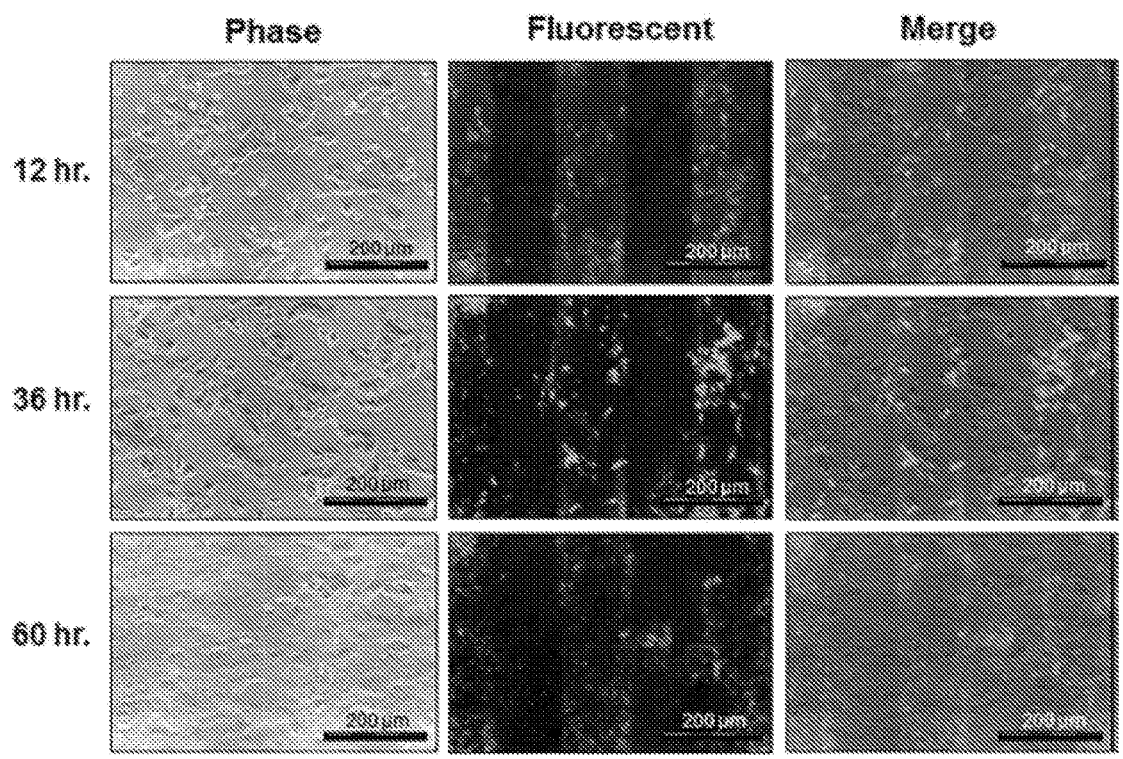
FIG. 7A shows phase contrast and fluorescent microscopy images of 21MT-1 metastatic breast cancer cells adhered to the HALNP-PEM system to visually probe both the temporal and spatial release of the HALNP nanocarrier. Capillary force lithography (CFL) was used to pattern PLL and create long range order of fluorescently tagged HALNP.

Example 13. Spatial Control of HALNP Immobilization on the HALNP-PEM Platform Enables Local Delivery To decipher the mechanism of HALNP delivery from the HALNP-PEM platform to cells, the spatial uptake of the nanocarrier was investigated. The purpose of this experiment was to determine if preferential uptake will occur with 21MT-1 breast cancer cells seeded on top of the HALNP patterns compared to the cells attached on the non-HALNP areas. CFL was used to pattern HALNPs tagged with green fluorescence atop PEM base films. 21MT-1 cell adhesion to the HALNP patterned PEM system with and without the capping layer signified that the capping layer mitigates heterogeneous cell attachment. At 12 hours post cell seeding, pattern dependent cellular uptake with the cells atop the HALNP patterns having higher uptake of the particles compared to those not on the patterns was observed, as shown in FIG. 7A. At 36 hours, the localized cellular uptake of HALNPs above the patterned layers was maintained. At 60 hours, the localization of the pattern was partially dispersed due to the proliferation and migrating metastatic breast cancer cells. This experiment further strengthened the hypothesis that the HALNP-PEM provides local delivery via a cell dependent uptake mechanism.

Figure 7B:
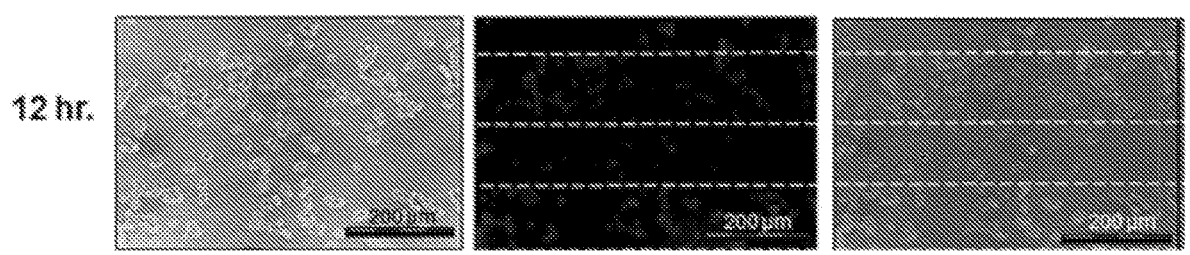
FIG. 7B shows phase contrast and fluorescent microscopy images of 21MT-1 metastatic breast cancer cells adhered to the HALNP-PEM system to visually probe both the temporal and spatial release of the HALNP nanocarrier. Capillary force lithography (CFL) was used to pattern PLL and create long range order of HALNPDOX patterns via preferential nanoparticle adsorption.

The same experiment was also performed using DOX encapsulated inside the patterned HALNP-PEM system to determine if the local delivery of an active therapeutic was also possible using a liposome embedded PEM platform. First, HALNPDOX was adsorbed onto the patterned PLL followed by subsequent addition of the capping layer. 12 hours after seeding of 21MT-1 cells, a local uptake of the HALNPDOX particles was dependent upon the nanoparticle deposition pattern was observed, as shown in FIG. 7B. A time point of 12 hours was selected to demonstrate the spatial release and uptake of DOX by the cells residing atop the HALNP embedded regions and to ensure the cells were still alive.

Example 14. Fluorescent Microscopy and Plate Reader Quantification of HA-LNP-FD Delivery to Breast Cell Lines 21MT-1, SKBR3, and MCF10A cells were plated in 12 well plates at a seeding density of 100,000 cells/well and left overnight in complete media to facilitate cell attachment. The next morning the media was switched to incomplete media and 70 pmol of 20 kDa FD either encapsulated inside HALNPs or in the free form (i.e., no nanocarrier) was added to designated wells. After a 5-hour incubation time, the cells were washed three times with 1xPBS followed by visualization with a fluorescent microscope and quantification of FD uptake by a fluorescent plate reader. Both the HA-LNP-FD and free form FD samples were compared to control cells with no FD added.

Example 15. Live Cell Confocal Microscopy

Two separate experiments were performed using live cell confocal microscopy: 1) intracellular delivery of 20 kDa FD by HA-LNPs; and 2) analysis of the intracellular fate of the HA-LNPs following endocytosis. In both cases, 21MT-1 cells were grown to 80% confluency on 35 mm glass bottom dishes (Mattek). Experiment 1) followed analogous procedures previously described involving cellular incubation with 165 pmol of 20 kDa FD encapsulated inside HALNPs for five hours. Experiment 2) employed HALNPs tagged with 0.15 mass % Top Fluor Cholesterol (Avanti) in the lipid bilayer as a tracker, a five hour incubation of the tagged particles with 21MT-1 cells, and lysosome staining by Lysotracker Red DND 99 (Life Technologies). In both experiments the cellular nuclei were stained by Hoescht Nuclear Stain 33342 (Pierce). Following the HA-LNP-FD or HA-LNP-tagged incubation and subsequent staining procedure, the cells were washed three times with 1xPBS and visualized with an Inverted confocal microscope (Olympus IX 81) at the UNL Microscopy Core Research Facility.

Example 16. Competition Assay (HA Pre-Treatment)

21MT-1 cells were seeded in a 12 well plate with a seeding density of 100,000 cells/well and incubated overnight to stimulate attachment. The next morning, 250 µg HA was added to select wells and incubated for 1 hour at 37° C., 5% CO$_2$ (pre-treatment procedure). Following this one-hour incubation, 85 µg/well of fluorescently conjugated HALNPs was added and the cells were further incubated for five hours. Flow cytometry analysis was then used to compare the delivery efficiency between HA pre-treated and non HA pre-treated cells.

Example 17. Transfection of 21MT-1 Cells

21MT-1 cells were seeded onto 12 well tissue culture plates at a seeding density of 60,000 cells/well in 21MT-1 Complete Media and left overnight. The next day the cells were washed and the media was switched to 21MT-1 Incomplete Media. Following entrapment of miR125a-5p by the HA-LNP platform, quantification of internal miRNA cargo, and subsequent removal of un-entrapped miR by centrifugation, the HALNP-miR125a-5p conjugate was filter sterilized through a 0.44 micron filter, and 50 pmol HALNP entrapped miR125a-5p was gently added to designated wells. In addition, an analogous amount of HALNP with no miRNA was added to neighboring wells as a negative control, and two sample types of Lipofectamine 2000 (Life Technologies, LF2K) were administered: 1) a low dose (50 pmol) of miR125a-5p to compare to the HALNP system; and 2) a high dose positive control (150 pmol), both following standard protocol per the manufacturer's instructions for transfection. To further compare transfection efficiency with LF2K, a 150 pmol HALNP-miR125a-5p "high dose" was also used. Additionally, a scramble miR negative control (150 pmol) was encapsulated and delivered with the HALNP system to validate the specificity of the silencing interaction. The delivery systems and controls were incubated with the 21MT-1 cells for five hours to mediate transfection. Following the five hour incubation time, the cells were washed once with 1×PBS, supplemented with fresh 21MT-1 complete media, and placed in the incubator (represented as time point=0 hr).

Example 18. Western Blotting

Total protein was extracted at the 72-hour time point from the 21MT-1 cell line by standard protocol including RIPA buffer induced cell lysis and protein solubilization followed by the scraping method. Western blotting was used to determine the effect of miR125a-5p transfection on the 21MT-1 cell line protein expression levels. All proteins besides ERK1/2 and phospho-ERK1/2 were tested and probed on 7.5% tris-glycine SDS PAGE homemade gels. The ERK1/2 proteins were probed on 15% homemade gels to resolve the 42 and 44 kDa double band. Coomassie blue reagent (Thermo Scientific) was used to quantify total protein concentration and 10 µg total protein lysate was loaded per lane. The primary antibody information used for all the proteins is as follows in order from smallest to largest molecular weight: Anti-GAPDH (Millipore; ABS16) 1:4000 Rb, Anti-Phospho-ERK1/2 (Millipore; 05-797R) 1:1000 Rb, Anti-ERK1/2 clone MK12 (Millipore; 05-1152) 1:1000 M, Anti-Tubulin (Abcam; ab44928), Anti-Phosphor-AKT (Ser473) (Millipore; 05-1003) 1:1000 M, Anti-AKT/PKB PH Domain (Millipore; 05-591) 1:1000 M, Anti-CD44 (Abcam; ab103552), Anti-PI3K (Millipore; 05-217) 1:1000 M, Anti-HER2 (Abeam; ab2428) 1:1000 Rb, and Anti-Ki-67 (Millipore; AB9260) 1:1000, Rb. The secondary antibodies used were Goat Anti-Rabbit-HRP (Santa Cruz; sc-2030) 1:5000 and Goat-Anti-Mouse-HRP (Santa Cruz; sc-2031) 1:5000. Protein bands were quantified by use of Image J Software (NIH). All protein quantification data was performed on at least three biological samples. M=mouse, and Rb=rabbit.

Example 19. RNA Isolation and qRT-PCR

Total RNA was extracted from the 21MT-1 metastatic breast cancer cell line at 72 hours post transfection using Trizol (Life Technologies) and following standard RNA extraction protocol. RNA quantity and quality was assessed by a NanoDrop (Thermo Scientific) UV/VIS spectrophotometer, cDNA was made with iScript Reverse Transcription Supermix for qRT-PCR (Bio-Rad), and a RealPlex thermocycler (Eppendorf) was used to create cDNA (5 min 25° C., 30 min 42° C., 5 min 85° C.). Following cDNA creation, qRT-PCR was performed by using the SYBR Green Master Mix (Life Technologies), and a per-reaction use of 500 nM of both the forward and reverse primers with 10 ng of cDNA. The qRT-PCR was performed with a 40 cycle amplification (95° C. for 10 seconds, 56° C. for 30 seconds, and 72° C. for 30 seconds) and a threshold intensity of 50 (during linear phase). The primers used for the qRT-PCR analysis are as follows:

```
Human GAPDH:
                                   (SEQ ID NO: 1)
   (R: 5'-AGG-GGC-CAT-CCA-CAG-TCT-TC-3');

(SEQ ID NO: 2)
   (F: 5'-AGA-AGG-CTG-GGG-CTC-ATT-TG-3')

Human HER2:
                                   (SEQ ID NO: 3)
   (R: 5'-TGA-TGA-GGA-TCC-CAA-AGA-CC-3');

(SEQ ID NO: 4)
   (F: 5'-AAC-TGC-ACC-CAC-TCC-TGT-GT-3').
```

The ΔΔCt Method was used to calculate changes in gene expression, and at least three biological samples were analyzed.

Example 20. In Vitro Migration Assay

21MT-1 cells were transfected as previously described and plated into new 12 well plates as confluent monolayers. Three vertical scratches were made per well and cell debris was washed away with 1×PBS prior to taking the time=0 h photos. Additional photos were taken at 24 h and 48 h time points. The cells were supplemented in complete 21MT-1 media for the entire migration assay. ImageJ was used to quantify the scratch width (arbitrary units) changes at each time point. A total of 27 scratch width data points were taken for each sample type at each time point (3 scratches per well×3 pictures per scratch×3 biological duplicates per sample type).

Example 21. Model Drug System for Delivery to Breast Cancer Cells

Figure 9A:
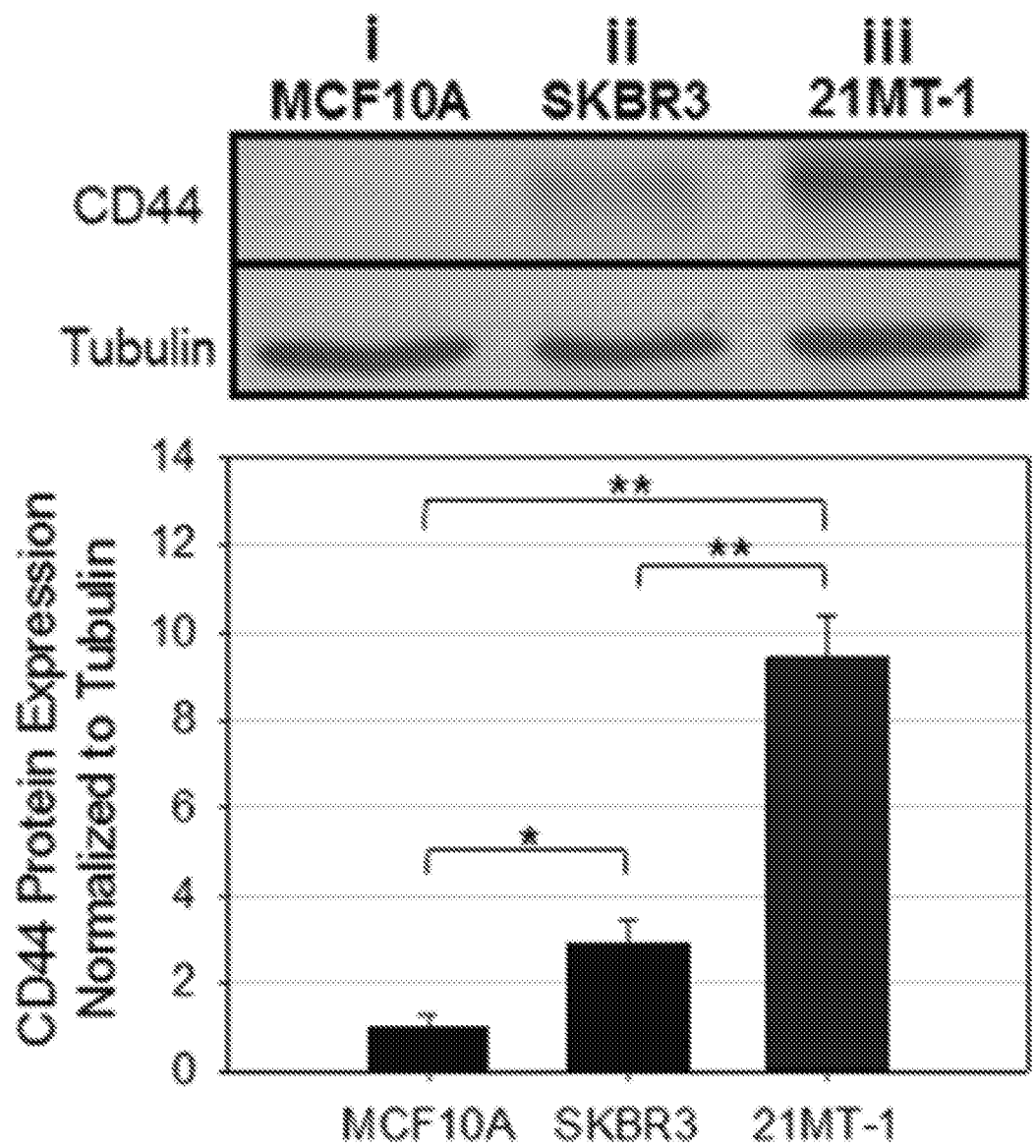
FIG. 9A shows Western Blot data of CD44 protein expression in (i) MCF10A (normal breast tissue), (ii) SKBR3 (HER2+ invasive breast cancer), and (iii) 21MT-1 (HER2+ metastatic breast cancer) cell lines. 20 kDa FD model drug systems were utilized in two distinct forms: (1) encapsulated inside the aqueous core of HALNPs and (2) naked drug (i.e. free form drug, not conjugated with LNPs).

To investigate the relationship between CD44 expression and HA as a possible targeting moiety to deliver LNPs, FD was used as a model drug. FD is fluorescently tagged, impermeable to cell membranes, and can be polymerized to a range of molecular weights to model a variety of therapeutic molecules. Because the molecular weight of miRNA is typically in the range of 14-19 kDa, 20 kDa FD was used as a model for miRNA encapsulation and intracellular delivery by the HALNP system. Three developmentally distinct human breast cell lines were used for nanoparticle uptake analysis: 1) MCF10A (normal mammary epithelial cells), 2) SKBR3 (HER2+ invasive breast cancer cells), and 3) 21MT-1 (stable patient-derived metastatic breast cancer cells isolated from the metastatic pleural effusion). In addition to representing three distinct stages of breast cancer progression, the three breast cell lines show differential expression profiles of CD44, as shown in FIGS. 9A-9C.

Figure 9B:
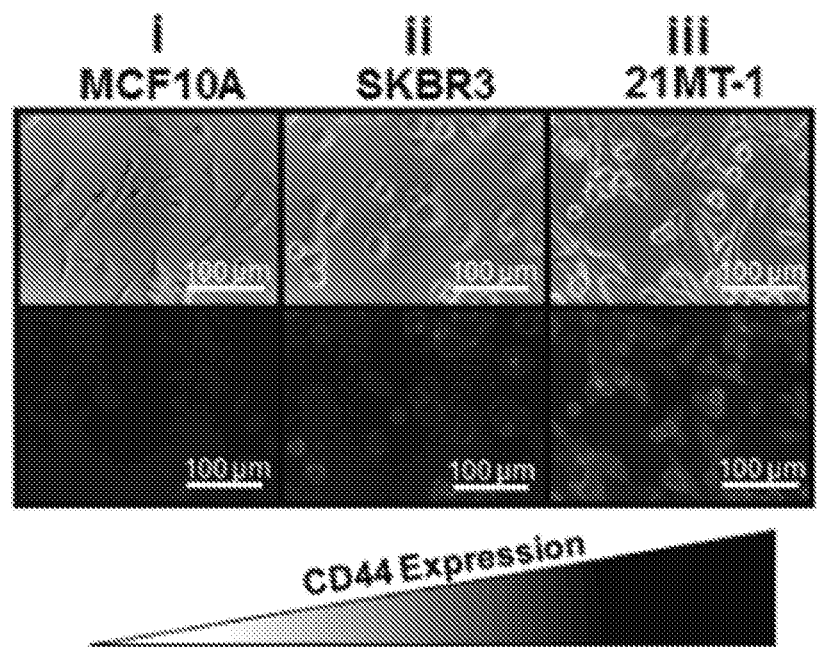
FIG. 9B shows fluorescent and phase contrast microscopy images of HALNP mediated FD delivery to three breast cell lines.
Figure 9C:
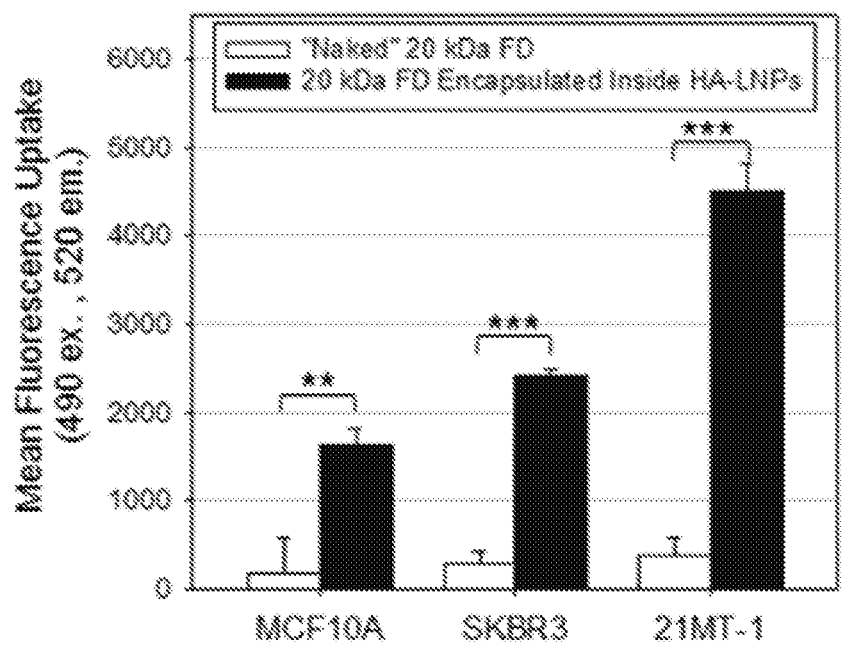
FIG. 9C shows plate reader quantification at 490 nm excitation/520 nm emission of the FD uptake in both the naked and HALNP encapsulated drug forms.
Figure 9D:
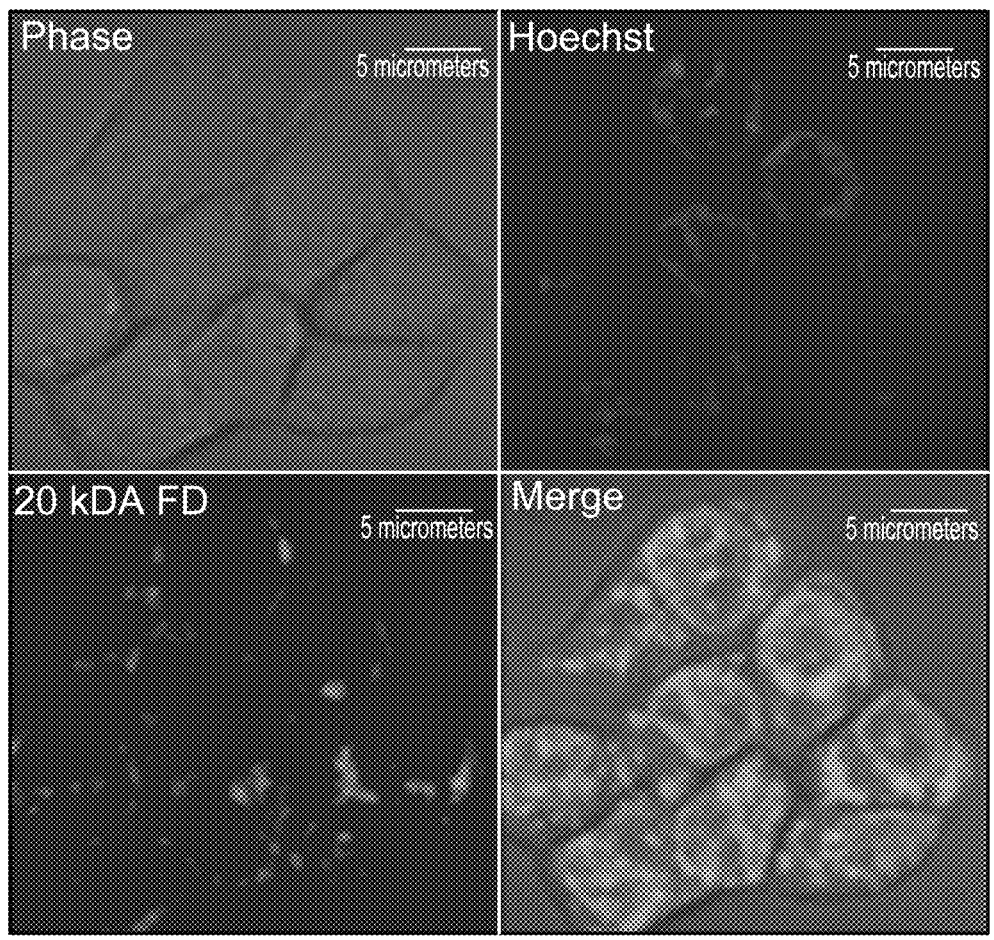
FIG. 9D shows live confocal microscopy images of a cluster of 21MT-1 breast cancer cells at 100× magnification with optical zoom (Scale bars are 5 μm). The live confocal microscopy images were used to confirm the intracellular delivery of the FD cargo.
Figure 9E:
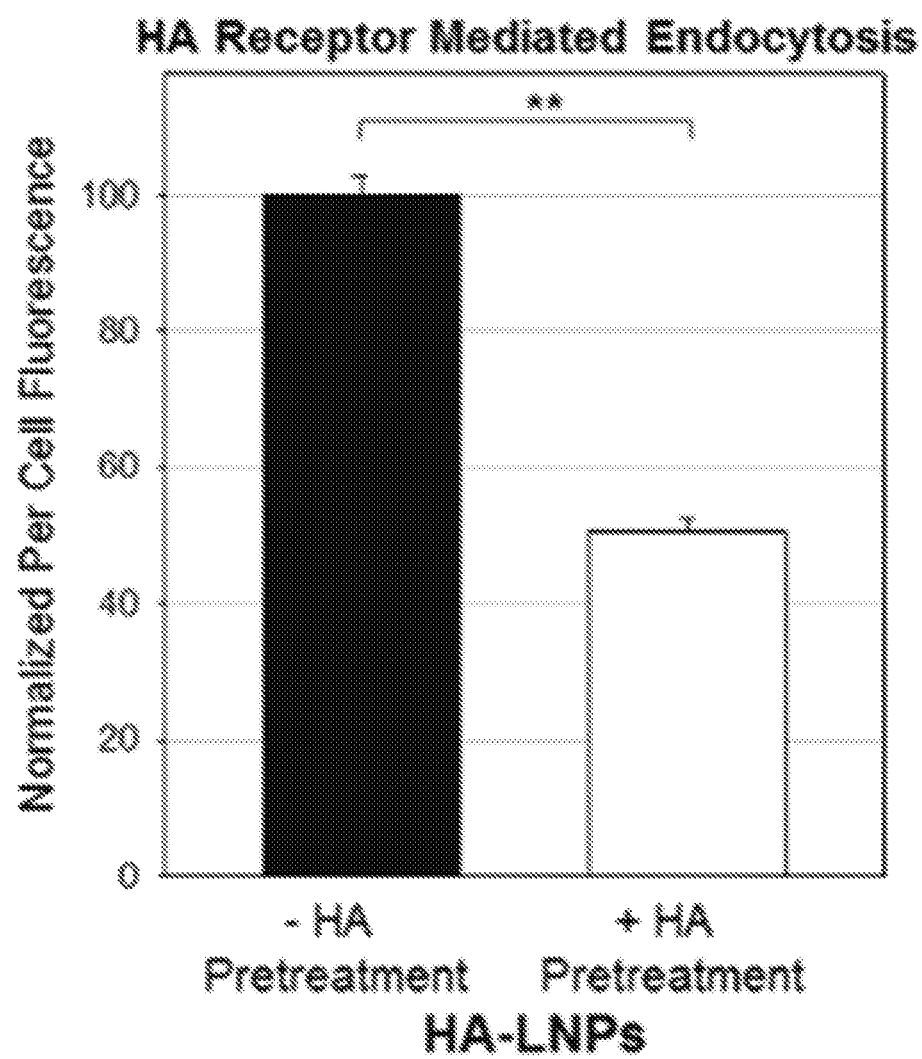
FIG. 9E shows a representative competition assay in 21MT-1 cells.

The cancer cell lines were first incubated with either the free form FD drug (i.e., no HALNP) or with an equivalent amount of 20 kDa FD encapsulated inside HALNPs, and compared the uptake qualitatively using a fluorescent microscope as shown in FIG. 9B, and quantitatively using a plate reader as shown in FIG. 9C. It was observed that the fluorescence intensity was significantly higher in all three cell types when FD was delivered using HALNPs as compared to free form delivery. Furthermore, the metastatic cell line had the highest fluorescence intensity compared to other cell lines indicating that the uptake of the LNPs was highest in the metastatic cells. This experiment validated that the strong correlation between uptake of the HALNP-FD particles and the degree of the breast tissue malignancy. Live confocal microscopy was also performed with the 21MT-1 cell line following incubation with HALNP-20 kDa FD, as shown in FIG. 9D, to show intracellular delivery of the cargo was achieved. In addition, a competition assay with the 21MT-1 cells via pre-treatment with excess HA before addition of the HALNPs was performed, and a 55% decrease in HALNP uptake was observed as shown in FIG. 9E.

Figure 9F:
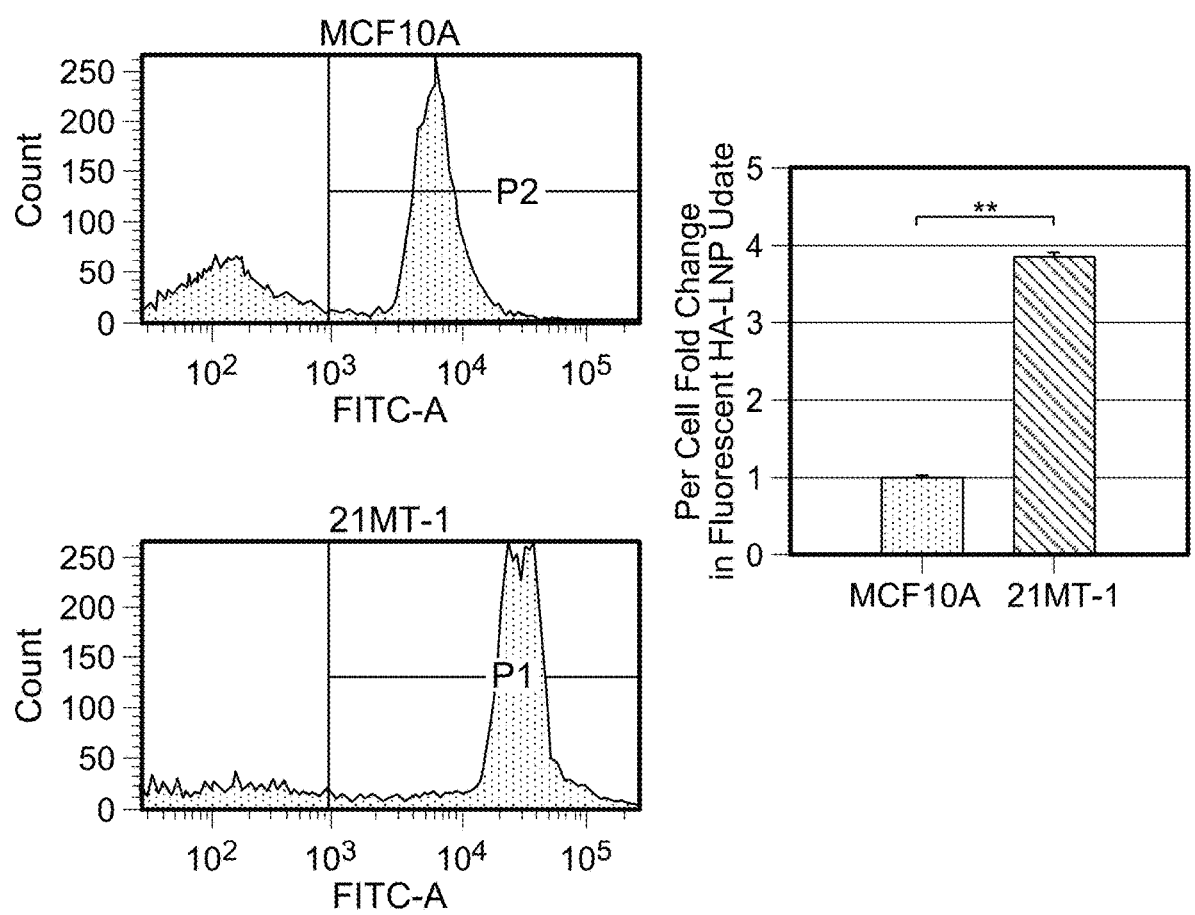
FIG. 9F shows flow cytometry assessment of per cell uptake of fluorescent conjugated HALNPs between MCF10A and 21MT-1 to validate uptake into the metastatic cells compared to normal cells. All experiments: *$P<0.05$, $P<0.005$, *$P<0.0001$; n=3.

To further validate the targeting and subsequent preferential uptake of the nanocarrier to CD44 positive cells, flow cytometry analysis was performed between 21MT-1 and MCF10A cells to determine the per cell uptake of HALNPs fluorescently tagged with 0.15 mass % green fluorescent cholesterol in the lipid bilayer as shown in FIG. 9F. An approximate four-fold increase in HALNP uptake was observed in the 21MT-1 cell line over the MCF10A cell line on a per-cell basis, corroborating the targeting potential observed in the FD uptake studies.

Example 22. Lysosomal Degradation and Cellular Cytoplasm Dispersion

Figure 10A:
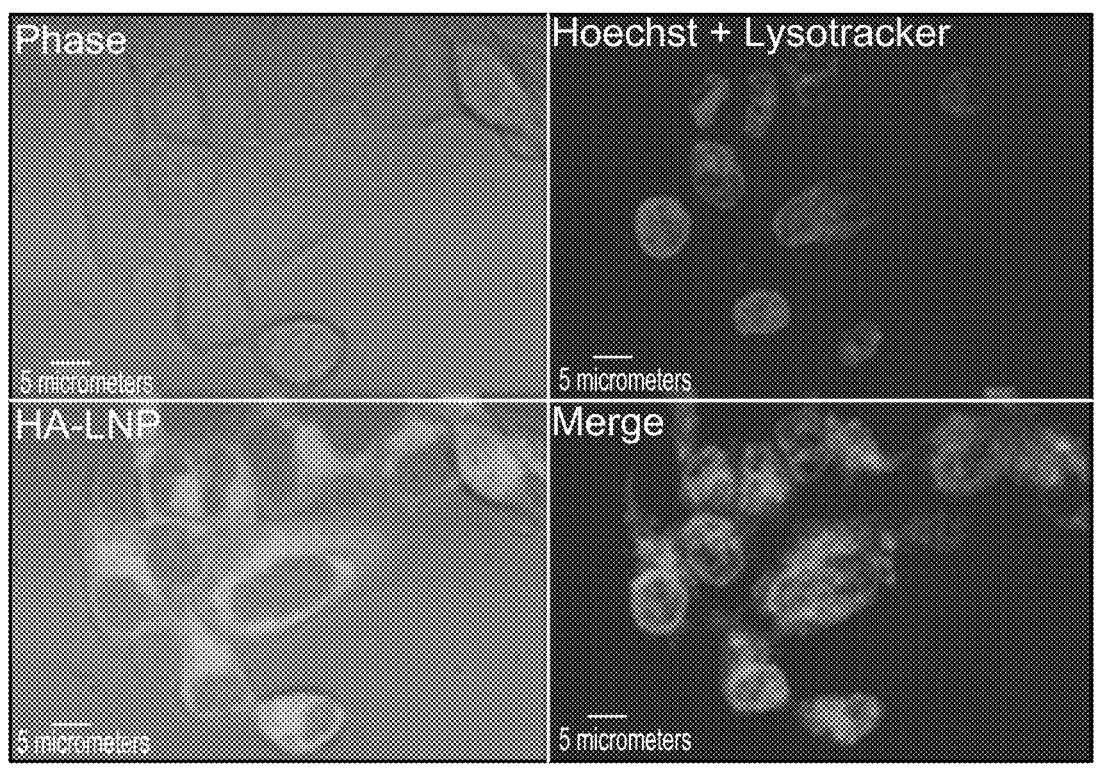
FIGS. 10A-10B shows live confocal microscopy analysis of HALNP localization in 21MT-1 metastatic breast cancer cell line in vitro. HA-LNPs with 0.15 mass % FITC tagged cholesterol in the lipid bilayer of the nanoparticles was used to track nanoparticle-endocytosis into the cell.
Figure 10B:
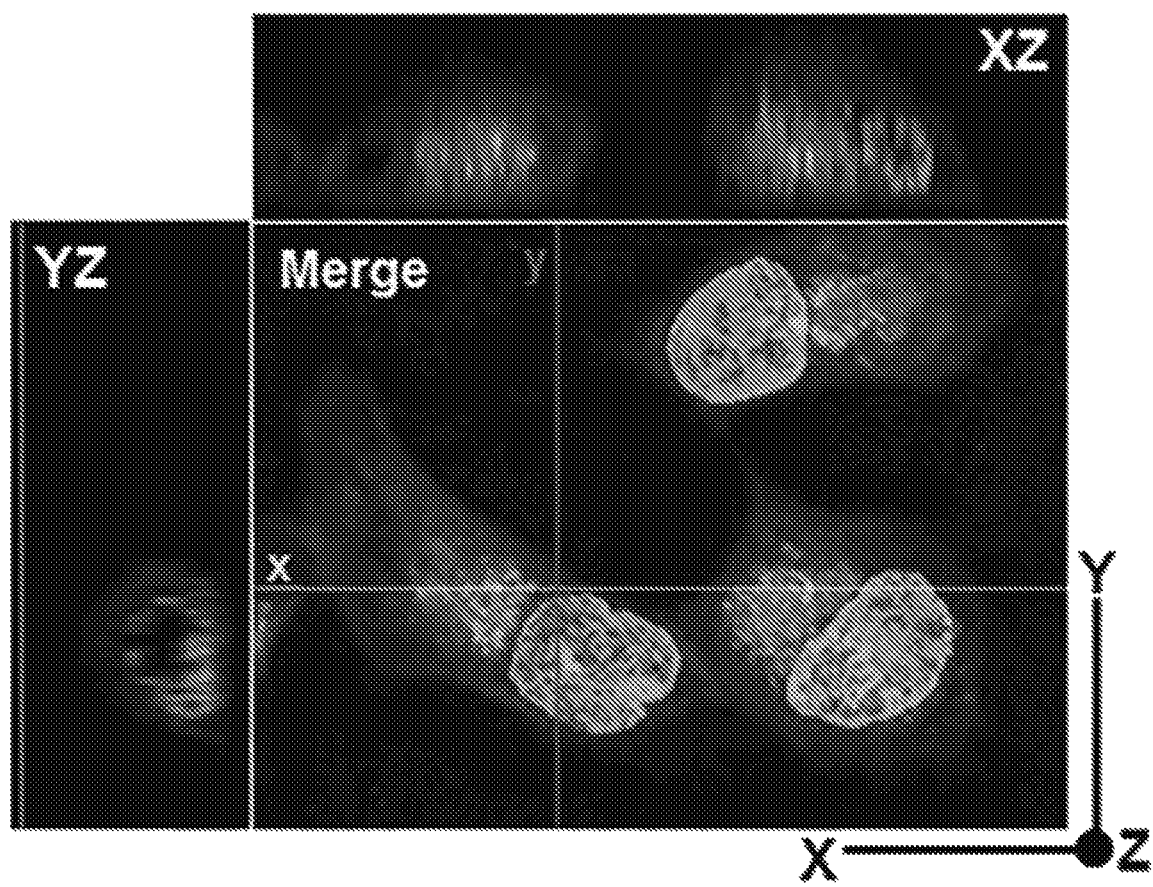

Because the RNAi pathway of gene silencing requires the miRNA to be cytosolic, the localization of the HALNPs following the CD44 mediated endocytosis event was investigated. To do so, the green fluorescent cholesterol tagged HALNPs were analyzed using live confocal microscopy to determine the cellular fate. 21MT-1 cells were plated, incubated with tagged HALNPs, stained cellular lysosomes (a main degradation pathway for nanoparticles) red, and found minimal co-localization between the lysosomes and the HALNPs, as shown in FIG. 10A. In addition, it was found that the HALNPs were homogenously dispersed in the cellular cytoplasm, signifying endosomal escape. To validate that the HALNPs were cytosolic, a z-axis transformation was performed to construct a side profile view of the cells, as shown in FIG. 10B (XZ plane view: the bottom of the XZ plane is the contact point between the cells and the petri dish). The nucleus was used as an internal reference point to validate the nanoparticles were cytosolic and not residing on the outer cellular membrane. In the z-axis transformation analysis, the HALNPs also appeared uniform in dispersion with virtually no co-localization with lysosomes.

Example 23. In Vitro Breast Cancer Proliferation and Migration

Figure 11A:
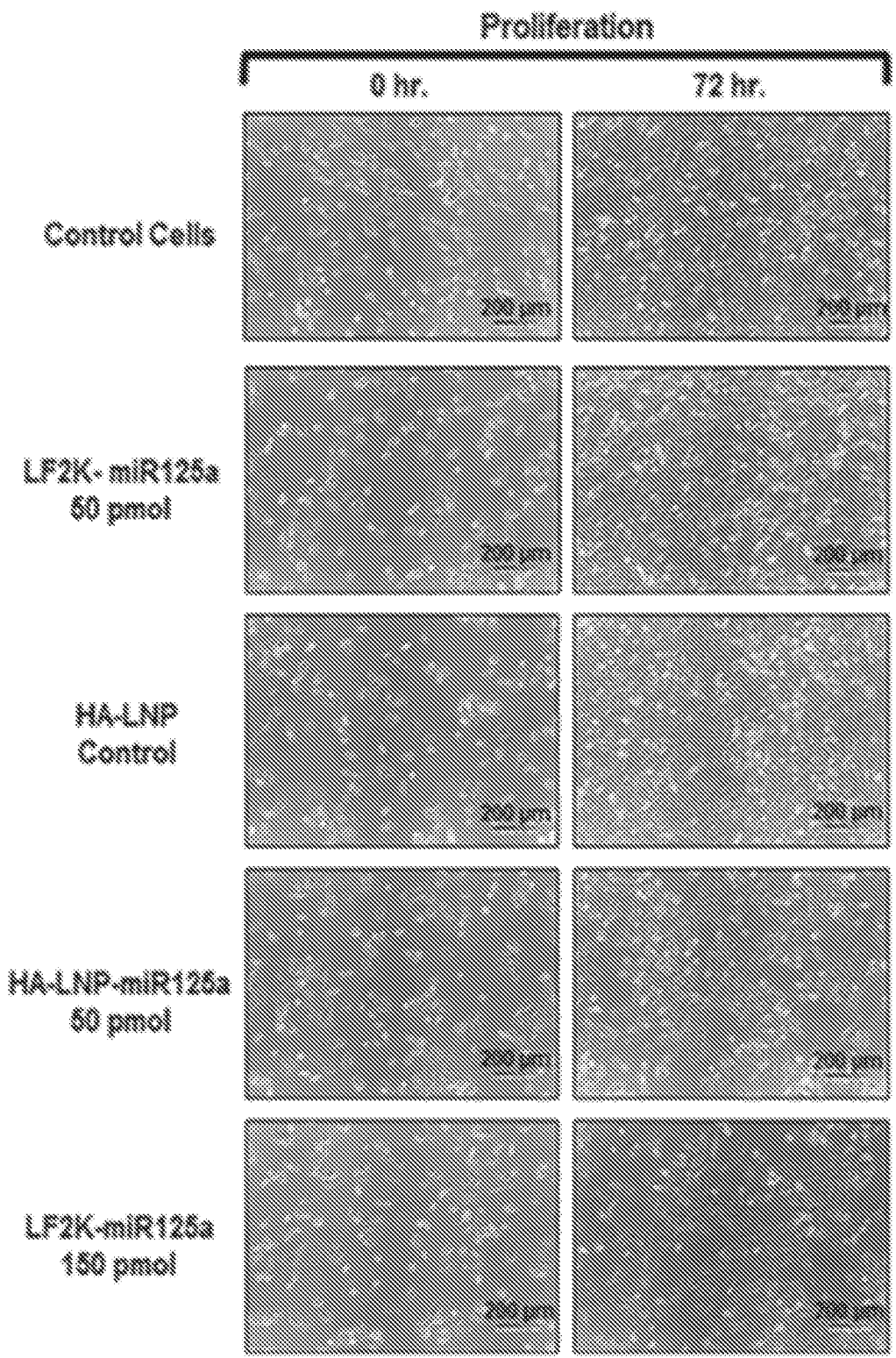
FIGS. 11A-11E show reduction of highly proliferative and migrant phenotype of 21MT-1 metastatic breast cancer cells following transfection with miR125a-5p in vitro.
Figure 11B:
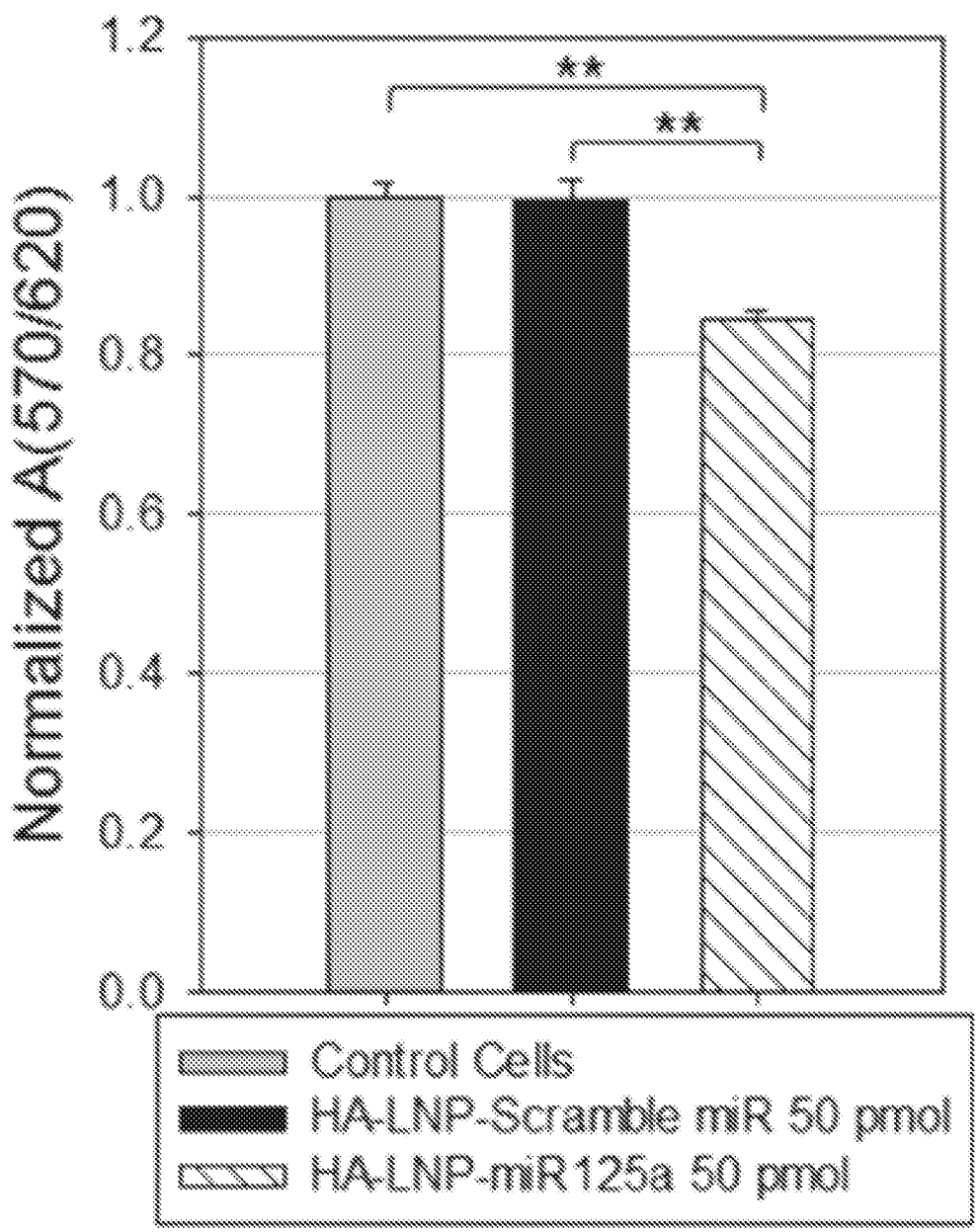

Following validation that the HALNPs have an active targeting mechanism as well as the ability to escape the intracellular endosome maturation pathway and achieve cytosolic delivery, the HALNPs were used to encapsulate human miR125a-5p mimic and transfect 21MT-1 metastatic breast cancer cells. The HALNP system was used to deliver 50 pmol/well miR125a-5p to 21MT-1 cells 24 hours after the cells were seeded. The HALNP mediated transfection was compared to Lipofectamine 2000 (LF2K), a standard commercial transfection reagent, with 50 pmol miR125a-5p for potency comparison with HALNPs and at a high dosage of 150 pmol miR125a-5p as a positive control. Empty HALNP particles were used both as a negative control and to confirm their biochemical inactivity. Potent suppression of cellular proliferation was observed at 72 hours post transfection as demonstrated by phase contrast images, as shown in FIG. 11A. To further support these findings, an MTT assay was performed comparing HALNP delivered miR125a-5p (50 pmol/well) and HALNP delivered scramble miR (50 pmol/well) to validate the capacity and specificity of miR125a-5p to reduce the hyper-proliferative phenotype of 21MT-1 cells, as shown in FIG. 11B. A significant decrease in cellular proliferation rate of over 15% was observed at 72 hours post transfection with miR125a-5p as compared to the control cells. The scramble miR had no effect on the metastatic cell proliferation rate.

Figure 11C:
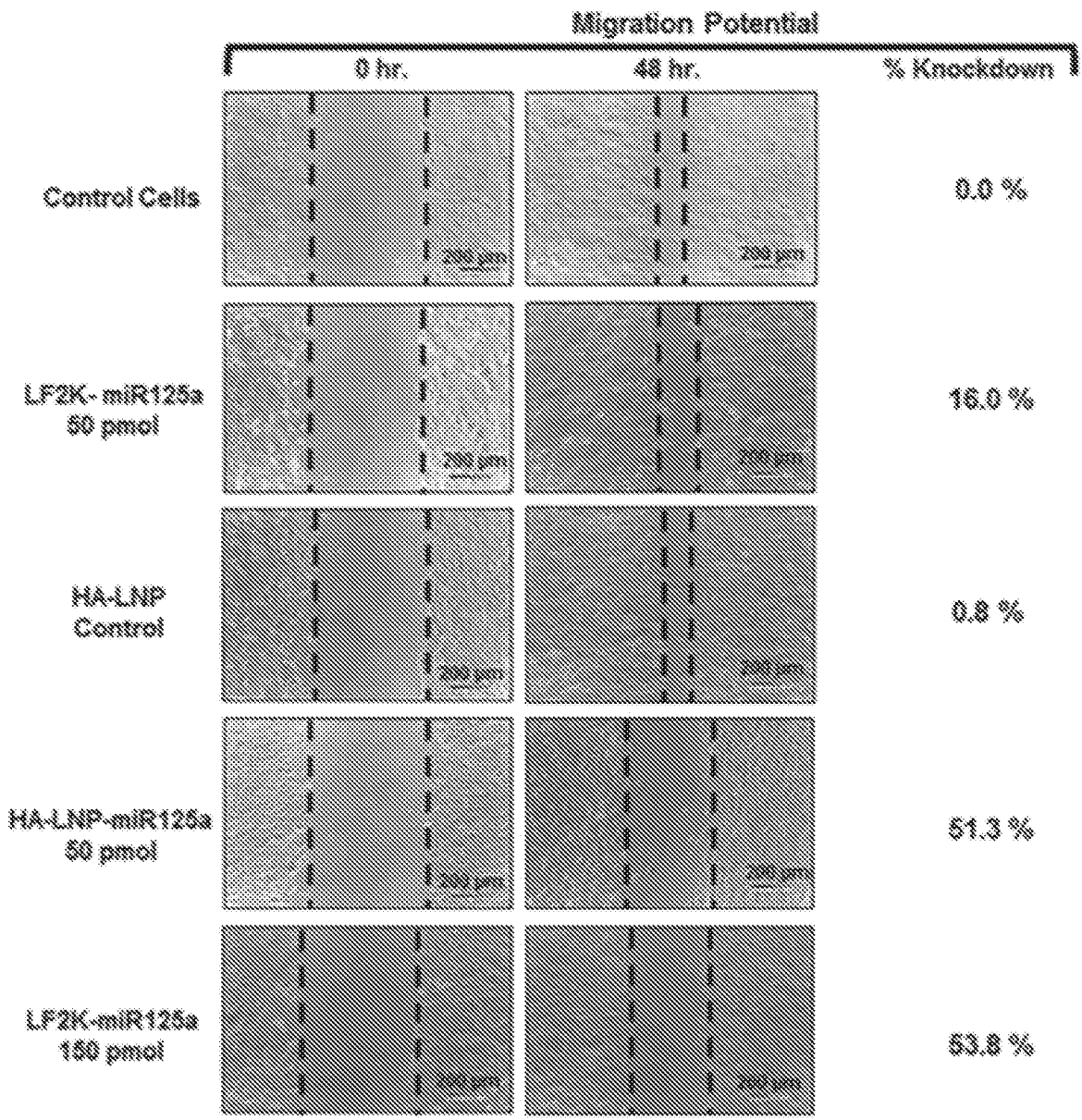
Figure 11D:
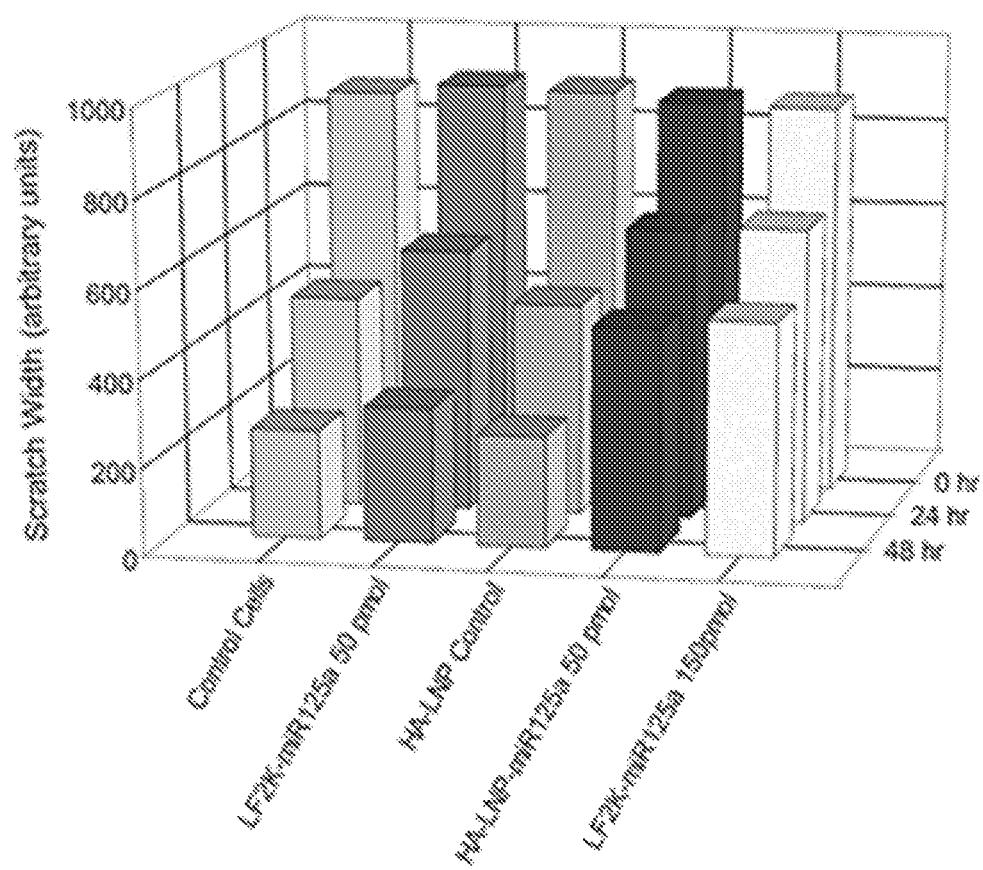
Figure 11E:
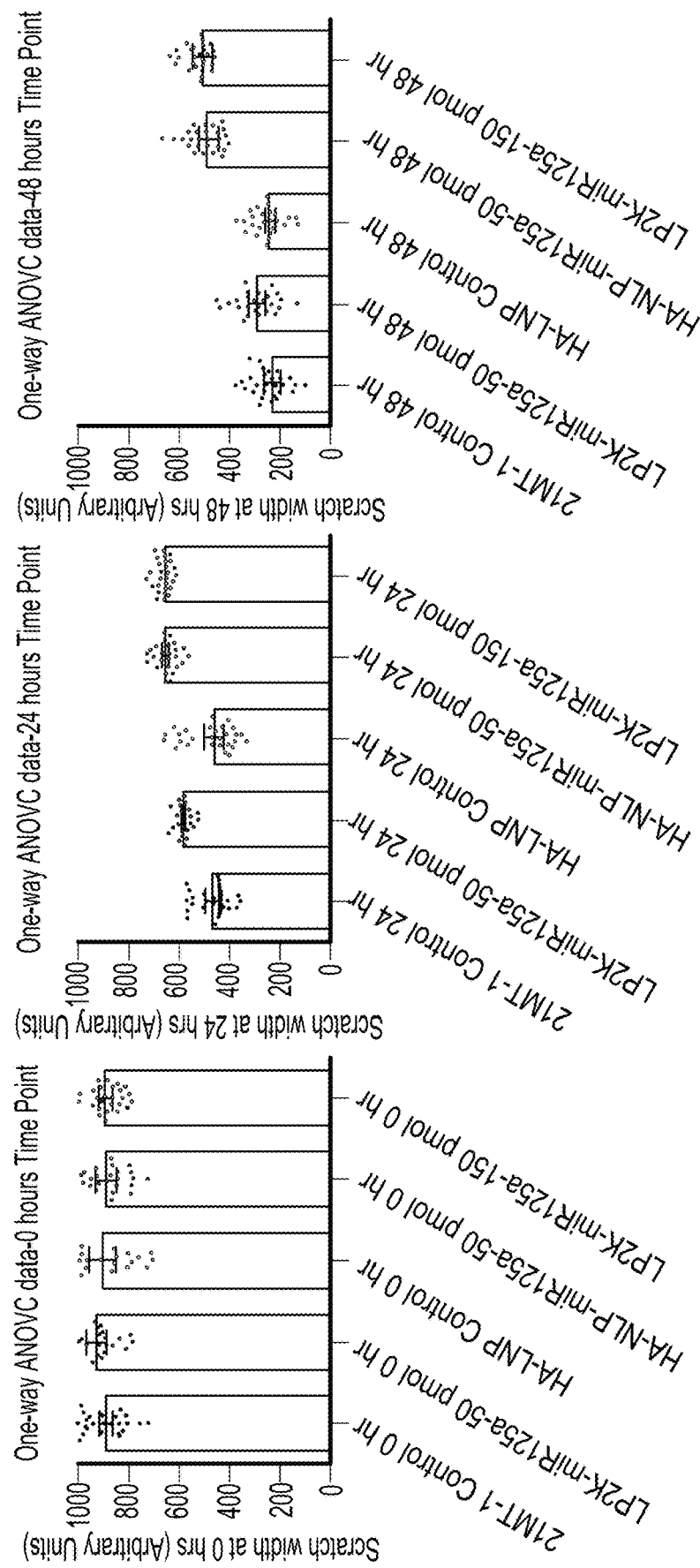

The effect of miR125a-5p on the migration potential of the metastatic breast cancer cells was also examined due to the connection between HER2 overexpression and increased cellular motility (see e.g., Grothey et al, *Oncogene,* 2000, 19:4864; Balz et al, *The Journal of Pathology,* 2012, 227: 234). Following an analogous 72-hour transfection period as described above, scratches were made in confluent monolayers and the wound healing potential (migration potential) of each sample type was analyzed as a time course study by an inverted microscope as shown in FIG. 11C. The HALNP-miR125a-5p and LF2K high dose positive control both showed over a 50% reduction in cellular migration as compared to the control cells, while the LF2K 50 pmol dose showed a 16% decrease and the HALNP control did not statistically affect cellular migration. A three dimensional graph depicting the change in scratch width as a function of time in each sample type (FIG. 11D) was created in conjunction with an Anova analysis (FIG. 11E) to clarify and substantiate the experimental results. By reducing the potential for cellular migration, the HA-LNP-miR125a-5p therapeutic system impedes a main driving force for metastasis (see e.g., Doyle et al, *Current Opinion in Cell Biology,* 2013, 25:642).

Example 24. HER2 Gene Knockdown

Figure 12:
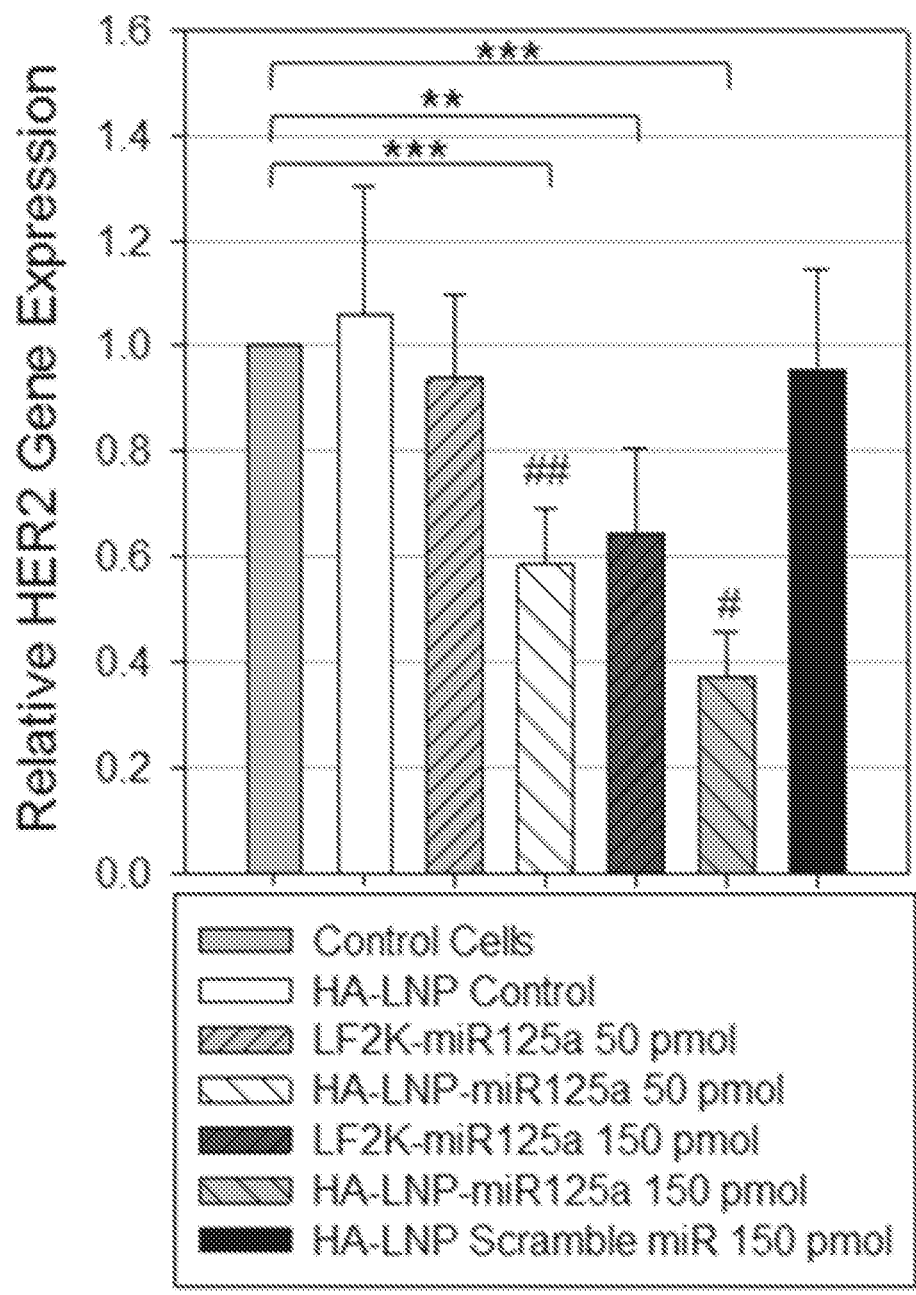
FIG. 12 shows qRT-PCR quantification of HER2 mRNA 72 hours post transfection with miR125a-5p. Scramble miR was used to validate the specificity of miR125a-5p to the HER2 mRNA sequence. GAPDH gene used as a normalization control (*$P<0.05$, $P<0.005$, *$P<0.0001$; n=4; # denotes significance between LF2K and HA-LNP at the analogous miR125a-5p concentration-following the same significance level designations as the stars (*). The ΔΔCt method was used to determine the change in mRNA expression FIGS. 13A-13B show Western blot analysis of the HER2 pathway in 21MT-1 cells 72 hours following transfection with miR125a-5p.

21MT-1 cells were transfected and qRT-PCR probing was performed for the HER2 oncogene 72-hours post transfection as shown in FIG. 12. To directly compare the transfection efficiency of the HALNP and commercially available LF2K, both 50 and 150 pmol miR125a-5p were delivered using both delivery systems. At 72 h, a 40% and 60% knockdown in the HER2 mRNA levels with 50 pmol and 150 pmol miR125a-5p delivered via HALNPs, respectively, was observed. Conversely, at 50 pmol miR125a-5p no knockdown was seen with LF2K and at 150 pmol only a 40% knockdown was achieved. To further confirm the knockdown of the HER2 mRNA was due to miR sequence specificity, 21MT-1 cells were transfected with 150 pmol scramble miR delivered via HALNPs and no gene silencing effect was detected at 72 h.

Example 25. Silencing HER2 Protein in Metastatic Breast Cancer Cells

Figure 13A:
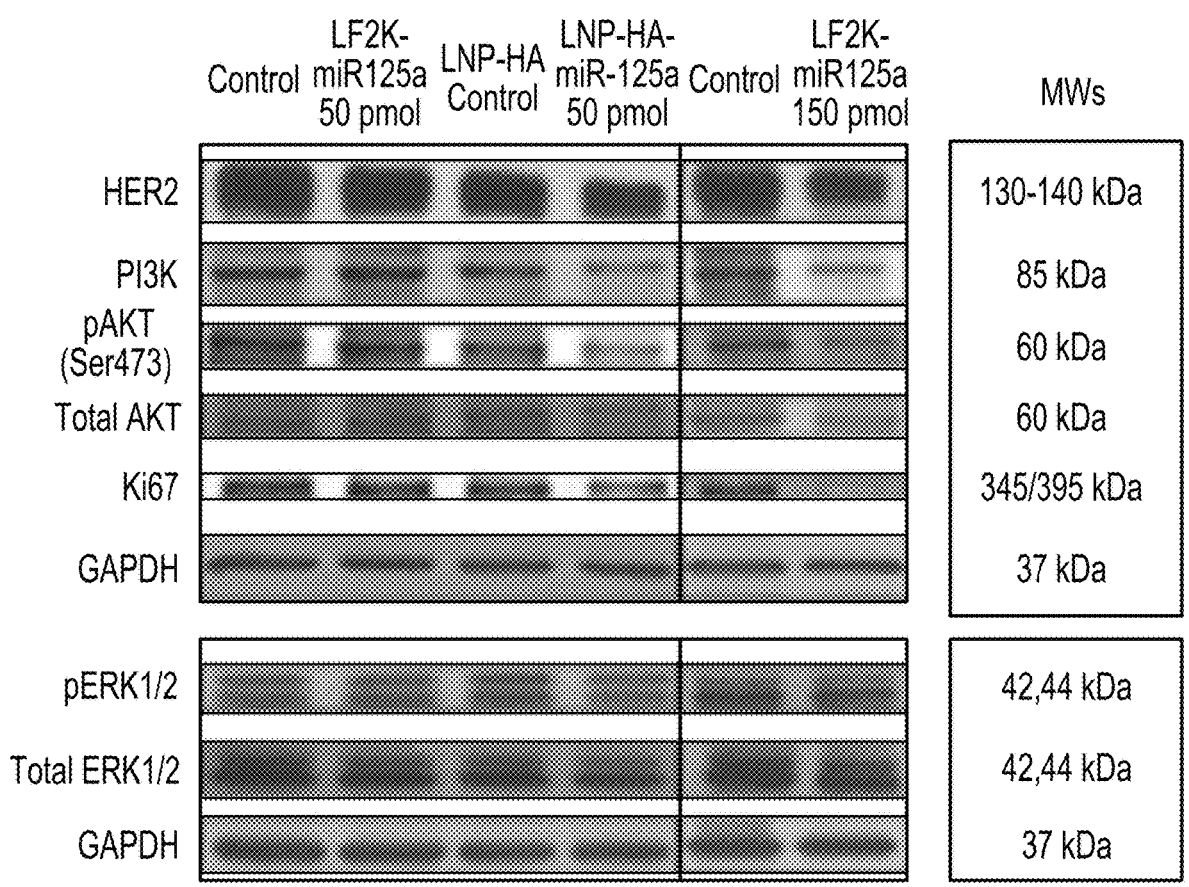
FIG. 13A shows Western blots and molecular weights of probed proteins.

To validate the application of the HALNP-miR125a-5p as a viable therapeutic for HER2+ metastatic breast cancer, the effect of miR125a-5p delivery on complex HER2 signaling was investigated. 21MT-1 cells were transfected with HALNPs and the resultant effect of miR-125a-5p on HER2 protein levels was probed via Western Blot. A 30% reduction in HER2 levels was observed when transfected with the HALNP-miR125a-5p system as compared to a 35% reduction with the LF2K high dose positive control as shown in FIG. 13A. Although this protein knockdown was less than that of previous studies using this miRNA to target HER2, this potent silencing effect was achieved without viral mediated cellular transformation (see e.g., Scott et al, J. Bio. Chem. 2007, 282:1479), performed with a nanoparticle system capable of in vivo application (see e.g. Nishida et al, Clin. Cancer Res. 2011, 17:2725), and utilized an overall low dose of miRNA compared to Lipofectamine.

Figure 13B:
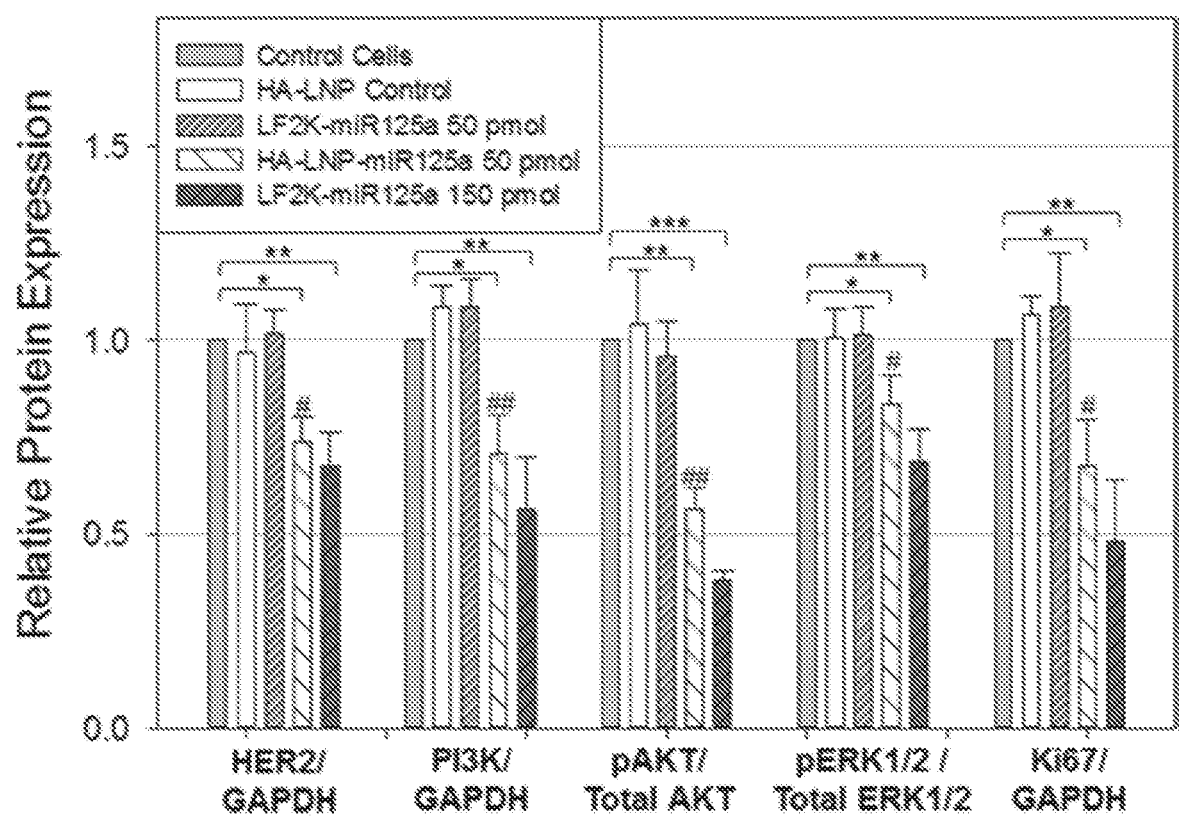
FIG. 13B shows quantification of the Western Bblot data (*$P<0.05$, $P<0.005$, *$P<0.0001$; # denotes significance between LF2K 50 pmol and HALNP miR 50 pmol, #=$P<0.05$, ##=$P<0.005$; n=3). Normalization controls used: GAPDH for HER2, PI3K and Ki67, total AKT for pAKT, and total ERK1/2 for pERK1/2.

Because the two most prominent paths of signal transduction for HER2 are the mitogen activated protein kinase (MAPK) and the phosphoinositide-3-kinase (PI3K/AKT) pathways (see e.g. Emde et al, Critical Reviews in Oncology/Hematology, 2012, Supplement 1:e49), and the fact that these pathways are commonly deregulated upon cancer onset, both pathways were probed to elicit the influence of the HA-LNP-miR125a system on the HER2 downstream signaling cascade as shown in FIGS. 13A-13B.

The PI3K/AKT pathway is involved in cell survival, proliferation, migration, and angiogenesis (see e.g., Balz et al, The Journal of Pathology, 2012, 227:234) and PI3K and AKT activity are inherently coupled because AKT binds to the product of PI3K, PIP3, leading to AKT threonine 308 phosphorylation (see e.g. Manning et al, Cell, 2007, 129: 1261; Huang et al, Biochemical Society Transactions, 2009: 37-217). Accordingly, knockdown of PI3K was investigated to validate the silencing of initial downstream targets of HER2. Following a 72-hour transfection period, a 35% and 40% knockdown of the protein levels of PI3K from the HALNP mediated miR125a-5p transfection and LF2K high dose positive control respectively was observed. Because additional phosphorylation of AKT at serine473 is required for full AKT activation (see e.g., Manning et al, Cell, 2007, 129:1261; Huang et al, Biochemical Society Transactions, 2009: 37-217), this specific phosphorylation event was investigated. The HALNP system achieved a 40% knockdown of the phosphorylation of AKT at the lower concentration of 50 pmol while a concentration of 150 pmol was required to achieve a 60% knockdown using Lipofectamine, indicating the higher efficiency of the LNP platform. A downstream target of PI3K/AKT activation is Ki67, a common proliferation marker that correlates to cellular proliferation rates due to its presence during active phases of cell cycle and sharp decline during rest cycles (see e.g., Yerushalmi et al, The Lancet Oncology, 2010, 11:174). Following transfection, a Ki67 protein knockdown of about 40% was observed with the HALNP system compared to a 50% knockdown to the LF2K high dose control. These results directly correlated with the reduction of cellular proliferation depicted by phase contrast imagery. The LF2K 50 pmol miR125a-5p as well as the empty HALNP had no effect on Ki67 protein expression and cellular proliferation rates.

Example 26. MAPK Pathway

The effect of miR125a-5p transfection on the MAPK pathway was also investigated. The MAPK pathway is vital in cellular functions including proliferation, growth, and senescence (see e.g., McCubrey et al, Biochimica et Biophysica Acta (BBA) —Molecular Cell Research, 2007, 1773:1263; Santarpia et al, Expert Opinion on Therapeutic Targets, 2012, 16:103). Transfection of 21MT-1 cells with miR125a-5p resulted in a 20% reduction of the phosphorylation of ERK1/2 by delivery via HALNPs, and a 30% reduction in by the LF2K high dose positive control. This data, coupled with the PI3K/AKT pathway confirmed that the main two signaling cascades of HER2 were knocked down following HALNP mediated miR125a-5p transfection. A comprehensive view of Western Blot analysis is shown in FIG. 13A. In all analyses shown, the LF2K 50 pmol and HALNP control induced no statistically relevant protein knockdown.

Example 27. In Vitro Glioblastoma Assays

The following general materials and methods were used for Examples 28-31, describing targeted delivery of cargo to CD44 overexpressing glioblastoma cells.

Materials

For hyaluronic acid coated liposome nanoparticle creation, high molecular weight hyaluronic acid (HA) (~1.65 MDa), 1,2-Dipalmitoyl-sn-Glycero-3-Phosphoethanolamine (DPPE), Cholesterol (CHOL), and 1-ethyl-3-(3-dimethylaminopropyl)carbomiide (EDAC) were purchased from Sigma Aldrich (St. Louis, Mo., USA). Additionally, L α-Phosphatidylcholine (PC), Top Fluor fluorescently conjugated cholesterol (FCHOL), and a mini-extruder apparatus were purchased from Avanti Polar Lipids (Alabaster, Ala., USA). For flow cytometry analysis, flow cytometry tubes were purchased from Becton Dickenson (Franklin Lakes, N.J., USA). For cell culture, all tissue culture petri substrates were purchased from Fisher (Waltham, Mass., USA).

Lipid Nanoparticle Fabrication and Hyaluronic Acid Surface Decoration

Multilamellar vesicles were made from PC, DPPE, and CHOL in a 3:1:1 molar ratio and doped with 0.15 mass % FCHOL (as a tracker) by applying the dry lipid film technique, mechanically extruded to the nanoscale, and surface decorated with HA as described above (see also, e.g., Hayward et al, J. Biomed. Nanotechnol. 2016, 12:554-568; Hayward et al, Sci. Rep. 2015, 5:14683). For example, extrusion was performed in a stepwise manner at 65° C. ensuring product homogeneity and a final lipid nanoparticle (LNP) diameter in the 80-100 nm range. Following LNP purification via ultracentrifugation to remove any excess lipid debris (1.5 hr, 135,000 g), the primary amine of the DPPE lipid head group was amide bonded to the carboxylic acid group of EDC-activated HA to form HA decorated LNPs (HALNPs) following standard crosslinking protocol. The HALNPs were then purified form excess crosslinking reagents and either 1) stored at 4° C. and used within 2 weeks of creation or 2) snap frozen and lyophilized as described above and in Hayward et al, J. Biomed. Nanotechnol. 2016, 12:554-568). Lyophilized HA coated particles were observed to be stable for over two months when stored at −80° C. To determine the effect of HALNP membrane fluidity on the kinetics of drug release, the molar ratio of cholesterol was varied from 20 to 25% and a model therapeutic cargo, FITC tagged Dextran, was encapsulated into the aqueous core of the HALNPs as described above and in Hayward et al, *J. Biomed. Nanotechnol.* 2016, 12:554-568). Although the higher cholesterol formulation extended drug release profiles, this higher cholesterol content was found to reduce encapsulation efficiency. As a result, 20 mol % particles were used for the HALNP composition and glioblastoma assays.

Table 4 shows the size and charge characterization of the lipid nanocarrier, pre and post surface-modified with high molecular weight HA used in assays for targeted delivery to CD44 overexpressing glioblastoma cells.

TABLE 4

|  | Hydrodynamic Diameter (nm) | Polydispersity Index (PI) | Zeta Potential (mV) |
| --- | --- | --- | --- |
| LNP | 95.0 ± 0.7 | 0.032 | −5.74 ± 2.24 |
| HALNP | 126.6 ± 5.62 | 0.157 | −23.64 ± 1.49 |

Dynamic Light Scattering and Zeta Potential Characterization

Hydrodynamic diameter and zeta potential of the LNPs and HA coated LNPs (i.e., HALNP or HA-LNP) was measured using a Brookhaven NanoBrook ZetaPALS zeta potential and dynamic light scattering instrument (Holtsville, N.Y., USA). The nanoparticle size was measured as an intensity averaged distribution using a scattering angle of 90°. The Smoluchowki model was utilized to calculate the zeta potential from mobility measurements. All measurements were performed in 0.05×PBS (pH 7.4) at 25° C.

Cell Cultures

Primary cortical (Cort) and cerebellum (Cereb) astrocytes were prepared from 1-2 day-old Charles River (Wilmington, Mass., USA) Sprague-Dawley rat pups according to standard protocols (see e.g., Natarajan et al, *PLOS One*; 10:e0134541). Briefly, the Cort and Cereb brain regions were isolated, digested with trypsin and DNase, filtered through a 70 micron filter, centrifuged, and suspended in complete culture media prior to seeding. The Cort and Cereb Astrocytes were cultured in DMEM/F12 supplemented with 10% FBS and 1% PS from Life Technologies (Grand Island, N.Y., USA).

Mouse microglia were grown in macrophage serum free media containing L-glutamine and supplemented with 10% FBS and 1% PS. Additionally, recombinant mouse granulocyte macrophage colony stimulating factor (GM-CSF) from Life Technologies was added to each seeded flask at a concentration of 10 ng/ml and replenished every 3 days.

A172 (ATCC: CRL1620) human glioblastoma cell line was grown in DMEM/F12 supplemented with 10% FBS and 1% PS. U251 (Sigma) human glioblastoma astrocytoma and U87MG (ATCC: HTB14) human grade IV astrocytoma/glioblastoma cell lines were grown in MEM media supplemented with 10% FBS, 1% PS, 1% NEAA, and 1 mM Sodium Pyruvate (Thermo Scientific; Waltham, Mass., USA).

Flow cytometry

Flow cytometry was performed using a FACSCantoII from Becton Dickenson (Franklin Lakes, N.J., USA). Each of the six cell types of the in vitro brain model were seeded at a density of 100,000 cells per well in a 12 well plate layout and allowed to incubate overnight to facilitate cell attachment. After incubation, HALNPs fluorescently doped with 0.15 mass % FCHOL as a tracker were added to the cells at a concentration of 105 µg lipid per well and incubated for 3 or 12 hours. Directly after this incubation time, the cells were washed three times with sterile 1×PBS, trypsinized, and measured for per cell and population wide fluorescence (ex. 495, em. 520; 10,000 total events/read). By reading control cells without the addition of HALNPs, a lower limit gating event was created to remove cell specific auto fluorescence.

Confocal Microscopy

An Inverted confocal microscope (Olympus IX 81) at the UNL Microscopy Core Research Facility was used for the following experiments:

1) Confocal of the Fluorescently Tagged HALNPs

FCHOL doped HALNPs were diluted to 55 ng/ml in 1×PBS and the solution was viewed at 100× magnification with optical zoom using a cover slip (ex. 495, em. 520).

2) Quantitative HALNP Uptake Between the In Vitro Brain Model

Cort Astro, Cereb Astro, MG, A172, U251, and U87MG cells were seeded at 230,000 cells per 35 mm glass bottom dish from Mattek (Ashland, Mass., USA) overnight to promote cell attachment. The next morning, 1.58 mg/mL HALNP was added per dish and incubated for 3 hours. During the final half hour of the incubation, cellular nuclei were stained with Hoerscht (Thermo Scientific) following stated protocol. Subsequent to the staining procedure, each dish was washed 3× with sterile 1×PBS and kept in HEPES buffered media without phenol red during the confocal visualization. A constant laser intensity was used to take photos at 20× and 60× for each cell type for a quantitative measurement of HALNP uptake.

3) Lysosomal Co-Localization

Cort Astro, MG, and A172 cells were seeded at 230,000 cells per 35 mm glass bottom dish from Mattek overnight to promote cell attachment. The next morning, 1.58 mg/mL HALNP was added per dish and incubated for 5 hours, and the intracellular lysosomes and nuclei were stained according to protocols described above and in Hayward et al, *J. Biomed. Nantechnol.* 2016, 12:554-568. Following incubation, the cells were washed and visualized at 100×. Z-axis slices were merged to display the occurrence of HALNP-lysosome co-localization in each cell type.

4) Z-Axis Transformation with A172 Cells

A172 cells were seeded at 230,000 cells per glass bottom plate, incubated with 1.58 mg/mL HALNP for five hours, and the lysosomes and nuclei were stained. A Z-axis transformation was then performed (100× with optical zoom) using the stained cell nucleus as an internal reference point. From this analysis, an XZ and YZ plan were constructed to directly visualize cytoplasmic HALNPs.

Western Blot

Total protein was extracted from Cort Astro, Cereb Astro, MG, A172, U251, and U87MG cells cultured on standard TCPS surfaces by RIPA buffer induced cell lysis and protein solubilization followed by the scraping method. Western blotting was used to determine the expression of the cell surface receptor CD44 in each of the six brain cells. BCA protein quantification kit from Abcam (Cambridge, Mass., USA) was used to quantify total protein concentration, 25 µg total protein was loaded per lane, the blot was run on a 7.5% tris-glycine SDS PAGE homemade gel, the membrane was probed for CD44 (Abcam; ab24504), and protein bands were developed and quantified by use of a LI-COR (Lincoln, Nebr., USA) Odyssey FC and Image Studio Lite ver. 5.0 software, respectively. GAPDH (Millipore; ABS16) expression was measured as a normalization control for loading.

Saturation of CD44 Receptor (Competition Assay)

Cort Astro, Cereb Astro, MG, A172, U251, and U87MG cells were seeded overnight at a density of 100,000 cells per well in a 12 well plate. The next morning, 250 µg of HA was added to select wells and incubated for 1 hour at 37° C. Following this pre-treatment procedure, 105 µg fluorescently doped HALNPs were incubated with the cells for three hours and then flow cytometry analysis was used to directly measure the difference in per cell fluorescence between the HA pre-treated samples and non HA-pretreated samples (of analogous HALNP incubation time and concentration).

DOX Potency Assay

Encapsulation of DOX into HALNPs Doxorubicin (DOX) was encapsulated inside the aqueous core of the HALNPs as described above and in Hayward et al, *Sci. Rep.* 2015, 5:14683. Briefly, a vial of lyophilized HALNPs (0.5 mg lipid) was brought to room temperature, and rehydrated with 1/10th its original pre-lyophilized volume of 0.05×PBS containing 250 µg DOX. Following a thirty minute incubation time to allow for lipid membrane re-assembly, the vial was brought back to its full pre-lyophilized volume with 1×PBS and ultracentrifuged to remove non-encapsulated DOX (140,000 g, 4° C., and 1.25 hr.). The auto-fluorescent property of DOX was then used to determine the entrapment payload. A standard curve consisting of a known amount of DOX was compared to 0.1% triton X-100 permeabilized HALNPs to determine the total encapsulated DOX. A final lipid to DOX mass ratio of 2.88 to 1 was achieved with a 69.4% encapsulation efficiency. These purified DOX containing particles are referred to as HALNP-DOX.

Cort Astro, MG, and A172 cells were seeded in a 48 well plate at a density of 35,000 cells per well and incubated overnight to facilitate cell attachment. The next day following validation of homogenous cell attachment, DOX in its free form (i.e., not associated with a nanocarrier) or HALNP-DOX were added to select wells in a concentration range of 0 to 10 µg/mL and incubated for an additional 24 hours.

To determine the effect of free DOX and HALNPDOX on the cell viability of Cort Astro, MG and A172 cells, an MTT assay was utilized as described herein to calculate the lethal concentration to kill 50% of the cells (see also, e.g., Hayward et al, *Sci. Rep.* 2015, 5:14683; Wilson et al, *Nanoscale*, 2015, 7:18477-18488; Natarajan et al, *PLOS One*, 2015, 10:e0134541). Following the 24 hour DOX incubation time, the medium of the cells was aspirated, and sterile 5 mg/mL MTT working solution was added and incubated for 2 hours at 37° C. The cells were then lysed with acidified IPA and the absorbance of the produced formazan crystals was measured using a Beckman Coulter AD340 plate reader (Indianapolis, Ind., USA). Percent viability was determined by normalization of the 570/620 absorbance ratio to the control untreated cells and positive control dead cells (ethanol treated).

Statistical Analysis

The difference between experimental groups was investigated by a one-way analysis of variance (ANOVA) and by a subsequent Turkey's multiple comparison test in Sigma Plot Software. For statistical analysis of all data, $p<0.05$ was regarded as the lowest acceptable threshold for significance.

Example 28. Targeted Delivery to CD44 Overexpressing Glioblastoma Cells

To test HA driven active targeting for GBM (glioblastoma) therapy, cell cultures consisting of primary rat astrocytes, primary mouse microglia cells, and human GBM cells were utilized. Specifically, three GBM cells lines were selected to obtain results spanning different source donors as well as to probe the potential of treating GBM cells with varying phenotypical properties such as invasive and non-tumorigenic (A172 cells), non-invasive and slightly tumorigenic (U251), and invasive and highly tumorigenic (U87MG) (see e.g., de Ridder et al, *Acta Neuropathol*, 1987, 72:207-213).

Figure 14A:
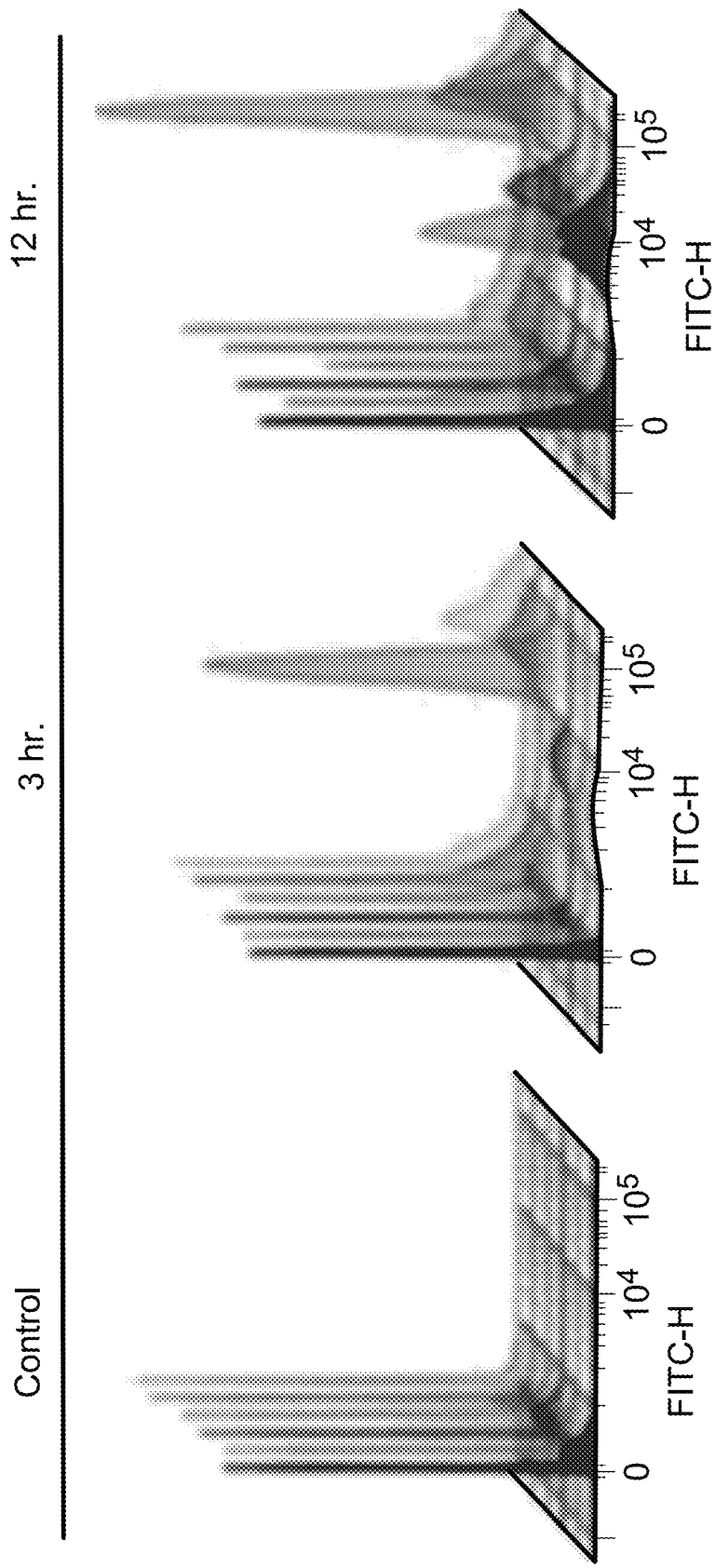
FIGS. 14A-14D show HALNP uptake rate and extent in glioblastoma, astrocytes and microglial cells. Flow cytometry was used to measure HALNP uptake via histogram (FIG. 14A), population wide (FIG. 14B, and per-cell fluorescence (FIG. 14C) following a 3 h and 12 h incubation time in cerebellum astrocytes (Cereb Astro), cortical astrocytes (Cort Astro), microglial (MG), and three glioblastoma (GBM) cell lines (A172, U251, and U87MG). **$p<0.005$, *$p<0.05$ relative to both astrocytes and MG at the same time point; ## $p<0.005$, # $p<0.05$ relative to the same cell type at the previous time point; n=4). For each cell type, control cells (i.e., no HALNP) were used to create a lower limit-gating event to remove cell specific auto-fluorescence.
Figure 14B:
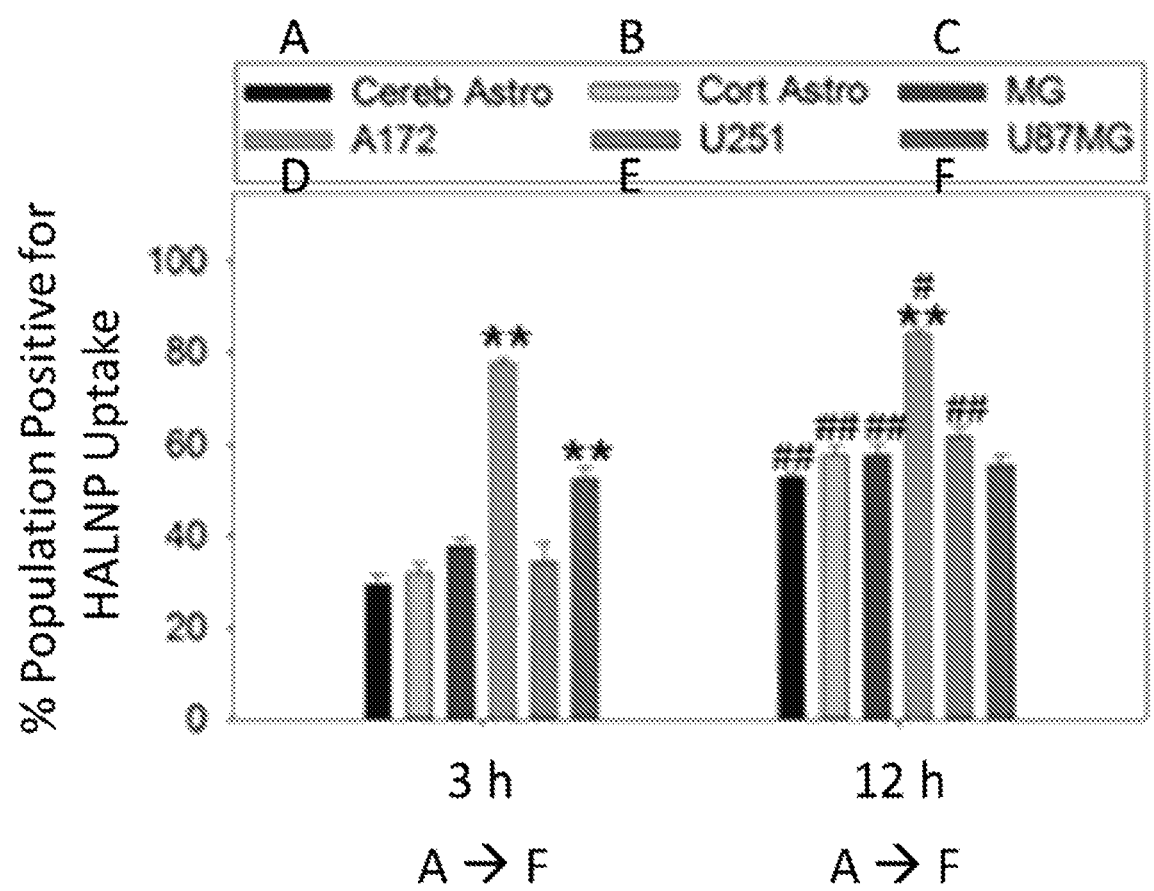
Figure 14C:
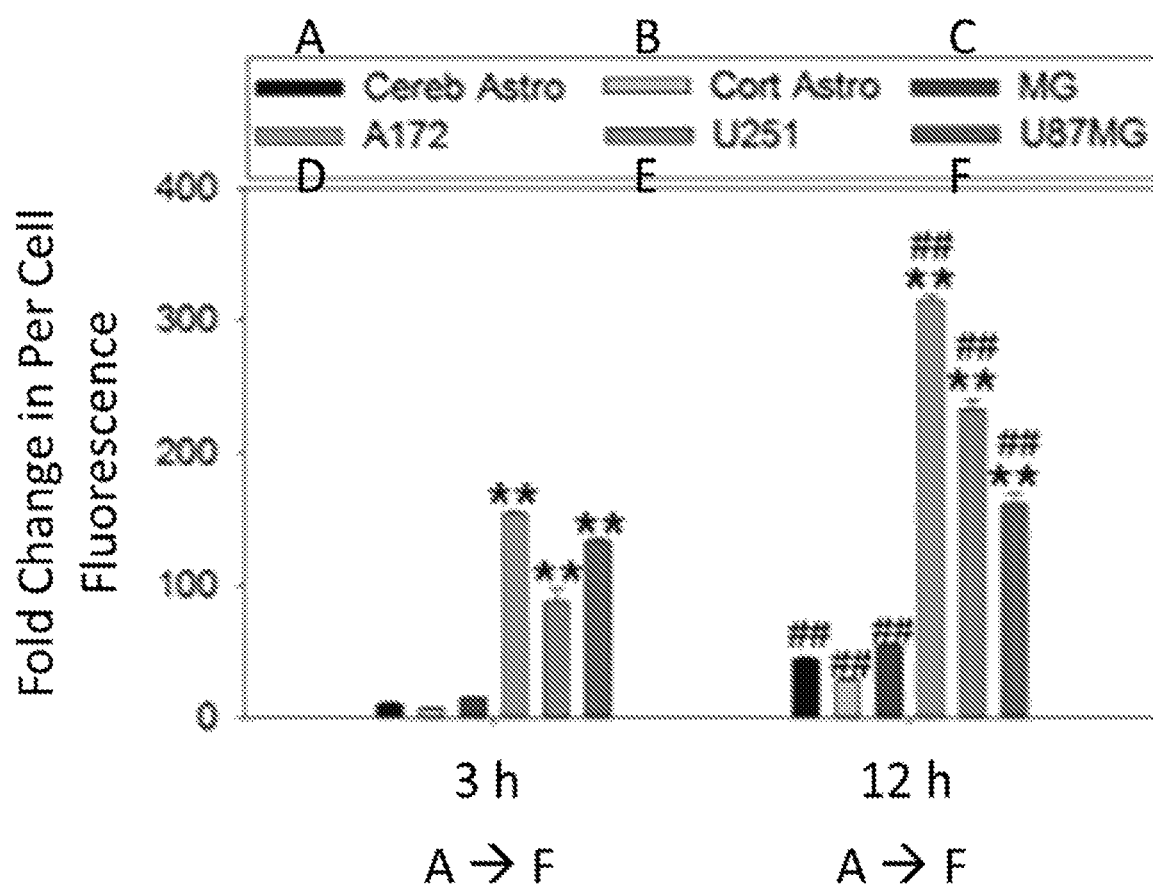
Figure 14D:
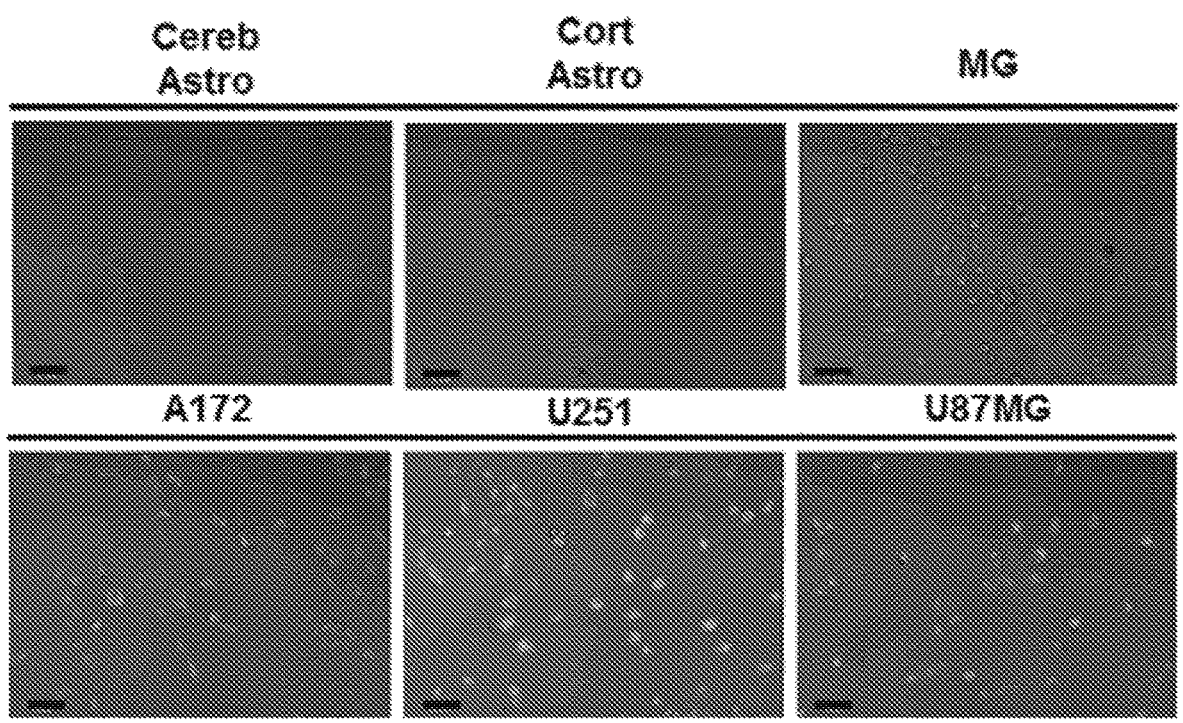

The targeting capacity of HA was directly assessed in GBM cells along with MG and astrocytes using flow cytometry analysis as shown in FIG. 14A. Flow cytometry was selected due to its capacity to examine uptake simultaneously in both a population wide, as shown in FIG. 14B, and per cell basis, as shown in FIG. 14C. Prior to analysis, all six cell types were seeded at low density to ensure the uptake data acquired was indicative of per-cell behavior (Supplementary FIG. 3). Following a three hour incubation time with the HALNPs, the cerebellum and cortical astrocytes exhibited 29.3% and 32% positive populations for HALNP uptake, and a 10 and 6.7 fold change in per cell fluorescence, respectively. At the same time point, the MG cells had a 37.7% positive population, and a 14.5 fold change in per cell fluorescence, while the A172, U251, and U87MG GBM cells achieved 77.7%, 34.5%, and 52.5% positive populations with 153.4, 87.3, and 133.3 fold change in per cell fluorescence, respectively. This significant difference in HALNP uptake between the glial (astrocytes and microglial) and the GBM cells was further corroborated by quantitative confocal microscopy at the analogous three hour time point, as shown in FIG. 14D.

Flow cytometry was also performed after a 12-hour incubation with HALNPs to show if the differential cell uptake patterns were transient or long lived via a preferential mechanism. Following this incubation time, the cerebellum and cortical astrocytes had a 57.8% and 52.9% positive population and a 43.8 and a 28.6 fold change in per cell fluorescence, respectively. Furthermore, the MG cells reached a 57.7% population and a 54.3 fold change in fluorescence, while the A172, U251, and U87MG GBM cells attained 84.1%, 61.8%, and a 55% positive populations with 314.6, 233.3 and 161.7 fold change in per cell fluorescence, respectively. These experiments demonstrated the potential of employing HALNPs for targeting GBM cells. In addition, the results obtained indicate that HA may bind with the GBM cells differently than the healthy glial cells to facilitate preferential intracellular delivery.

Figure 15:
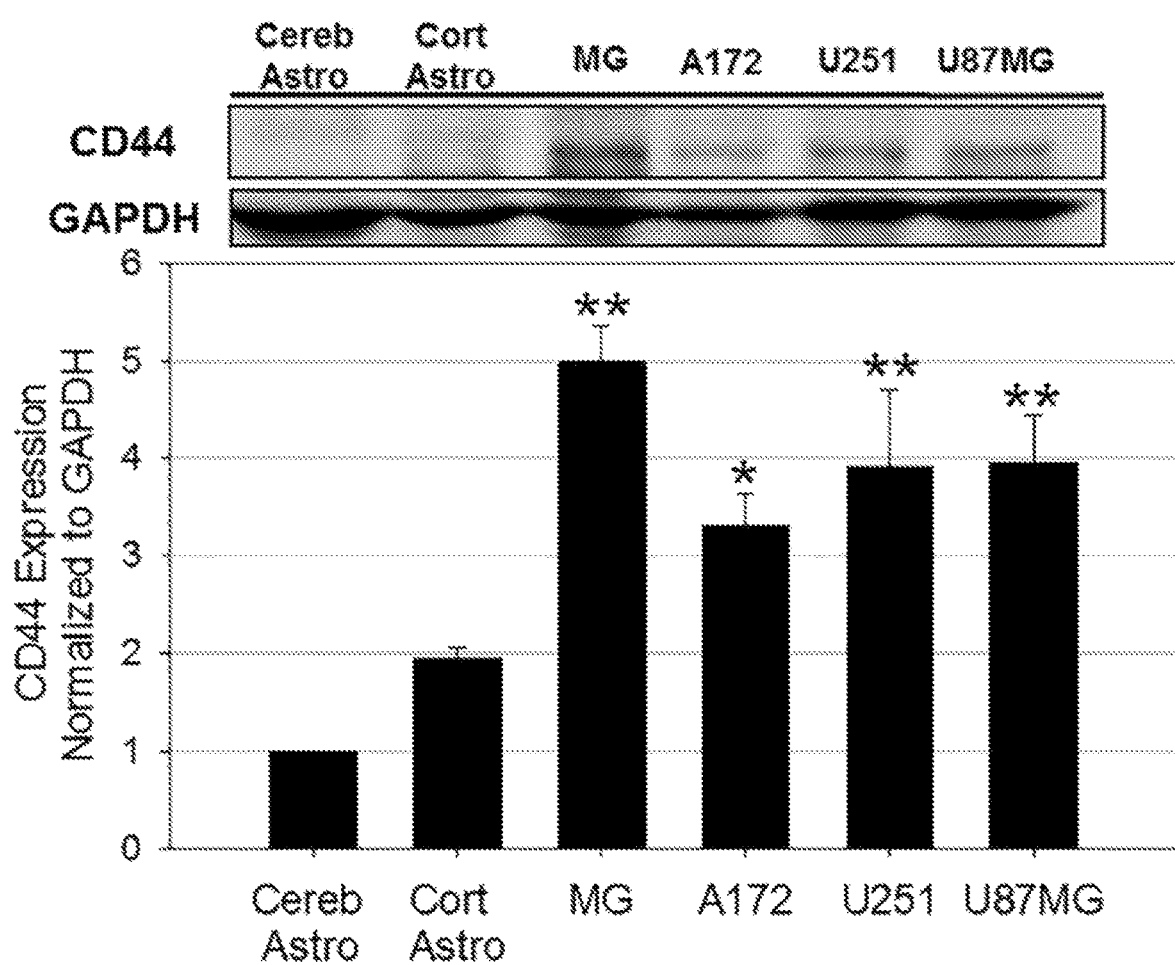
FIG. 15 shows CD44 protein expression analysis in six cells in the GBM tumor microenvironment. Cerebellum astrocytes (Cereb Astro), cortical astrocytes (Cort Astro), microglial (MG), and three glioblastoma cell lines (A172, U251, and U87MG) (**$p<0.005$, *$p<0.05$ relative to both Cereb Astro and Cort Astro; n=3). GAPDH was used as the loading control.

Example 29. Differential Expression of CD44 Facilitates Active Targeting of Glioblastoma Cells CD44 is a cell surface receptor which can be used for targeted therapy for a range of cancer types (see e.g., Platt et al, *Mol. Pharm.* 2008, 5:474-486) and has been shown to play a role in regulation of macrophage phagocytosis and inflammation pathways (see e.g., Vachon et al, *Blood*, 2007, 110:4492-4502; Vivers et al, *Clin. Sci.* (*Lond*). 2002, 103: 441-449). To investigate if the preferential uptake of HALNPs to glioblastoma (GBM) cells over astrocytes and microglia (MG) cells is driven by CD44 western blot was performed to quantify total CD44 protein levels in all six cells types, as shown in FIG. 15. From this analysis it was found that CD44 is expressed lowest in both cerebellum and cortical astrocytes, higher in the GBM cells, and highest in the MG cells. By using the cerebellum astrocytes as a comparison baseline for CD44 expression, it was found that cortical astrocytes, MG, A172, U251, and U87MG GBM cells had a 2, 5, 3.3, 3.8, and 3.9 fold higher expression, respectively. This data correlates with recent findings that CD44 expression is increased in glioma cells as compared to healthy astrocytes (see e.g., Asher et al, *Exp. Cell Res.* 1992, 203:80-90; Yoshida et al, *Pathol. Int.* 2012, 62:463-470).

Figure 16:
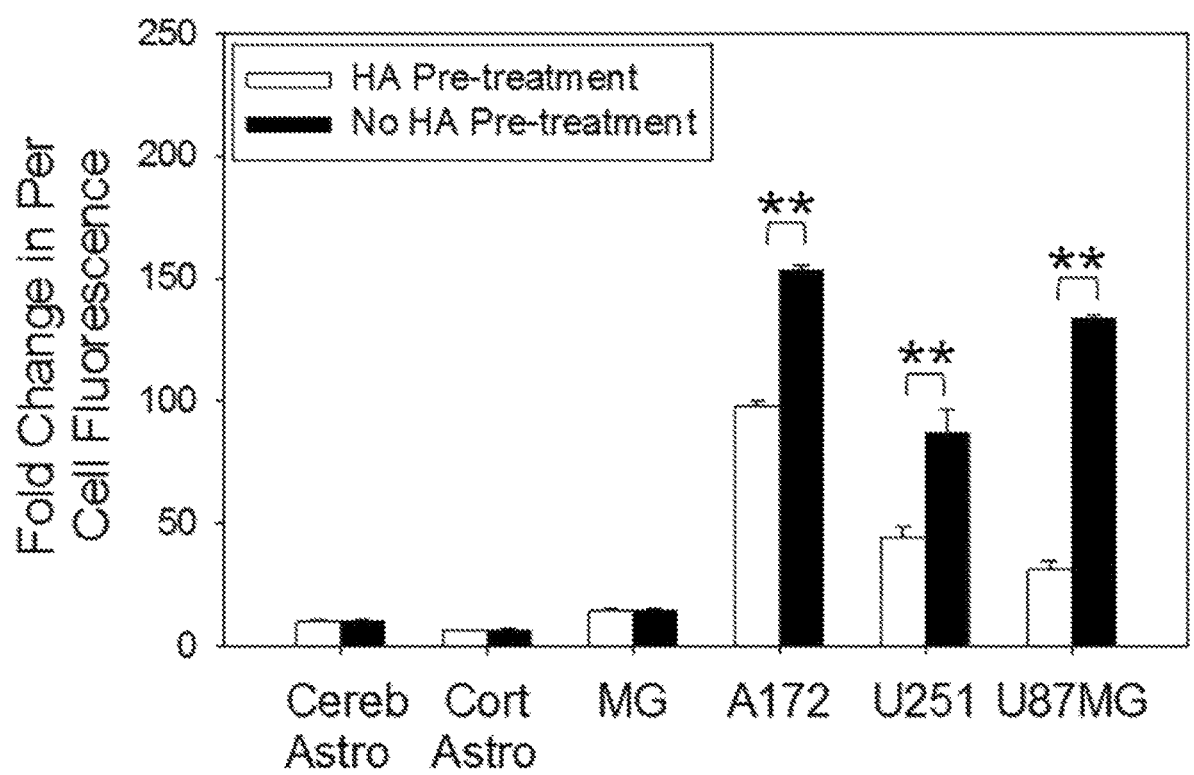
FIG. 16 shows results of a CD44 receptor saturation assay measuring the rate of per cell fluorescent HALNP uptake. Excess HA was used to saturate CD44 receptors, allowing for the direct quantification of CD44 mediated HALNP endocytosis capacity of each cell type (**$p<0.005$, *$p<0.05$; n=4). 3 h time point shown.

A saturation experiment was then performed to precisely block the CD44 receptor to discern if the increase in total CD44 expression translated to a higher uptake of the HAL-NPs, as shown in FIG. 16. Each of the cell types was pre-treated with excess HA prior to the addition of the HALNPs, and then the per-cell fluorescence was directly compared between the pre-treated and non-pretreated samples. The percent difference in uptake was then used as a quantitative measure as to the capacity of each specific cell type to employ CD44-HA receptor endocytosis of the HAL-NPs. From this analysis it was found that both cerebellum and cortical astrocytes do not internalize HALNPs via a CD44 driven route, and thus any uptake into these cells is facilitated by nonspecific interactions. Similarly, HA pre-treatment did not significantly influence HALNP uptake in MG cells although they exhibited the highest total CD44 expression. In contrast, A172, U251, and U87MG GBM cells were found to significantly employ CD44 stimulated uptake yielding a percent difference in per-cell fluorescence of 36%, 48%, and 76%, respectively.

Figure 17A:
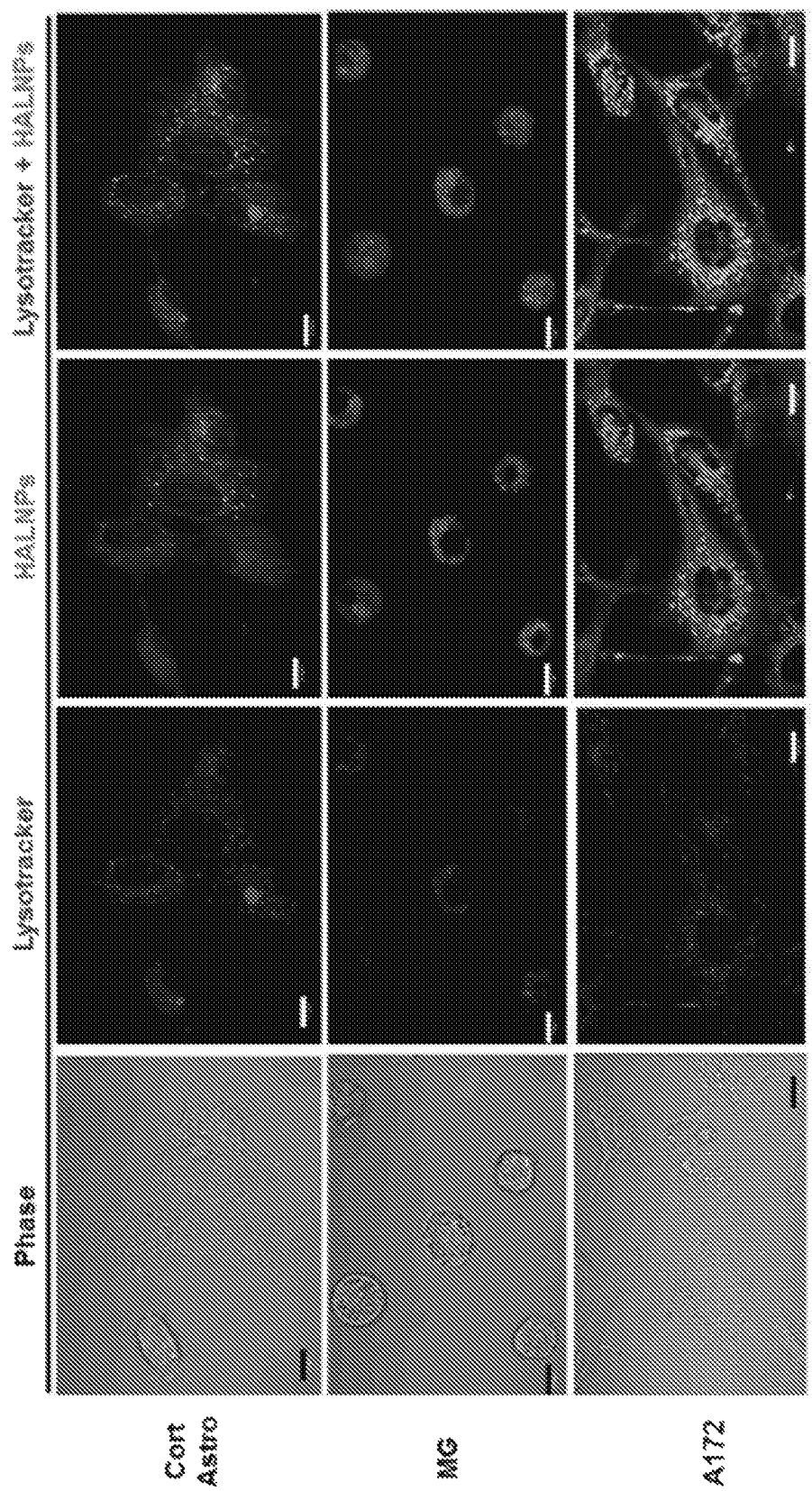
FIGS. 17A-17B show HALNP intracellular fate in healthy glial versus GBM cells.
Figure 17B:
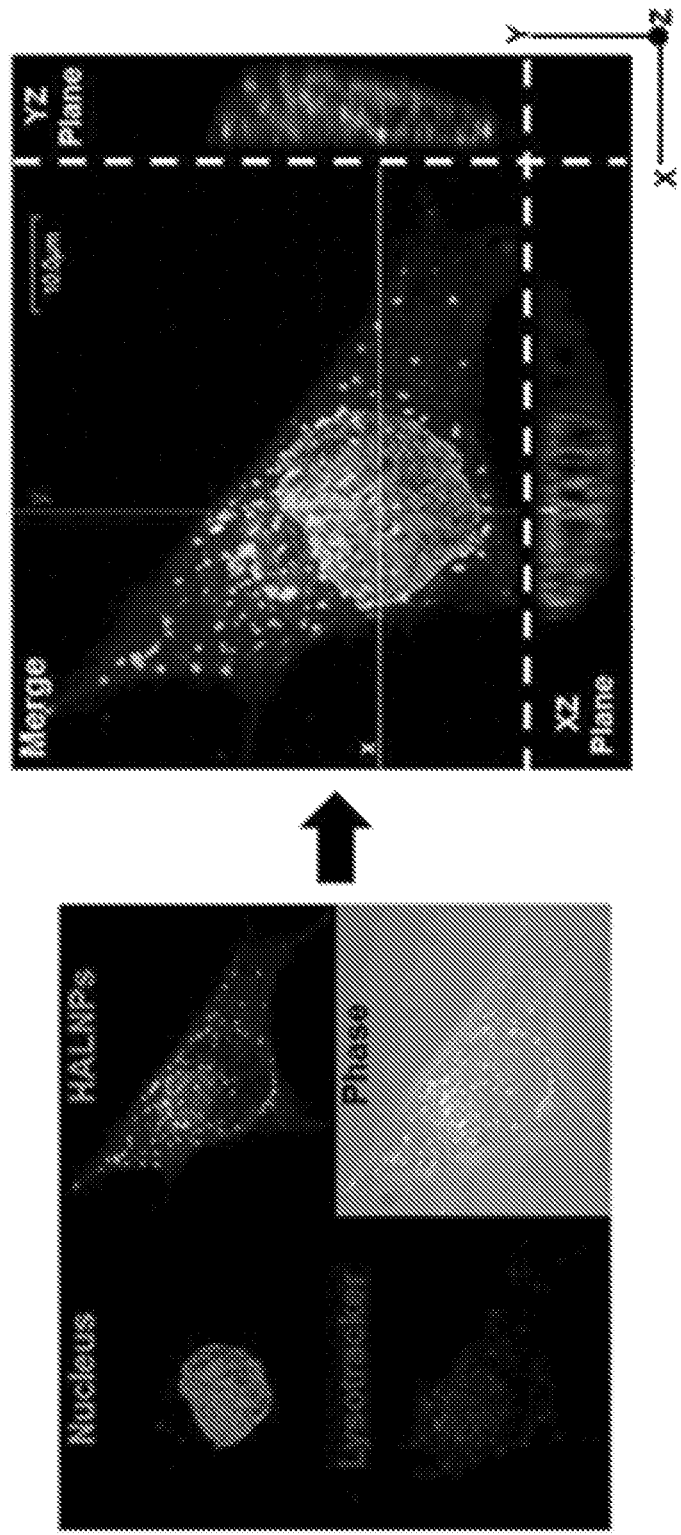

Example 30. CD44 Stimulated Uptake of HALNPs Leads to Endolysosomal Escape in GBM Cells To investigate the intracellular distribution of HALNPs as a function of CD44 receptor employment, live cell confocal microscopy was performed to visualize the HALNP-lysosome co-localization patterns to directly test if cells that exploit CD44 driven uptake (e.g., GBM cells) have different HALNP intracellular fate than that of cells that do not readily utilize CD44 (e.g., astrocytes, MG). For this analysis, cortical astrocytes, MG, and A172 as representative cells were selected for each cell type, and incubated the cells with HALNPs for five hours prior to confocal investigation. Using high magnification confocal microscopy and z axis slicing as shown in FIG. 17A, it was observed that cortical astrocytes and MG cells displayed extensive HALNP co-localization with lysosomes. The A172 cells had significantly less HALNP co-localization with lysosomes following intracellular delivery. To further authenticate that the HALNPs achieved cytoplasmic escape in the A172 cells following CD44 driven uptake, confocal microscopy was then performed with z-axis transformation as shown in FIG. 17B. This technique allowed for the direct visualization of HALNPs in comparison to an internal reference frame (e.g., the cell nucleus) to better show that the HALNPs achieved homogenous cytoplasmic distribution with minimal lysosomal co-localization. The confocal analysis results indicate that the combination of preferential uptake and lysosomal evasion in GBM cells as opposed to the non-specific uptake and lysosomal co-localization of healthy glial cells may lead to enhanced potency and reduced offsite toxicity for HALNP facilitated GBM therapy.

Example 31. Delivery Selectivity and Efficacy

Figure 18:
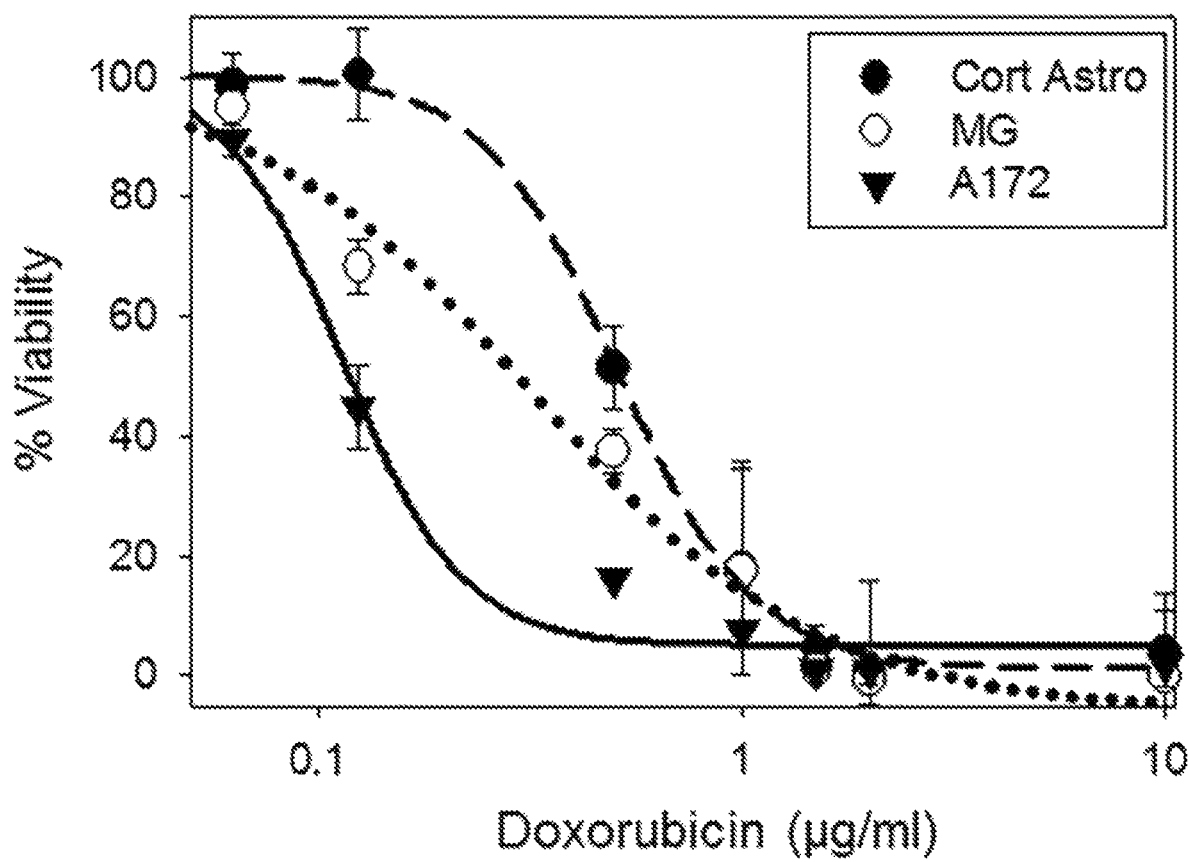
FIG. 18 shows results of a potency assay using doxorubicin (DOX) to investigate the influence of HALNP targeting specificity and endolysosomal escape on therapeutic efficacy. HALNP encapsulated DOX (HALNP-DOX) potency was compared between glial (cortical astrocytes-Cort Astro and microglial-MG) and GBM (A172) cells following a 24 hour incubation time (n=3).

The therapeutic potential of HA as a targeting ligand for GBM treatment was tested by encapsulating doxorubicin into the HALNPs and performing a 24-hour potency assay with cortical astrocytes, MG, and A172 cells as described above in Example 27. A Lipid:DOX mass ratio of 2.88:1 was achieved and the final DOX loaded particles were 167.8±9.2 nm in size, −21.19±5.2 mV in charge, and had a PI of 0.241. The three cell types were seeded overnight and then a potency assay was performed the next morning over a DOX range (encapsulated DOX) of 0 to 10 µg/mL. Following the 24 hour incubation time, a standard MTT viability assay was used to determine the lethal concentration to kill 50% of the cell population ($LC_{50}$), as shown in FIG. 18. This assay demonstrated that the $LC_{50}$ of HALNP encapsulated DOX for the A172 cells was nearly 5 fold lower than the $LC_{50}$ for the cortical astrocytes, and nearly 3 fold lower than the $LC_{50}$ for the MG cells. Specifically, the $LC_{50}$ values were found to be 0.511±0.039, 0.317±0.048, and 0.114±0.010 µg/ml DOX for the Cort astro, MG, and A172 cells, respectively, as shown in Table 5. These results show the significant advantage of employing HA as an active GBM targeting ligand.

To further probe the specificity of HA mediated targeting, a 24-hour potency assay was performed with the three cells types utilizing DOX in its free form (i.e., not conjugated with a nanocarrier). It was found that DOX was less potent in the cortical astrocytes and most potent in the A172 cells. $LC_{50}$ data for Free DOX and HALNP-DOX are shown below in Table 5.

TABLE 5

Potency assay with doxorubicin (DOX) $LC_{50}$ values (µg/ml) following the 24-hour incubation time

| Cell | Free DOX | HALNP-DOX |
| --- | --- | --- |
| Cort Astro | 0.322 ± 0.053 | 0.511 ± 0.039 |
| MG | 0.267 ± 0.050 | 0.317 ± 0.048 |
| A172 | 0.193 ± 0.030 | 0.114 ± 0.010 |

This experiment also validated the targeting capacity of HA. For example, by comparing the HALNP-DOX $LC_{50}$ to the free DOX $LC_{50}$ for each specific cell type, the therapeutic influence of specificity was quantified. For the cortical astrocytes, the $LC_{50}$ value significantly increased by 59% by utilizing the HALNP system over free DOX. Similarly, the $LC_{50}$ increased by 19% due to delivery of DOX encapsulated in the HALNPs system to the MG cells. These results exemplify that the HALNP nanoparticles are not readily internalized into healthy glial cells, and thus the HALNP nanocarrier may reduce the chance of offsite toxicity for GBM therapy. The $LC_{50}$ value also decreased significantly by 41% for the A172 GBM cells via employment of the HALNP conjugates. This assay confirmed that the HALNP conjugate increases the overall efficacy and safety of chemotherapeutic GBM therapy.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A composition comprising:
   i) one or more hyaluronic acid conjugated liposomes; and
   ii) a polyelectrolyte multilayer;
   wherein the hyaluronic acid is covalently bonded to the surface of the liposome;
   and wherein the one or more hyaluronic acid conjugated liposomes are deposited onto the polyelectrolyte multilayer.

2. The composition of claim 1, wherein the polyelectrolyte multilayer comprises one or more independently selected polycationic polymers.

3. The composition of claim 1, wherein the polyelectrolyte multilayer comprises one or more independently selected polyanionic polymers.

4. The composition of claim 3, wherein at least one of the polyanionic polymers is poly(sodium styrene sulfonate) (SPS).

5. The composition of claim 1, wherein the polyelectrolyte multilayer comprises from about 2 to about 10 monolayers of poly-L-lysine (PLL) and from about 2 to about 10 monolayers of poly(sodium styrene sulfonate) (SPS).

6. The composition of claim 1, wherein the liposome comprises a hydrophilic core and a hydrophobic lipid bilayer.

7. The composition of claim 1, wherein the liposome further comprises one or more therapeutic agents.

8. The composition of claim 6, wherein each of the therapeutic agents is independently localized in the hydrophilic core or hydrophobic lipid bilayer of the liposome.

9. The composition of claim 1, wherein the liposome further comprises a fluorescently tagged lipid.

10. The composition of claim 1, wherein the liposome further comprises a targeting moiety.

11. The composition of claim 10, wherein the targeting moiety is conjugated to the hyaluronic acid.

12. The composition of claim 1, further comprising an additional polyelectrolyte multilayer.

13. The composition of claim 1, further comprising a substrate selected from the group consisting of a medical device, a tablet, a capsule, a bandage, a gel, and a nanoparticle.

14. The composition of claim 2, wherein at least one of the polycationic polymers is poly-L-lysine (PLL).

* * * * *

SEQUENCE LISTING

```
<160> NUMBER OF SEQ ID NOS: 4

<210> SEQ ID NO 1
<211> LENGTH: 20
<212> TYPE: DNA
<213> ORGANISM: Homo sapiens

<400> SEQUENCE: 1
aggggccatc cacagtcttc                                           20

<210> SEQ ID NO 2
<211> LENGTH: 7
<212> TYPE: DNA
<213> ORGANISM: Homo sapiens

<400> SEQUENCE: 2 agaaggc                                                          7

<210> SEQ ID NO 3
<211> LENGTH: 20
<212> TYPE: DNA
<213> ORGANISM: Homo sapiens

<400> SEQUENCE: 3
tgatgaggat cccaaagacc                                           20

<210> SEQ ID NO 4
<211> LENGTH: 20
<212> TYPE: DNA
<213> ORGANISM: Homo sapiens

<400> SEQUENCE: 4
aactgcaccc actcctgtgt                                           20
```